United States Patent
Wagner et al.

(10) Patent No.: US 10,941,408 B2
(45) Date of Patent: *Mar. 9, 2021

(54) SYSTEM, METHOD, AND DEVICE FOR THE EXPRESSION OR REPRESSION OF PROTEINS

(71) Applicants: SOLARVEST BIOENERGY INC., Montague (CA); UNIVERSITY OF GENEVA, Geneva (CH)

(72) Inventors: Richard E. Wagner, Bloomington, IN (US); Raymond Surzycki, Bloomington, IN (US); Jean-David Rochaix, Mies (CH)

(73) Assignee: SOLARVEST BIOENERGY INC., Montauge (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/125,913

(22) Filed: Sep. 10, 2018

(65) Prior Publication Data

US 2019/0194675 A1    Jun. 27, 2019

Related U.S. Application Data

(63) Continuation of application No. 14/859,779, filed on Sep. 21, 2015, now Pat. No. 10,072,268, which is a continuation of application No. 12/377,238, filed as application No. PCT/US2007/017774 on Aug. 11, 2007, now Pat. No. 9,228,193.

(60) Provisional application No. 60/837,001, filed on Aug. 11, 2006.

(51) Int. Cl.
*C12N 15/82* (2006.01)

(52) U.S. Cl.
CPC ..... *C12N 15/8214* (2013.01); *C12N 15/8238* (2013.01); *C12N 15/8257* (2013.01)

(58) Field of Classification Search
None
See application file for complete search history.

(56) References Cited

U.S. PATENT DOCUMENTS 9,228,193 B2 * 1/2016 Surzycki ............ C12N 15/8214
10,072,268 B2 * 9/2018 Wagner .............. C12N 15/8257

OTHER PUBLICATIONS

Broudreau et al (2000, EMBO J. 19:3366-3376).*
Walker et al, 2005, J. Phycol. 41:1077-1093.*
Quinn et al (2003, Euk. Cell 2:995-1002).*

* cited by examiner

*Primary Examiner* — Anne Kubelik

(57) ABSTRACT

This invention relates to systems, methods, and devices for inducing andlor repressing the expression of proteins. More particularly, the invention relates to systems, methods, and devices for inducing andlor repressing the expression of proteins in plastids. An exemplary embodiment involves the regulation of the expression of proteins involved in hydrogen production to stimulate the production of hydrogen gas using the methods, systems, and devices described herein.

1 Claim, 38 Drawing Sheets
Specification includes a Sequence Listing.

```
   1 GAATTCTGCT  GCGGAAAGGT  TAACTGGCCC  AAAGACTTGC  GGCGCAGCGC
  51 TGAAATAGCT  CCCAAAACCT  AGATACGCTC  CGTCATGAAA  CAAAACATGT
 101 ATATATTAGC  AAAAGGGCGT  GACTGCCGGG  GCGAGCGGCC  TCGCCCAGCC
 151 GATCTCTCCA  TCGTGCTTGC  TGTCACCGCT  CGCTGCTCAA  CACAGGCTAA
 201 CTTAGCTTGC  CTTTGGTAGA  CATTGTGCAA  TCAGTCACAC  CTCAAGCGCT
 251 AATCTTCAAA  ATCTTTCGGT  CGACTGAAAC  GATAGTGAGC  GTCTCAGAAC
 301 GAGTCTTGTG  TAGGCCGCAC  GTTTGAAGCG  GTCGGGGCCG  TGTCCAACGT
 351 ATAGGTTGCT  GTTATCAAGA  AGAAACAAAC  CAGCTGGTAG  CAAACCTCGA
 401 ACGAAGTATG  GCACGGCCAT  AGAAGCCCGG  CCTTGCGGGA  GAACTCCGGA
 451 AA*ATGGGGGC  TCTACCGTGC  CCAGCTCATA  TCGAGCATCA  TCAGGGCTTA*
 501 *TCATCGTTTG  GGACACGGCG  AGTCCTGCGG  CAAAGCGTGG  CTTGTGGAGC*
 551 *TCACCGCAGT  CGGCGAAGGT  CCCTGTGGGC  AGGCGCT*TCT  CCCGGCGCAC
 601 CTAAATATGA  CGAGGGCGCA  TTATCGTGTA  GCTTTCAACT  GGGCTCGGCG
 651 AGCCTGCACG  TCAGCGAGGT  AGGCTTGTTT  TCTTGCCACA  GTGTATGGGT
 701 GGCTCGGGAG  ACCTGGGAGA  TCGGAGCGTT  GGGTGTTCGG  GGCTCGCGAA
 751 TGGTGCAGAA  ACAAGCTTCG  TGGCATTTAA  GGCGTCCGC   GACAATAAAC
 801 GCAGGTTCGA  GGTTCGCGAC  ACGCGACACC  AAGGGCCCCT  CCAACCGGCG
 851 GATGTATCGA  GCTCCCGAAA  ACTCTCGCGC  TCACGGAGGA  GCAGGACCAG
 901 CGGGCTGCGC  GGGCGACCAG  CCAGCTGCTA  AATGCCATCA  GTCGCTGTGC
 951 CGCGGGCTCG  CCTTTGGCGC  GCTTACTGAC  TGGTCCTCAT  GGAGCCGCGA
1001 GCGCAACTGG  TGCCGGGAGC  CACTCGTCGT  CGGCCGGGGC  GCCCACGCCG
1051 ACGCCGCGGC  CGGACATCGC  GGCCGCTGCA  GCGCTGCTCC  CCTCGCTGAC
1101 TTGGCGCTGG  GTGTCGGTGG  CGGACCTGGA  AGGAGGCTGG  GTTGACCGCG
1151 GCGTAGCGCA  CCTGCTGCGG  GAAGCCTTGC  TCGTGCAGAA  AGCCGCGTCC
1201 GACGTCAACG  CATCCGTCAG  GTGGGCAGCA  CCGCGTTCTT  AAGGCGTGAC
1251 CTGCCGTACA  TTGCTGGCAG  GGCTCTGTGG  TATGGAGCCA  TGGATGTCCG
1301 TTGCAGTTTG  TTGACTCAGC  ACGCGCTGGC  AGGCTGACAC  GCTGCGGCAT
1351 GTGTGCACGT  CCGGAAACGT  TCCTTGCGCG  AGCTGGGCTC  AACCTGACAT
1401 AATCTGCTGC  CCGCCTGCCG  CTGCTACCCT  GCGTATTCCT  CTGCCGTAGT
1451 GAGCTGGTCG  GGTGGTGCAT  GGACAACTGC  AGCGCACCCG  CGGCGGCACT
1501 GGCGGCGCTC  TGGGGGCAGC  AGCAGGGAGC  TGCGCTGCCC  GCCCGCAGCC
1551 GCAGCTTCTA  CGGCCTGCTG  CTTCAGCGCC  TGGACGGCGG  TGGCGCCAGC
1601 TCAGCAGTTG  CTGCTGCGGC  AGGCCGCCAG  CCGCACGAGC  ACCAACAGGA
1651 GCGATCATCA  GCTGAGGCGT  ACGGTCTGTC  CCCGGCACTG  GTGTTTTGCA
1701 GCTCAGTCGC  CCGCACCGCA  CTCTCCACCT  CCTCACGCCG  CGGTGGGCGC
1751 TCCTCCTCTT  CAGAGGAAGA  CGGCGATGCG  CACGACGACC  GGTCGCACCC
1801 ACATACGCAG  CAGCTGCTGG  AGCAGGACGG  GTCGGAGCCG  CTGGTTGGTG
1851 CTGCTGCGTC  CCCCTCCAGC  AATGGCAAGC  GCTCGGCGGC  TGGCCCTAGC
1901 GCCGGTGCCG  ACGTTATCCT  TGTTGGTGAG  CTGCCCGGTG  ACGTGCTATT
1951 GGACGAGTCG  GTGGGCAACG  TCCGCCGCCA  GCAGCCGCAC  GCGAACGGCT
2001 CCGGCGCTAA  GCACAACGGC  GTGAATGGCA  GCGGTAAAAG  CGGATCCGGT
2051 GGGGCCAAGG  TGGCGCATGC  GCATGTCAAC  GGCTCTGCAG  CAGACACGGA
2101 CCCAGGGCAA  GCAGCCCTGG  GCGTGAAGGG  GAGCGCAGAG  TCTCCTCTGG
2151 AGCAGCCGGC  GCCGGCGGCA  AAGCGGTCAG  CTGCAGGAAA  GGCCTCCCGG
2201 CCTGCCGCGC  TTCTCCTGAA  GCGCCCGTCC  CGCAGCGCCG  CCCCGCCAGC
2251 ACCAACGCTG  CCCGACGGTG  CGGAGGCGGA  CGGATTCGCA  TCGGACGGGA
2301 GCGGCCTGCC  AGGACACGGG  CAGCAGCAGC  TCTCCGCCAT  TGCGGCGGCG
2351 GCAGCAGCCT  CATCGCTCCT  GGCCGGCCCG  GCGGCGCCCA  TGTCGTTCCT
2401 GGAGACGCTG  AGCGACGACG  ACGACGAGGC  GCGGCGCGCG  GCGTCGCTCC
2451 TGAACGGCGC  CGGCATGTCC  GACCCCGCCT  CCGCTAGCAG  CACCAGCACC
2501 AGTAGCAACA  GCGGCACCAG  CAACCTGGTG  GGGCGTGTGT  TCGTGCCCAT
2551 GCGGCTGGTA  TCGGTCAGCC  GCTTCCGCCT  CCGCGACGCT  CTGGGCCGGC
2601 CGCTGCCCGA  CGGCCTGGCC  GTGCCGCCTA  CTGGGCCCAT  CGTGCTCAGC
```

FIG 11A

```
2651 AACGACGCCC GCGTGTTCCC CGGCACTGAG GGCCTGCTGT CCGACTACGC
2701 CACGCCCGCC GGCGACAAAC TCGCCGTACG GCTGGAATAC ATCACGGACC
2751 GCTCGTACGC GTACGGCGAC GTGGCGCTGC AGCTGTTCAA CATCAGCCGC
2801 GTGACGCGCA AGCGTACGGA CAACTGCCAG ATGCTGGTCA ACGGCAAGCC
2851 GGTCAACGTC GGCGACCCGG GTGTGCCGCT GGTGCCTGGT GACGAGATTC
2901 GGTTTGGTGC CAGCGCGGCG TTTGCGTTCC GGCTAGAGGC ACTGCCGGAG
2951 GCGCCGTCTG GGCTGGAGGC GGCGGTGCAA CAGCTACAGC TTCACGCCGA
3001 CAGCAGCAGC AGCAATGGCA ACGGCAGTGG CAGTAGCAGT AGCAGCGGGC
3051 TGCCGCAGGT CAGCGAGGAG GAGGTGGCGG CGGCGGCGGC TGACATGGCG
3101 TCCCTGTCTA ACATGTCCCG CCGTGACCCG CCCCGTGCTG AGGCGCTGCT
3151 GCGACGGCTG CTGGCGGCGC GCCGGGCGA CGCCGCGCTC TGGCTCATCT
3201 GGGCGCAGAT GGCAGCGCGC GTGGAAGGCC CCGGGCCGGG GCAGGCCAAG
3251 GCGCGGATGC TGTTCCGCGC AGCAGCCGAT GCCGCCCGGC GCATGCCTGT
3301 GCTGCCGCCG CCGCCGCTGG CGCTGCAGAT GGCGGCGCGG CGCGCCACCG
3351 GCGCCGGCCG GCGCCGTCGG CGCGGCGCCT CCACCACCGC ATCCATGGAC
3401 GGCGACGACG GCGCGCTCAG CGTTGCCGAC GGCAGCAGCA GCGCCGATGC
3451 CGCGATTGAC CCGGCATCCG GTGCTTCGCC GTCAGCTGCC GCCGGCCCGC
3501 CGGCGCCCTC CGCCCGACCG CGGCACAACT GGTTGCTTGT GCAGGCGCTG
3551 GGGAACTGGG GCAAGCACGA GTGGCGGCTG CGCATGTATG GCTCCGCGCG
3601 GCACCTGTTC CGCGCCGCGG CGGACGAGGC GGCGCGGCAC TCGGGCGGCC
3651 TGGCGGCGGG CGGCGGCGG GCGGTGATGC ACTACTGGGG CAGCCGGGAG
3701 CTGGAGGCGG GCAATGTGCG CAACGCGCGC ATCGTGGCGG CGGAGGCGCT
3751 GCGCAAGTGC CCGGCCGACG TGGCGCTGTA CGTGCTGGCA GCAAGCGTGG
3801 AGCTGGAGGC CAGCAACCTT GAGCTGGCCA AGGGCTACTG CCAGCGCGCC
3851 TACGCTCTGG ACCGCACAGA CAAGCAGCTG TTTTTGATCT GGCCGCGTGT
3901 GGAGGCGGGA CTGGGCGACC GCGACAAGGC GCGATTGCTG TTCGAGCGCG
3951 CACTGGACGC GCACCCGCTT AACACCAAGA TCATCAACAT GTACGCTCGC
4001 TTTGAGGCAG AGGAGGGATC CTACCGCGAA GCGGCAGAGC TGTACGACAG
4051 GGCGCTGCAA ATCGACCCAC TGTCGCCCGG CCCCGGCGTG CACAACCGCG
4101 CGGACTGGGC TTCCATGGAG ACCGACCTGG GGAACACAGG CCTGGCGCGG
4151 CAGCTGCTGG AGGAGGGGCT GGAGGCGCAC CCCAACAGCG CCGCACTGCT
4201 GGTCGTGTAC AGCAAGCTGC AGAGGCTGGA GGGCAGGTAC CAGGAGGCTC
4251 TGGCGGCTGT GCGGCGGGCG CAGGCGGTGG CGGGCGCGTT CAATGCTGCG
4301 GTCATGAATG AGCGGGCACA GGTGCTGCGT GCGCTGGGCG AGCGCGAACT
4351 GGCCGCCAAC CTGTCGCGCC ACGTGTCAGC CGTGAAACAG CTCAACCGAA
4401 TGAAGCAGCA GGGCTACTGG GGCTCAGAGG CCTGGAGGGC GTTCGTGGAG
4451 GCCACACGCA CCCCAGAGCA GCGTACCCTG GTGGCGGCGG CGCGGGCGCA
4501 CCGCCTGCAG CTGGGCTGGG CGCCGGCGGT GCGCGGCGCA AAGCCGGGGC
4551 CGCCGCCGGG CGTGGTGGCG GGCGACGGGC GGCGCCCGGC GGCGCCGGAG
4601 ACGCAGCAGT GGATGGCGCT GGAGGAGTTG CGTCGGCAGC GCGCGGAAGC
4651 GCGACGGCTG ACGGCGCAAC GCACGGCGCG ACTGCGGGCG GAGGAGGCGG
4701 CAGCCGCCGC CGGTGGTGGT GAGGCGGGTG CCGCCGCCGC GGCGGCGGCG
4751 CTGGCGATGG GCTCCACTGG ATCCATGGGA AGCATGGACG GCGATGAGGG
4801 CTACGATGAC GAGATCCAGG ATCCTGTGAT GTACGGCGCG GATCTTGGAT
4851 CCGGGCCATT GCCACGGAGG CGGTTGGAGG ACCAGGACGC GGATTATTAT
4901 GAGGAGCCTG AATCCATGGC GCTGCCGCCT CTGGATGCAG TGCGCCGCCC
4951 CATGCCCGAT GCCGACGACA TGGATCTCAT GCGCGGCTCC CACCACCACC
5001 ACCACCACCT CGGCGAGCAG AAGCTGATCT CCGAGGAGGA CCTGGGTAAC
5051 CGATACCCCT ACGACGTGCC CGACTACGCC TACCCCTACG ACGTGCCCGA
5101 CTACGCCGAT CGATCCGGAC CGTACCCCTA CGACGTGCCC GACTACGCCG
5151 CTAGCAGTAC TCGCCGGCCC CCCGACAGGC CTCCCCGTAA CCTGGTCATC
5201 GGAGGAGGTG CCAGGCTTCC GACGGCCGGC GTTAGCGCAT TTGTATGCAT
5251 GAGCGCGGTT GTTTACATGC TGGTGGGCGT GGTGCGCGGG GGGCCGGCGG
```

FIG 11B

```
5301 CGTCGGGTGC TGGTGTGGTG TGCTAGTTTT AGCCAGCATA CCGTACACTC
5351 CTGGCGGCCA ACTCGAGTTG TAGCTTGAAT GCATATGCAG ACAGGAAGGC
5401 AGTTGTGTGA GGTGGGGGGC GGACAGCGTA ATGGAGTACC GTCAGTAAGA
5451 GGATGGAGTC ACGGAGCATG TGCTAGAATG TTCCTGAGTG CTGCATGAAC
5501 TGGCTACTGC CTTGGGGAGT CGACCGCGCC TGCGGTGGTT GGGTCAGTCT
5551 CAGCAATTTC AGGTGGGTGA TGAGACGATG AGCTCTAATG CATATTATCG
5601 TATGCGCTGC TGCCTGCGCA CTCTCGCTGT GTGAGAGGAG GGCTACAGTA
5651 GGCTAGGCCG TGTAGGGCGT GCAGGCAACA CAAGAGAGCC AGTCAAGCAG
5701 AGAGAGAGAG GGAGGGGGCA GGTGTTGCAG TGAGAACTGG AATCGTGTCG
5751 CAGACAGATT GCAAGGCGTA GTCCCACGGC GGCTATCTGC ACACAGAGCT
5801 GCCGTGTGAC ATGTGCAAAA GGGCGTGAGG AGATGGCAGT GGCTGTAACA
5851 AGAACAAAGA GCGGCCGCGA ATTCGATATC AAGCTTATCG ATA
```

Fig. 11C

```
   1 CTCGAGCAGA GGTTGGGAAT CGCTTTGAAA ATCCAGCAAT CGGGTCTCAG
  51 CTGTCTCAGG CCGCACGCGC CTTGGACAAG GCACTTCAGT AACGTACTCC
 101 AAGCCCTCTA TCTGCATGCC CACAAAGCGC AGGAATGCCG ACCATCGTGC
 151 CAGACTGTGC CGCGCCCGAA CCGAAATCCG TCACTCCCCT TGGTTCCCAT
 201 GGTGGCATGG TCCCCCCTGT TCGCCCAAAG CCTGGTTCAG CGCCCAGTGG
 251 CAAACGGCTT TGGCTCAGCT CCTTGGTATT GCTGGTTTCT AGCAATCTCG
 301 TCCGTTCCTC TGTTGCCAAT GTAGCAGGTG CAAACAGTCG AATACGGTTT
 351 TACTCAGGGG CAATCTCAAC TAACAGAGGC CCTGGGCCTG TTGCCTGGAA
 401 CCTATGAAGA CGATAATGCC ACGGCGACTT TCGAGCCTGA GGGAAGTTTG
 451 CACCGGTACC GCATTGTGCA AGGTTACGGT ACATGATAGG GGGAGTGCGA
 501 CGC*GGTAAGG* *CTTGGCGCAG* *CTTGGCGCGT* *CTGCCTTGCA* *TGCATGTCCG*
 551 *AAACACGCCA* *CGTCGCGCCA* *CGAAAAGCGG* *TAAAAGGACC* *TGCCATGGTC*
 601 *CTCCAGGGTG* *TTACCACTTC* *CATTTCGCTC* *AGCTGGGATG* *GTGCTCGTAG*
 651 *GTGCACCAGC* *GTTGATTATT* *TCAGGCAGGA* *AGCGGCTGCG* *AAGCCCGCCT*
 701 *TTCACTGAAG* *ACTGGGATGA* *GCGCACCTGT* *ACCTGCCAGT* *ATGGTACCGG*
 751 *CGCGCTACCG* *ATGCGTGTAG* *TAGAGCTTGC* *TGCCATACAG* *TAACTCTGGT*
 801 *ACCCCAGCC* *ACCGGGCGTA* *GCGAGCAGAC* *TCAATAAGTA* *TGATGGGTTC*
 851 *TTATTGCAGC* *CGCTGTTACA* *GTTACAGCG* *CAAGGGAACA* *CGCCCCTCAT*
 901 *TCACAGAACT* *AACTCAACCT* *ACTCCATC*ca tatg CTTCAG TTGGCGAACC
 951 GTAGCGTGAG GGCTAAGGCC GCTCGTGCCA GCCAAAGCGC TCGGAGTGTC
1001 TCGTGTGCGG CTGCCAAGCG CGGTGCGGAT GTTGCTCCCC TGACGTCGGC
1051 CCTGGCGGTC ACCGCATCCA TCCTGCTCAC GACTGGCGCG GCGAGCGCTA
1101 GCGCAGCTGA CCTCGCTCTC GGCGCCCAGG TCTTCAACGG CAACTGTGGT
1151 GAGTAGCTCA TGCAAATTTA GCATGATCGA AGGCTGCGCG TGTCATGGGT
1201 CTCCGCTCGC TGTTCGACAT GCCGTTTCGC TCAACTGCAC CATCGACTAT
1251 CGGTCCCCCT CCTTCCACTT CTGGCCCACG CAGCCGCGTG CCACATGGGC
1301 GGTCGCAACA GCGTGATGCC CGAGAAGACG CTGGACAAGG CCGCCCTTGA
1351 GCAGTACCTG GATGGCGGCT TCAAGGTGGA GAGCATCATC TATCAGGTCG
1401 GGACATCCCC GACCAGGGGC GGCGGGGATG TTGCTGGGCC GATGGAAAGT
1451 AGCAACCCAG CCAGCGGCTT CCAGCGCACT CCAGCTGCTC ACGGTTGCGA
1501 CATTGCGCGT GCACGCTTGC GCGTCCCTCA CTCGGCCAGC TTGTCGCCGC
1551 AGACATCCCT AGCATTGTGC GGACTGCGGT CGTCAGTTAG CGTAGTGGCG
1601 GGGCTCAAAG CGTGATGCAG CTGGTGGCTG ATTGCATGTG CTACATATGC
1651 TGTTATGTTT TGCATGAACT TCGATGCATT GGATGCTGGG TGCACGCGTT
1701 TGCATGTGTT TGTGCCGGCA TGCTGCCGTC GTCGGCCGTA CGTTACGTT
1751 TCTGTGTGCC GGGGTCTTTA TTTCCGCCTG CAGGTGGAGA ATGGCAAGGG
1801 GGCGATGCCG GCGTGGGCGG ATCGGCTGTC GGAGGAGGAA ATCCAGGCTG
1851 TGGCGGAGTA CGTGTTCAAG CAGGCCACGG ATGCCGCCTG GAAGTACTAG
1901 GTTGATGTTG TTATTTCAAC TGGGTCACCG TAGCTAGCTC GTGCCCCAGT
1951 TGTGGATGCG AGTTATACGT CATTGCGTAA CATGTTCATG ATAGACTGCA
2001 TTAGGTAGGC GTCGTGTGTG AGCACATACA GAAGTCATCA CGCAAATGGA
2051 CACGTTCCGG CGAACCCGAG GGGAAAGGCT TGGGCCAGTA CATTATTTCA
2101 ACACTAAAAT ATGTAACATA ATGGAACTTG AGCACGGTCC GGGAGCGCAG
2151 GCTGGGCTTG GGGGTCGCGG CTCGAGGGAG AGGGGCGACG TTGGGGCAGG
2201 TCGGGCTTC AACCGGGTTT TGCACGGCCG AACCATGAAC GCGCTTTGGC
2251 CAGCCAAGAT ACTGAAAATA CAACAGAAGG ATATCCAGTA TGTAGCAAAG
2301 CCTTCAAACA GCGTGTACAA GCAAGCCTGT GACAAAGCGG ACCCGGCCGT
2351 GAAGTCCACG GTATTTCCTC AAGCAGCATT CAGATGAGAG AAGGAATGGG
2401 CTCTCCATCT GTTTACATTC AGTCGCATTC CACTTGTCCT GGCGCATCGT
2451 CTGTCGCTAG ACGTCGCCGC TCAAAGCGTT TTCGCGGTGG CAGCACCGGC
2501 TAAGAACCGA AGGCGATCGC AGTCCATTTT CCTGACGTTG GACGCTTTGA
2551 GGGCACGAGG CGATGGCTGC GGGCTGCGGG CTGCATGGTT GTTTCCGGAG
2601 CAGAGTC
```

```
  1 GAGTCATATG AAATTAAATG GATATTTGGT ACATTTAATT CCACAAAAAT
 51 GTCCAATACT TAAAATACAA AATTAAAAGT ATTAGTTGTA AACTTGACTA
101 ACATTTTAAA TTTAAATTT  TTCCTAATT  ATATATTTA  CTTGCAAAAT
151 TTATAAAAAT TTTATGCATT TTATATCAT  AATAATAAAA CCTTTATTCA
201 TGGTTTATAA TATAATAATT GTGATGACTA TGCACAAAGC AGTTCTAGTC
251 CCATATATAT AACTATATAT AACCCGTTTA AAGATTATT  TAAAAATATG
301 TGTGTAAAAA ATGCTTATTT TTAATTTTAT TTATATAAG  TTATAATATT
351 AAATACACAA TGATTAAAAT TAAATAATAA TAAATTTAAC GTAACGATGA
401 GTTGTTTTTT TATTTTGGAG ATACACGCAA TGACAATTGC GATCGGTACA
451 TATCAAGAGA AACGCACATG GTTCGATGAC GCTGATGACT GGCTTCGTCA
501 AGACCGTTTC GTATTCGTAG GTTGGTCAGG TTTATTACTA TTCCCTTGTG
551 CTTACTTTGC ATTAGGTGGT TGGTTAACTG GTACTACTTT CGTTACTTCA
601 TGGTATACGC ATGGTTTAGC TACTTCTTAC TTAGAAGGTT GTAACTTCT T
651 AACAGCAGCT GTTTCTACAC CTGCTAACAG TATGGCTCAC TCTCTTCTAT
701 TTGTTTGGGG TCCAGAAGCT CAAGGTGATT TCACTCGTTG GTGTCAACTT
751 GGTGGTTTAT GGGCATTCGT TGCTTTACAC GGTGCATTTG GTTTAATTGG
801 TTTCATGCTT CGTCAGTTTG AAATTGCTCG TTCAGTAAAC TTACGTCCAT
851 ACAACGCAAT TGCTTTCTCA GCACCAATTG CTGTATTCGT TTCAGTATTC
901 CTAATTTACC CATTAGGTCA ATCAGGTTGG TTCTTTGCAC CTAGTTTCGG
951 TGTAGCTGCT ATCTTCCGTT TCATTTTATT CTTCCAAGGT TTCCACAACT
1001 GGACACTTAA CCCATTCCAC ATGATGGGTG TTGCTGGTGT TTAGGTGCT
1051 GCTTTATTAT GTGCTATTCA CGGTGCTACT GTTGAAAACA CATTATTCGA
1101 AGACGGTGAC GGTGCTAACA CATTCCGTGC ATTCAACCCT ACACAGGCTG
1151 AAGAAACATA CTCTATGGTT ACTGCTAACC GTTTCTGGTC ACAAATCTTC
1201 GGTGTTGCTT TCTCTAACAA ACGTTGGCTT CACTTCTTCA TGTTATTAGT
1251 TCCAGTAACT GGTCTTTGGA TGAGTGCTAT TGGTGTTGTA GGTTTAGCTC
1301 TAAACTTACG TGCTTACGAC TTCGTATCAC AAGAGATTCG TGCTGCTGAA
1351 GACCCTGAAT TCGAAACATT CTACACTAAA AACATTCTTC TTAACGAAGG
1401 TATTCGTGCT TGGATGGCTG CTCAAGACCA ACCACACGAA CGTTTAGTAT
1451 TCCCTGAAGA AGTATTACCA CGTGGTAACG CTCTATAATA TATTTTTATA
1501 TAAATTACCA ATACTAATTA GTATTGGTAA TTTATATTAC TTTATTATTT
1551 AAAAGAAAAT GCCCCTTTGG GGCTAAAAAT CACATGAGTG CTTGAGCCGT
1601 ATGCGAAAAA ACTCGCATGT ACGGTTCTTT AGGAGGATTT AAAATATTAA
1651 AAAATAAAAA AACAAATCCT ACCTGACTAA ACCAGGACAT TTTTCACGTA
1701 CTCTGTCAAA AGGTCC
```

SYSTEM, METHOD, AND DEVICE FOR THE EXPRESSION OR REPRESSION OF PROTEINS

CROSS REFERENCE TO RELATED APPLICATIONS

This application is a continuation application of U.S. application Ser. No. 12/377,238, filed Feb. 11, 2009, which is U.S. national application under 37 C.F.R. § 371(b) of International Application Serial No. PCT/US2007/017774, filed Aug. 11, 2007, which claims priority under 35 U.S.C § 119(e) to U.S. Provisional Application Ser. No. 60/837,001, filed on Aug. 11, 2006, each of which is incorporated herein by reference.

This application also comprises a sequence listing in electronic form which is incorporated herewith in its entirety.

FIELD OF THE INVENTION

This invention relates to systems, methods, and devices for inducing andlor repressing the expression of proteins. More particularly, the invention relates to systems, methods, and devices for inducing andlor repressing the expression of proteins in plastids.

BACKGROUND AND SUMMARY OF THE INVENTION

Proteins (e.g., peptides, oligopeptides, and polypeptides) are responsible for most of the activities of a cell, such as catalysis, communication, defense, movement, and transport. The underlying basis of a protein's biological activity is its amino acid sequence andlor its conformation. Accordingly, the biologically active portion of a protein should remain essentially intact and in its biologically functional conformation. The advancements in genetic engineering techniques for protein expression have led to the development of methods for the controlled expression of both native and foreign proteins in various systems in a form that maintains the biological activity of the proteins. Such genetically engineered, controlled expression systems can result in higher protein yield due to the expression of properly-folded, stable proteins where inactivation and degradation of the proteins is reduced as a result of the ability to control protein expression.

Although a number of different types of expression systems have been developed, in various organelles of host cells such as microorganisms, eukaryotic cells, including fungi, yeast, and mammalian cells, insect cells, etc., an expression system for the controlled expression of proteins utilizing stability factors of nuclear origin to regulate the expression of proteins in plastids has not previously been developed. Plastids are organelles responsible for photosynthesis and are commonly classified as chloroplasts, leucoplasts, amyloplasts, or chromoplasts. Plastids can differentiate or redifferentiate between these forms.

In one embodiment, a method for preparing an expression system for inducing the production of a protein in the plastid of a cell is provided. The method comprises the steps of introducing a first nucleic acid into the nucleus of a cell wherein the first nucleic acid encodes an inducible promoter, operatively linking the first nucleic acid to a second nucleic acid to form a recombinant nucleic acid wherein the second nucleic acid encodes a stability factor, wherein the introduction of an inducer or the removal of a repressor induces the expression of the stability factor, wherein the expressed stability factor associates in the plastid with an untranslated region of an mRNA stabilized by the stability factor and transcribed from a third nucleic acid, wherein the third nucleic acid is either native to the plastid or is foreign to the plastid and wherein the third nucleic acid encodes the protein, and wherein expression of the mRNA results in the production of the protein.

In another illustrative embodiment, a method for preparing an expression system for repressing the expression of a plastid protein in the plastid of a cell is provided. The method comprises the steps of introducing a first nucleic acid into the nucleus of a cell wherein the first nucleic acid encodes a repressible promoter, operatively linking the first nucleic acid to a second nucleic acid to form a recombinant nucleic acid wherein the second nucleic acid encodes a stability factor, wherein the introduction of a repressor or the removal of an inducer represses the expression of the stability factor, and wherein the repression of the expression of the stability factor results in the repression of expression of an mRNA stabilized by the stability factor and transcribed from a third nucleic acid, wherein the third nucleic acid is either native to the plastid or is foreign to the plastid and wherein the third nucleic acid encodes the protein, and wherein the expression of the protein is repressed.

In still another illustrative aspect, a method for expressing a plastid protein in the plastid of a cell is provided. The method comprises the steps of contacting the cell with an inducer or treating the cell under conditions that result in the removal of a repressor, wherein the inducer or the repressor associates with a first nucleic acid in the nucleus, wherein the first nucleic acid encodes an inducible promoter, wherein the first nucleic acid is operatively linked to a second nucleic acid to form a recombinant nucleic acid and wherein the second nucleic acid encodes a stability factor, expressing the stability factor, introducing the stability factor into the plastid wherein the stability factor associates in the plastid with an untranslated region of an mRNA to stabilize the mRNA wherein the mRNA is transcribed from a third nucleic acid which is either native to the plastid or is foreign to the plastid and wherein the third nucleic acid encodes the protein, expressing the mRNA, and producing the protein in the plastid.

In another embodiment, a method for repressing the expression of a plastid protein in the plastid of a cell is provided. The method comprises the steps of contacting the cell with a repressor or treating the cell under conditions that result in the removal of an inducer, wherein the repressor or the inducer associates with a first nucleic acid in the nucleus of the cell, wherein the first nucleic acid encodes a repressible promoter, wherein the first nucleic acid is operatively linked to a second nucleic acid to form a recombinant nucleic acid, and wherein the second nucleic acid encodes a stability factor, repressing the expression of the stability factor wherein the stability factor associates in the plastid with an untranslated region of an mRNA to stabilize the mRNA wherein the mRNA is transcribed from a third nucleic acid which is either native to the plastid or is foreign to the plastid and wherein the third nucleic acid encodes the protein, repressing the expression of an mRNA, and repressing the expression of the protein.

In still another embodiment, a system for expressing a plastid protein in the plastid of a recombinant host cell is provided. The system comprises an exogenously added inducer that induces the expression of a nuclear protein, the recombinant host cell wherein the nucleus of the recombinant host cell comprises a recombinant nucleic acid, wherein the recombinant nucleic acid comprises a first nucleic acid operatively linked to a second nucleic acid to form the recombinant nucleic acid, wherein the first nucleic acid encodes an inducible promoter and wherein the second nucleic acid encodes a stability factor, and the plastid comprising a third nucleic acid that is either native to the plastid or foreign to the plastid wherein the third nucleic acid encodes the expressed plastid protein wherein the expression of the mRNA encoding the plastid protein is controlled by the stability factor.

In another illustrative embodiment, a system for repressing the expression of a plastid protein in the plastid of a recombinant host cell is provided. The system comprises an exogenously added repressor that represses the expression of a nuclear protein, the recombinant host cell wherein the nucleus of the recombinant host cell comprises a recombinant nucleic acid, wherein the recombinant nucleic acid comprises a first nucleic acid operatively linked to a second nucleic acid to form the recombinant nucleic acid, wherein the first nucleic acid encodes a repressible promoter and wherein the second nucleic acid encodes a stability factor, and the plastid comprising a third nucleic acid that is either native to the plastid or foreign to the plastid wherein the third nucleic acid encodes the expressed plastid protein and wherein the expression of the mRNA encoding the protein is controlled by the stability factor.

In another embodiment, a method for stimulating the production of hydrogen gas by expressing a plastid protein in the plastid of a cell is provided. The method comprises the steps of contacting the cell with an inducer or treating the cell under conditions that result in the removal of a repressor, wherein the inducer or the repressor associates with a first nucleic acid in the nucleus, wherein the first nucleic acid encodes an inducible promoter, wherein the first nucleic acid is operatively linked to a second nucleic acid to form a recombinant nucleic acid and wherein the second nucleic acid encodes a stability factor, expressing the stability factor, introducing the stability factor into the plastid wherein the stability factor associates in the plastid with an untranslated region of an mRNA to stabilize the mRNA wherein the mRNA is transcribed from a third nucleic acid which is either native to the plastid or is foreign to the plastid wherein the third nucleic acid encodes the protein, expressing the mRNA, producing the protein in the plastid, and producing hydrogen gas.

In yet another embodiment, a method for inhibiting the production of hydrogen gas by repressing the expression of a plastid protein in the plastid of a cell is provided. The method comprises the steps of contacting the cell with a repressor or treating the cell under conditions that result in the removal of an inducer, wherein the repressor or the inducer associates with a first nucleic acid in the nucleus of the cell, wherein the first nucleic acid encodes a repressible promoter, wherein the first nucleic acid is operatively linked to a second nucleic acid to form a recombinant nucleic acid, wherein the second nucleic acid encodes a stability factor, repressing the expression of the stability factor wherein the stability factor associates in the plastid with an untranslated region of an mRNA to stabilize the mRNA wherein the mRNA is transcribed from a third nucleic acid which is either native to the plastid or is foreign to the plastid and wherein the third nucleic acid encodes the protein, repressing the expression of the mRNA, repressing the expression of the protein, and inhibiting the production of hydrogen gas.

In still another embodiment, a method for stimulating the production of hydrogen gas by inducing and repressing the expression of a plastid protein in the plastid of a cell is provided. The method comprises the steps of sequentially i) contacting the cell with an inducer or treating the cell under conditions that result in the removal of a repressor and ii) contacting the cell with the repressor or treating the cell under conditions that result in the removal of the inducer, wherein the inducer or the repressor associates with a first nucleic acid in the nucleus, wherein the first nucleic acid encodes an inducible promoter, wherein the first nucleic acid is operatively linked to a second nucleic acid to form a recombinant nucleic acid and wherein the second nucleic acid encodes a stability factor, sequentially expressing and repressing the expression of the stability factor, wherein the stability factor associates in the plastid with an untranslated region of an mRNA to stabilize the mRNA wherein the mRNA is transcribed from a third nucleic acid which is either native to the plastid or is foreign to the plastid wherein the third nucleic acid encodes the protein, sequentially expressing and repressing the expression of the mRNA, producing the protein in the plastid, and producing hydrogen gas.

In any of the above-described embodiments, the first nucleic acid can be operatively linked to the second nucleic acid to form the recombinant nucleic acid prior to introducing the recombinant nucleic acid into the nucleus, the cell can have an inoperative copy or can be missing a copy or a homolog of the second or the third nucleic acid, the cell can be a plant cell or an algal cell, the plastid can be selected from the group consisting of a chloroplast, a leucoplast, a amyloplast, an etioplast, an elaioplast, and a chromoplast, the inducible promoter can have at least 90% sequence similarity to the Cyc6 promoter, and the third nucleic acid can encode a gene that has at least 90% sequence similarity to the psbD gene.

In any of the above-described embodiments, the inducer or repressor can be a chemical or an environmental condition where the chemical can be copper and where the environmental condition can be reduction in the concentration of oxygen to a predetermined level, the inducer can be applied and removed for a plurality of cycles wherein a cycle comprises applying and removing the inducer, the protein can be a protein involved in photosynthesis or in the production of hydrogen gas, the protein can be selected from the group consisting of a pharmaceutical agent, an industrial enzyme, an enzyme involved in chloroplast maturation or degradation, and a nutraceutical where the pharmaceutical agent is selected from the group consisting of an antibody, a vaccine antigen, and an antimicrobial agent, or other defense products for the host cell and the stability factor can be selected from the group consisting of Nac2 and Mbb1. In another illustrative embodiment, the second nucleic acid can code for a translational activating factor, such as, for example, Tbc2 or Tca1.

In another embodiment of the invention, a system and method for regulating the expression or repression of native or foreign genes in plastids is provided. In one embodiment, the invention relates to an expression system employing a nuclear-encoded chloroplast transcription factor, Nac2, the expression of which is regulated by an inducible promoter of the Cyc6 gene. In another embodiment, induction of Nac2 expression by an inducer (i.e., an agent or alteration of an environmental condition), such as low levels of oxygen, causes the expression of the psbD gene in the chloroplast. In yet another embodiment, an agent or environmental condition, such as removal of copper, that causes induction of the Cyc6 promoter, also causes expression of the psbD gene. In another illustrative embodiment, repression of the Nac2 gene by a repressor (i.e., an agent or alteration of an environmental condition), such as high levels of oxygen, results in no or reduced expression of the psbD gene. In a related embodiment, an agent or alteration in an environmental condition that represses the inducible Cyc6 promoter also causes reduced expression of the psbD gene.

In other illustrative embodiments, the invention relates to the inducible expression of or the repression of a foreign gene in the chloroplast whereby replacement of the psbD gene in the chloroplast with a foreign gene facilitates inducible expression of or the repression of the foreign gene in the chloroplast by regulation of Nac2 expression.

In another embodiment, the invention relates to a method of producing hydrogen gas in the chloroplast through regulation of the psbD gene by Nac2 expression or repression of expression of Nac2. In this illustrative aspect of the invention, environmental conditions that facilitate the induction and repression of the Nac2 gene (e.g., reducing the level of oxygen to induce expression and elevating the level of oxygen to repress expression), resulting in the oscillating induction and repression of psbD gene expression, result in a reduction in the rate of photosynthesis and a resulting reduction in the concentration of oxygen. In this embodiment, the reduction in the concentration of oxygen facilitates the production of hydrogen. Thus, in one embodiment, the invention relates to a method of producing hydrogen gas by regulating the oscillating induction and repression of Nac2 and psbD gene expression.

In yet another embodiment, the invention relates to a method for enhancing the hydrogen-generating system through the recombinant expression of other genes in the chloroplast, for example, hydrogenases and repression of other recombinant or native proteins, such as phosphoribulose kinase.

In still another embodiment an apparatus for the production of hydrogen is provided. The apparatus comprises a first vessel configured to hold a cell culture in a substantially oxygen-depleted environment, a first pump in fluid communication with the first vessel and configured to pump a medium into the first vessel at a predetermined rate, and a measuring device coupled to the first vessel and configured to measure an amount of hydrogen produced by the cell culture.

In this embodiment, the first pump can be configured to pump the amount of medium into the first vessel at a rate substantially equal to the rate of growth of the cell culture, the first pump can comprise a peristaltic pump, the cell culture can comprise a cy6Nac2.49 culture, the measuring device can comprise a mass spectrometer, the apparatus can further comprise an agitation device coupled to the first vessel and operable to agitate the cell culture, the agitation device can comprise a magnetic stir bar, the apparatus can further comprise a second vessel configured to hold an amount of the medium, wherein the first pump is fluidly coupled to the second vessel and configured to pump the medium from the second vessel at the predetermined rate, the apparatus can further comprise a third vessel in fluid communication with the first vessel and configured to hold an overflow of the medium from the first vessel, and the apparatus can further comprise a filter and a second pump in fluid communication with the third vessel and the second vessel, the second pump being configured to pump an amount of the medium from the third vessel, through the filter, and into the second vessel.

BRIEF DESCRIPTION OF THE DRAWINGS

The present invention may be more readily understood by reference to the following figures wherein:

FIGS. 11 *a-c* show the genomic sequence of the Nac2 midi gene and is depicted as Seq ID. 10. The initiation codon is the first underlined ATG. The putative transit peptide is also underlined.

FIG. 12 shows the Cyc6 genomic sequence and is depicted as Seq ID. 11. The genomic sequences used to generate the fusion construct with the Nac2 midi gene are underlined. Also indicated (double-underlining) is the three base-pair difference in the cyc6Nac2 construct that created an NdeI restriction site.

FIG. 18 shows a map of the chloroplast expression plasmid pcg12 IBDV Flag.

FIG. 20 shows the chloroplast DNA sequence of psbD and is depicted as Seq ID. 12. The underlined sequences were used to drive the expression of genes in the chloroplast using the cyc6Nac2 system.

DETAILED DESCRIPTION OF THE ILLUSTRATIVE EMBODIMENTS

Figure 1:
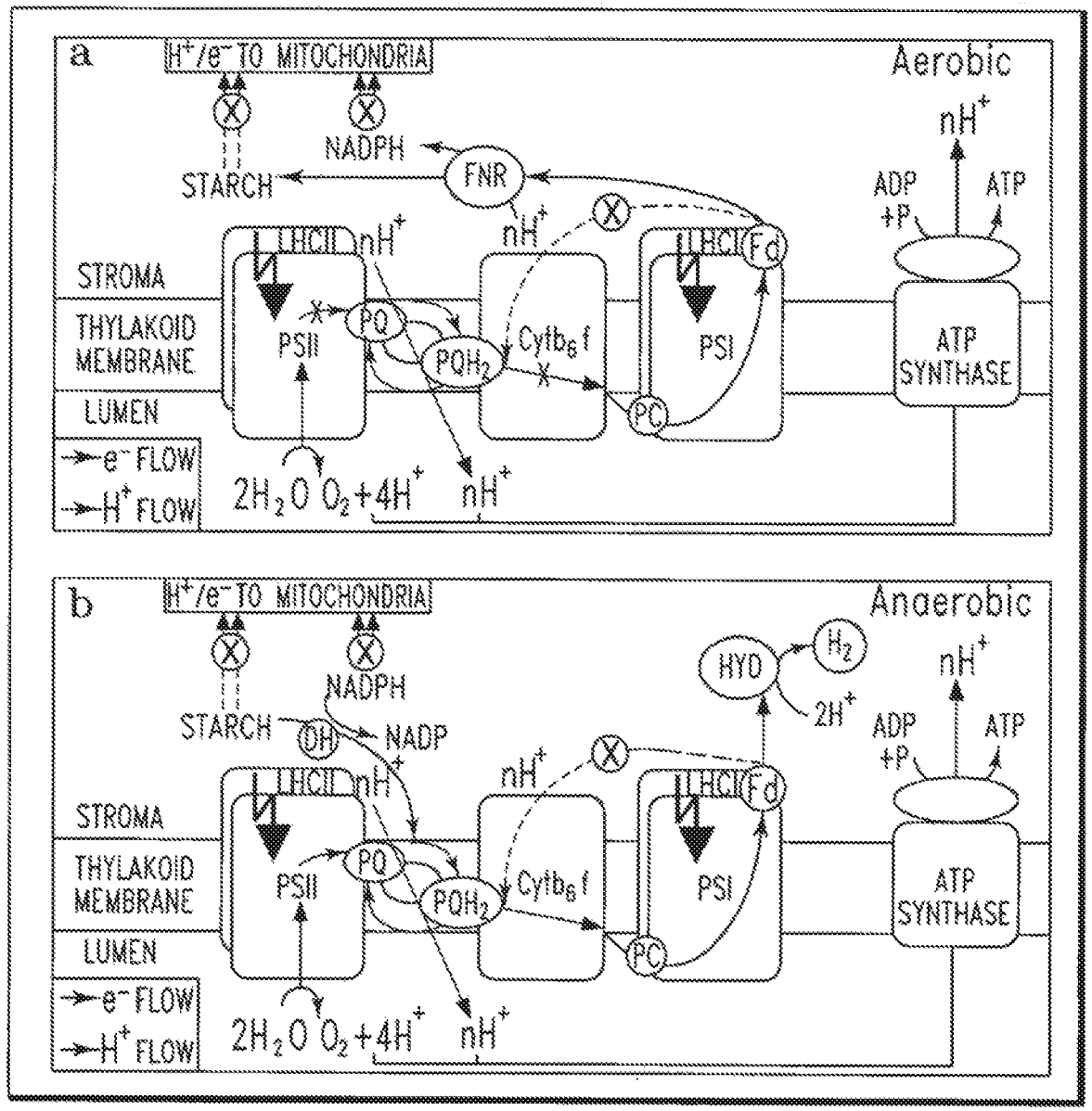
FIG. 1 shows a diagram of hydrogen and electron flow in the chloroplast of *C. reinhardtii* under aerobic and anaerobic conditions (from Kruse et al., 2005).
Figure 2:
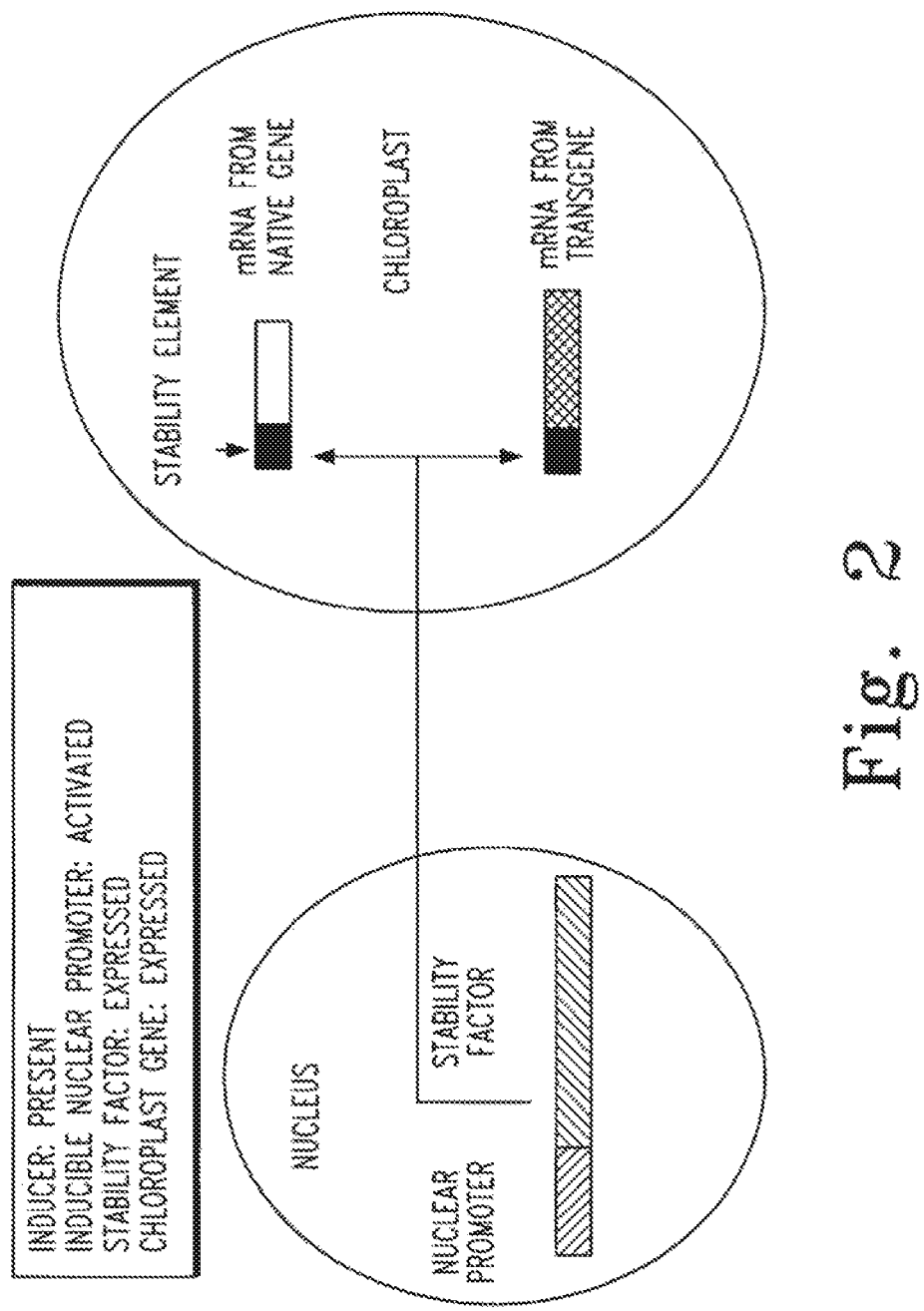
FIG. 2 shows a schematic outline of a plastid gene regulation system in which the nuclear inducible promoter is induced in the presence of an inducer. The left-hatched box represents the nuclear inducible promoter and the right-hatched box represents the gene for the stability factor. The filled box represents the stability factor association element, in this embodiment located in the 5' untranslated region of the plastid mRNA. The open box represents an mRNA produced from a plastid native gene. The cross-hatched box represents an mRNA produced from a foreign gene in the plastid.

As used herein, the phrase "foreign gene" or "foreign nucleic acid" (i.e., a transgene) means any nucleic acid inserted into a nucleic acid of a cell using recombinant DNA technology where the foreign gene or foreign nucleic acid is not normally present in that location in the cell. A foreign gene or foreign nucleic acid can include coding and non-coding nucleic acid sequences. A foreign gene or foreign nucleic acid can comprise a native nucleic acid that has been modified using recombinant DNA technology and has been reintroduced into the cell, or can comprise a native nucleic acid moved from one location to another within the cell.

As used herein, the phrase "native nucleic acid" or "native gene" means a nucleic acid that has its natural sequence (including naturally occurring mutations) and location in a cell.

As used herein, the term "inducible" means a promoter capable of being regulated so that mRNA transcripts are produced. Methods for determining the level of mRNA transcripts include Northern blotting and real-time PCR.

As used herein, the term "expression" can mean transcription of DNA into RNA or translation of RNA into protein.

As used herein the phrase "stability factor" means a nuclear protein that can exhibit activities, including, but not limited to, transcriptional, post-transcriptional, translational, post-translational, protein targeting, and protein recruitment activities, to enhance the expression or activity of a chloroplast protein.

The invention relates to systems, methods, and devices for the regulation of expression of a gene in the plastid of a cell (e.g., an algal or plant cell) for the purpose of producing useful products. The induction or repression of gene expression in the plastid is accomplished by transforming the nuclear genome of the cell with an inducible or repressible promoter operatively linked to a gene which codes for a chloroplast-targeted protein. The chloroplast-targeted protein associates, directly or indirectly (e.g., through accessory proteins), with an untranslated region of a plastid-expressed mRNA. The chloroplast-targeted protein is required for stability andlor translation of the plastid-expressed mRNA and hence expression of the plastid gene.

In one embodiment, the nuclear promoter is an inducible promoter and the addition or removal of a chemical (e.g., copper, a carbohydrate, or a protein) compound or an alteration in an environmental condition (e.g., low oxygen concentration, or an alteration in light, temperature, or nutritional status) activates the promoter resulting in expression of the chloroplast mRNA, and subsequently, the expression of the protein coded by the mRNA. In another embodiment, the nuclear promoter is a repressible promoter and the addition or removal of a chemical compound (e.g., copper, a carbohydrate, or a protein) or an alteration in an environmental condition (e.g., high oxygen concentration, or an alteration in light, temperature, or nutritional status) represses the promoter resulting in lack of expression of stability factor and inhibition of expression of the chloroplast mRNA, and subsequently, the expression of the protein coded by the mRNA.

In one embodiment, the invention relates to a method for expressing a protein in the plastid of a cell. The method comprises the steps of contacting the cell with an inducer or treating the cell under conditions that result in the removal of a repressor, wherein the inducer or the repressor associates with a first nucleic acid in the nucleus, wherein the first nucleic acid encodes an inducible promoter, wherein the first nucleic acid is operatively linked to a second nucleic acid to form a recombinant nucleic acid and wherein the second nucleic acid encodes a stability factor, expressing the stability factor, introducing the stability factor into the plastid wherein the stability factor associates in the plastid with an untranslated region of an mRNA to stabilize the mRNA wherein the mRNA is transcribed from a third nucleic acid which is either native to the plastid or is foreign to the plastid and wherein the third nucleic acid encodes the protein, expressing the mRNA, and producing the protein in the plastid.

In another embodiment, a method for repressing the expression of a plastid protein in the plastid of a cell is provided. The method comprises the steps of contacting the cell with a repressor or treating the cell under conditions that result in the removal of an inducer, wherein the repressor or the inducer associates with a first nucleic acid in the nucleus of the cell, wherein the first nucleic acid encodes a repressible promoter, wherein the first nucleic acid is operatively linked to a second nucleic acid to form a recombinant nucleic acid, and wherein the second nucleic acid encodes a stability factor, repressing the expression of the stability factor wherein the stability factor associates in the plastid with an untranslated region of an mRNA to stabilize the mRNA wherein the mRNA is transcribed from a third nucleic acid which is either native to the plastid or is foreign to the plastid and wherein the third nucleic acid encodes the protein, repressing the expression of an mRNA, and repressing the expression of the protein.

In the above-described embodiments, the protein is expressed in the plastid of a cell. Illustratively, the cells can be cells of plants or algal cells or any cell type that contains a plastid. Plastids are organelles that contain a plastid genome, often in multiple copies. Plastids are found in, for example, plants and algae and include chloroplasts, leucoplasts, amyloplasts, etioplasts, elaioplasts, and chromoplasts.

In the method and system embodiments described herein, the third nucleic acid encodes the protein of interest. In one illustrative embodiment, the third nucleic acid, coding for the expressed protein, can be either native to the plastid or foreign to the plastid (i.e., a transgene). In this embodiment, the expressed protein (e.g., a peptide, an oligopeptide, or a polypeptide) can be expressed under the control of an inducible or repressible promoter and includes proteins involved in photosynthesis, such as components of Photosystem I or II (e.g., psbA and psbD and the D1 and D2 subunits of Photosystem II), proteins involved in $CO_2$ fixation (e.g., phosphoribulose kinase), hydrogenases (e.g., HydA1 and HydA2), and proteins that regulate the activity of any of these proteins (e.g., the assembly of any these proteins (e.g., HydEF and HydG)), or any other proteins that are native to the plastid. Exemplary native proteins that can be expressed under the control of an inducible or repressible promoter include any of the proteins involved in the regulation of the photosynthetic processes or carbon assimilation processes depicted or implied in FIG. 1 or any other protein native to the plastid. In an alternate embodiment, an amino acid, such as an aromatic amino acid, or an amino acid precursor can be produced by regulating the expression of proteins native to the plastid that are involved in the synthetic pathways for amino acids, such as aromatic amino acids.

In another illustrative embodiment, a protein involved in the production of hydrogen gas can be expressed under the control of an inducible or repressible promoter, or both, using the methods, systems, and devices described herein. In this embodiment, proteins involved in the production of hydrogen gas can be any proteins described in this or the preceding paragraph, or can be any of the proteins which are involved in the regulation of the photosynthetic processes or carbon assimilation processes depicted or implied in FIG. 1. In this embodiment, the inducer or repressor can be applied and removed for a plurality of cycles, wherein a cycle comprises applying and removing the inducer or repressor.

In another embodiment, the third nucleic acid, coding for the expressed protein, can be foreign to the plastid (i.e., a foreign nucleic acid or a foreign gene). In this embodiment, the protein can be a pharmaceutical agent, an industrial enzyme, an enzyme involved in chloroplast maturation or degradation, or a nutraceutical. In this embodiment, the expressed protein can be, for example, an antibody, a vaccine antigen (e.g., for use in a vaccine), an antimicrobial agent, or other defense products for the host cell, a growth hormone, a cytokine, such as an interleukin or an interferon, insulin, colony-stimulating factors, coagulation factors, erythropoietins, growth factors, such as epidermal growth factor, somatotropin, fibroblast growth factor, platelet-derived growth factor, and the like, amylases, proteases, lipases, pectinases, cellulases, hemicellulases, pentosanases, xylanases, and phytases, insecticidal proteins, phenyl ammonia lyase, or any other pharmaceutical agent, industrial enzyme, or nutraceutical that is proteinaceous.

In yet another illustrative embodiment, additional nucleic acids (e.g., a fourth nucleic acid, etc.) coding for an expressed protein, can be expressed in the chloroplast and can be native or foreign to the plastid (i.e., a foreign nucleic acid or a foreign gene). In these embodiments, the expression of the additional nucleic acids can be controlled by their own stability factors coded by additional nucleic acids in the nucleus (i.e., similar to the second nucleic acid) or the expression of these additional nucleic acids can be controlled by the stability factor encoded by the second nucleic acid. In one illustrative embodiment, one stability factor associates with the stability factor association element in plastid mRNA and stimulates expression of the third nucleic acid and additional nucleic acids (e.g., the fourth nucleic acid, etc.) operatively linked to the third nucleic acid. In these embodiments, the protein expressed can be a pharmaceutical agent, an industrial enzyme, an enzyme involved in chloroplast maturation or degradation, or a nutraceutical. In this embodiment, the expressed protein can be, for example, an antibody, a vaccine antigen (e.g., for use in a vaccine), an antimicrobial agent, or other defense products for the host cell, a growth hormone, a cytokine, such as an interleukin or an interferon, insulin, colony-stimulating factors, coagulation factors, erythropoietins, growth factors, such as epidermal growth factor, somatotropin, fibroblast growth factor, platelet-derived growth factor, and the like, amylases, proteases, lipases, pectinases, cellulases, hemicellulases, pentosanases, xylanases, and phytases, insecticidal proteins, phenyl ammonia lyase, or any other pharmaceutical agent, industrial enzyme, or nutraceutical that is proteinaceous.

In the embodiment where the expressed protein is a vaccine antigen for use as a vaccine, the expressed protein, or a portion thereof, can be located on or in an organelle of the cells, such as algal or plant cells. The algae, for example, can then be lysed and the vaccine antigen can be used for inducing an immune response in a host animal to a pathogen if the vaccine antigen is at least partially derived from a pathogenic organism.

In one embodiment, the algae with the vaccine antigen are administered as a food substance. Exemplary animals to which the vaccines can be administered include, but are not limited to, mammals, birds, and aquaculture species. In particular, the vaccine can be administered to aquatic vertebrates such as all vertebrate fish, which may be bony or cartilaginous fish, including, but not limited to, salmonids (including trout, salmon, and Artic char), carp, catfish, yellowtail, seabream, and seabass. Such a vaccine can also be administered to shellfish including, but are not limited to, clams, lobster, shrimp, crab, and oysters. Exemplary methods of delivery include oral administration, as a dried powder, as a component of the normal diet, and by immersion of the animal in a suspension containing the vaccine.

In the case of aquatic vertebrates, examples of pathogenic organisms whose antigenic determinants may be expressed as vaccine antigens on the surface of cells using the methods and systems described herein include, but are not limited to *Rennibacterium salmoninarum* (causative agent of bacterial kidney disease in salmon, trout, char and whitefish; i.e., salmonids), *Aeromonas salmonicida, Aeromonas hydrophila,* species of *Vibrio* (including *V. anguillarum* and *V. ordalii*), species of *Pasteurella* (including *P. piscicida*), species of *Yersinia,* species of *Streptococcus, Edwardsiella tarda* and *Edwardsiella ictaluria,* the viruses causing viral hemorrhagic septicemia, infectious pancreatic necrosis, viremia of carp, infectious hematopoietic necrosis virus, channel catfish virus, grass carp hemorrhagic virus, nodaviridae such as nervous necrosis virus or striped jack nervous necrosis virus, infectious salmon anaemia virus, and the parasites *Ceratomyxa Shasta, Ichthyophthirius multifillius, Cryptobia salmositica, Lepeophtheirus salmonis, Tetrahymena* species, *Trichodina* species and *Epistylus* species.

In the embodiment where the protein is expressed in algae, the algae can be, for example, green algae. For example, algae that can be used include Chlorophyta such as Charoides (e.g., Charoides, Lamprothamnium, Nitellopsis, and Nitella), Zynematales (e.g., Zygnema, Closterium, and Netrium), Codials (e.g., Codium fragile, Helimida opunta, and Caulerpa), Bryopsis plumosa (e.g., Bryopsis, Pseudobryopsis, Bryopsidella, Derbesis, and Pedobesia), Acetabularia Ryukyuensis (e.g., Acetabularia Ryukyuensis, Halicoryne wrightii, Neomeris annulata, Cymopolia van bossei, Bornettella ovalis, and Acetabularia calyculus), Siphonocladales (e.g., Valoniaceae and Boodleaceae), Cladophora (e.g., Anadyomene writii, Cladophora, Cladophora sauteri, and Chaetomorpha), Ulva (e.g., Ulva and Fnteromorpha), Ulotrichales (e.g., Acrosiphoniaceae, Collinsiellaceae, Monostromaceae, and Chlorocystidaceae), Prasiola, Chlorella, Chlorococcales (e.g., Pediastrum and Hydrodictyon), and Volvocales (e.g., Chlamydomonus, Pandorina, Pleodorina, and Volvox).

Exemplary algae that typically can be used in any of the embodiments described in this application include *Chlamydomonas* species, particularly *Chlamydomonas reinhardtii, Chlorella* species, and *Volvox* species. *Chlamydomonas reinhardtii,* a unicellular eukaryotic green algae is particularly advantageous. *Chlamydomonas* strains are available, for example, from *Chlamydomonas* Genetic Stock Center, Duke University (Durham, N.C.). Auxotrophic mutants of *Chlamydomonas reinhardtii* (mutants that differ from the wild-type in requiring one or more nutritional supplements for growth) are readily available at the *Chlamydomonas* Genetic Stock Center and such mutants can be genetically complemented by the transforming DNA (i.e., exogenous DNA introduced into the cell), which facilitates selection of algae containing a desired transgene. In other embodiments disabled algae can be used. Disabled algae are genetically engineered such that they will not proliferate unless they are in very specific controlled environments (i.e., such strains will not grow or transfer their genes in the wild). Within the context of this disclosure, such algae are said to be "disabled." Use of such disabled strains inhibits or limits spread of the transgenic algae used in the present invention into the environment.

Exemplary plants suitable for use in the methods and systems described herein include cultured plant cells (protoplasts and callus cells) and whole plants (single cell and multicellular plants). In various embodiments, the plant cells (i.e., cultured plant cells or cells of whole plants) can be from plants including oat, wheat, rye, barley, rice, safflower, maize, legumes, such as alfalfa, soy bean, tomato, sugar beet, and potato plants. Other useful plants can be, for example, fruit-bearing plants, such as plants that bear apples, pears, cherries, grapes, citrus fruits, pineapples and bananas, and trees, such as larch. Other suitable plants include oil palms, tea, cocoa and coffee shrubs, tobacco, cotton, flax, sunflower, pasture grasses, forage cereals, feed plants, and peanut and lentil plants. Other useful plants include Arabidosis, soapworts (Saponaria), duckweed (Leminacea), ferns, mosses, and liverworts. In this embodiment, vectors commonly used in genetic engineering in plants can be used for the transfer of the nucleic acid molecules according to the invention to plant cells.

In the methods and systems described herein the first and second nucleic acids are introduced into the cells (e.g., algal or plant cells). In this embodiment, the first nucleic acid encodes a promoter that is either inducible, repressible, or both inducible and repressible, and the second nucleic acid encodes a stability factor (e.g., Nac2 or Mbb1) that regulates the expression of a plastid mRNA. In another illustrative embodiment, the second nucleic acid can code for a translational activating factor, such as, for example, Tbc2 or Tca1.

The inducible or repressible promoter controls the expression of the stability factor. In various embodiments, any suitable type of inducer or repressor (e.g., a chemical or modified environmental condition) can be used depending on the nuclear promoter being used. An exemplary promoter suitable for use in the methods and systems described herein is the Cyc6 promoter (see FIG. 12). Any other suitable promoters can be used including promoters with sequence similarity to the Cyc6 promoter sequence, such as 60%, 70%, 80%, 85%, 90%, 95%, or 98% sequence similarity to the Cyc6 promoter. Also, sequences capable of hybridizing to the complement of the Cyc6 promoter under stringent hybridization conditions can be used. Other suitable inducible or repressible promoters that can be used include promoters that respond to factors such as environmental conditions (such as anoxia, heat, drought, or light), chemicals, nutrients, hormones, pathogens, injury, herbivory, developmental stage, and tissue type. Such promoters are known to those skilled in the art. Promoters may respond to more than one factor, and a single factor may activate or repress more than one promoter.

In addition to Cyc6, other inducible promoters in Chlamydomonas include the promoter for the $CO_2$-induced plasma-membrane protein gene (Genbank accession no. U31976), the promoter for the FEA1 gene which is tightly controlled by iron availability (Sasaki et al., 1998; Rubinelli et al., 2002), and the promoter of the Nit1 gene that is negatively repressed in the presence of ammonium and glutamate and induced in media lacking ammonium (Fernandez 1989). Examples of inducible promoters in higher plants include the light inducible promoter of the small subunit of Rubisco, the U-V inducible promoter of the chalcone synthase gene, the coumaric-acid inducible promoter of the chalcone synthase gene, the hypoxia inducible promoter of the alcohol dehydrogenase gene, and the pathogenesis-induced promoters (PR-1-14) of tobacco, tomato, cucumber, and arabadopsis.

The stability factor is expressed under the control of the inducible andlor repressible promoter and is introduced into the plastid where the stability factor associates, directly or indirectly (e.g., through accessory proteins), in the plastid with an untranslated region of an mRNA to stabilize the mRNA. In various embodiments, the untranslated region of the mRNA can be at the 5' or the 3' end of the mRNA. The mRNA is transcribed from the third nucleic acid which encodes the expressed protein. In another illustrative embodiment, mRNA can be transcribed from additional nucleic acids operatively linked to the third nucleic acid or not linked to the third nucleic acid and controlled by their own stability factors. Thus, the expressed protein is produced in the plastid under the control of the stability factor, the expression of which is controlled by the inducible andlor repressible nuclear promoter.

In one illustrative aspect, the stability factor can associate, directly or indirectly, not only with untranslated regions of the mRNA either at the 5' or the 3' end of the mRNA, or both, but the stability factor can also associate, directly or indirectly, with coding regions of the mRNA. In another illustrative aspect, the stability factor can associate directly or indirectly with the mRNA, for example, by association with other accessory proteins in a complex where the other proteins associate directly or indirectly with the mRNA untranslated andlor coding regions.

In one embodiment, the first and second nucleic acids are incorporated into nuclear DNA employing, for example, integration or recombination (e.g., homologous recombination or other types of recombination). In another embodiment, the first and second nucleic acids are expressed using an expression vector that is introduced into the cells. In this embodiment, the first and second nucleic acid inserts in the vector do not recombine with nuclear DNA, but, rather, the second nucleic acid, coding for the stability factor, is expressed autonomously using regulatory sequences present in the vector including the inducible andlor repressible promoter coded by the first nucleic acid. Any suitable vector known to those skilled in the art can be used including the vectors described herein in Examples 1-4.

In each of these embodiments, the first nucleic acid is operatively linked to the second nucleic acid to form a recombinant nucleic acid. An exemplary recombinant nucleic acid described herein is the Cyc6 promoter (i.e., the first nucleic acid) operatively linked to the Nac2 coding sequence (i.e., the second nucleic acid). The first and second nucleic acids can be operatively linked to each other by using cloning methods well-known to those skilled in the art, including methods of digesting nucleic acids with restriction enzymes and ligating the first and second nucleic acids to one another and to the ends of a digested vector, using ligases. Such cloning methods are described, for example, in Sambrook et al., "Molecular Cloning: A Laboratory Manual", 3rd Edition, Cold Spring Harbor Laboratory Press, (2001), incorporated herein by reference, or in S. Surzycki, "Basic Techniques in Molecular Biology," Springer-Verlag (2000), incorporated herein by reference.

In embodiments where the second nucleic acid is expressed autonomously under the control of the promoter coded for by the first nucleic acid, the expression construct (i.e., the vector-insert construct) typically comprises a transcription terminator for terminating the transcription of the coding sequence present in the second nucleic acid, and can contain other 5' and 3' regulatory sequences. The transcription terminator is typically present in the second nucleic acid, but can be incorporated into the vector.

In embodiments where the first and second nucleic acids are stably incorporated into nuclear DNA, the transcription terminator is typically present in the second nucleic acid, but can be part of the nuclear DNA sequence. The additional 5' and 3' regulatory sequences can be present in the first or second nucleic acids, in the vector, andlor in nuclear DNA, such as transcriptional enhancer elements and sequences involved in mRNA stabilization. In this embodiment, the vector can also contain nuclear targeting sequences that facilitate integration of the recombinant nucleic acid into nuclear DNA. In one embodiment, the nucleus can have an inoperative copy or can be missing a copy or a homolog of the second nucleic acid.

In various embodiments described herein, the vectors for autonomous expression of the stability factor or for incorporation of the recombinant nucleic acid into nuclear DNA have a bacterial origin of replication for replicating the vector construct to make large-scale preparations of desired vectors with or without the inserted recombinant nucleic acid (i.e., the operatively linked first and second nucleic acids) for use in cloning. The vectors also typically have restriction endonuclease cleavage sites for the insertion of DNA fragments (e.g., a multiple cloning site), and selectable genetic markers for the selection of transformants. The selectable marker can be a marker, such as the aadA gene or nptll, which allows for growth of the transformed cells on media supplemented with antibiotics (Goldschmidt-Clermont, *Nucl. Acids Res.*, vol. 19, pages 4083-4089 (1991)). Both native gene (arg7, nit1) and foreign gene (ble, aphVlll, aadA, nptll) selectable markers have been developed as reporter genes for nuclear transformation.

The vectors with the recombinant nucleic acid (i.e., an insert comprising the first and second nucleic acids) are introduced into the cells (e.g., algal or plant cells) by standard transformation techniques well-known to those skilled in the art. Exemplary transformation methods include electroporation, glass-bead mediated DNA delivery, the use of polyethylene glycol-mediated transformation, biolistics, and the like.

In one embodiment, for transforming algae, autolysin, an enzyme which is released during mating and degrades cell walls is used to break down the cell wall before transformation. In an alternate embodiment, mutant strains which lack the ability to synthesis the cell wall (e.g., cw15cw10) have been generated and can be used for efficient transformation.

In one illustrative aspect, transformants can be detected by PCR and Southern blotting. Other procedures known to those skilled in the art can also be used, such as for example, antibiotic addition, copper addition, antibody detection (e.g., ELISA and Western blotting), and sequencing. The choice of such procedure depends upon the construct used.

If a transgene is to be expressed in the plastid, the third nucleic acid can be incorporated into a vector and the vector constructs can be made and can be replicated generally as discussed above for the first and second nucleic acids. Illustratively, plastid transformation can be achieved with biolistics, in which the vector containing the transgene is introduced into the cell on a gold or tungsten microparticle accelerated by an inert gas, such as helium. This method may cause less damage to the cells. In a related illustrative embodiment, the cells to be transformed can be plated on selective solid agar media and DNA-coated tungsten beads can be delivered into the plastid by accelerating them with helium gas or gun powder. Using this technique, efficient delivery of recombinant DNA into the plastid can be achieved.

In one embodiment, detection of integration of the third nucleic acid into plastid DNA can rely on expression of heterologous DNA encoding the bacterial aminoglycoside adenyl transferase gene (aadA). This embodiment enables a method of selecting transformants using the antibiotic spectinomycin or streptomycin. Using this reporter construct, it is possible to specifically insert, disrupt, modify, mutate or delete any non-essential gene or cis acting elements in the plastid.

In another illustrative embodiment, chloroplast transformation with a transgene can be achieved using a transgene flanked by homologous chloroplast targeting sequences that facilitate integration of the transgene into the chloroplast DNA. In one embodiment, integration of the transgene can occur by two homologous recombination events between the flanking chloroplast sequences of the vector and their homologous sequences in the chloroplast genome. In one embodiment, the chloroplast can have an inoperative copy or can be missing a copy or a homolog of the third nucleic acid.

Exemplary modifications of nucleic acids that make the nucleic acids foreign include, but are not limited to, modifying the nucleic acids to achieve codon optimization, ligating the nucleic acids to 5' or 3' untranslated regions of other genes, adding promoter or termination sequences to nucleic acids, ligating sequences useful for homologous recombination, and adding other elements required for gene expression, targeting, or stabilization, for example, to the nucleic acids. Additional modifications include fusing the nucleic acid to the nucleic acid of other native or transgenes to form a fusion protein.

Exemplary schematic outlines of plastid gene regulation systems that are within the scope of this invention are shown in FIGS. 2-5. FIG. 1 shows a schematic outline of a plastid gene regulation system in which the nuclear inducible promoter is induced in the presence of an inducer. In this embodiment, the inducer (e.g., an environmental condition such as low oxygen levels) induces the promoter that regulates expression of the stability factor and the stability factor is expressed. Following translation, the stability factor is targeted to the plastid where it associates with a specific mRNA, depending on the stability factor being expressed, and the mRNA and the protein it encodes are expressed.

Figure 3:
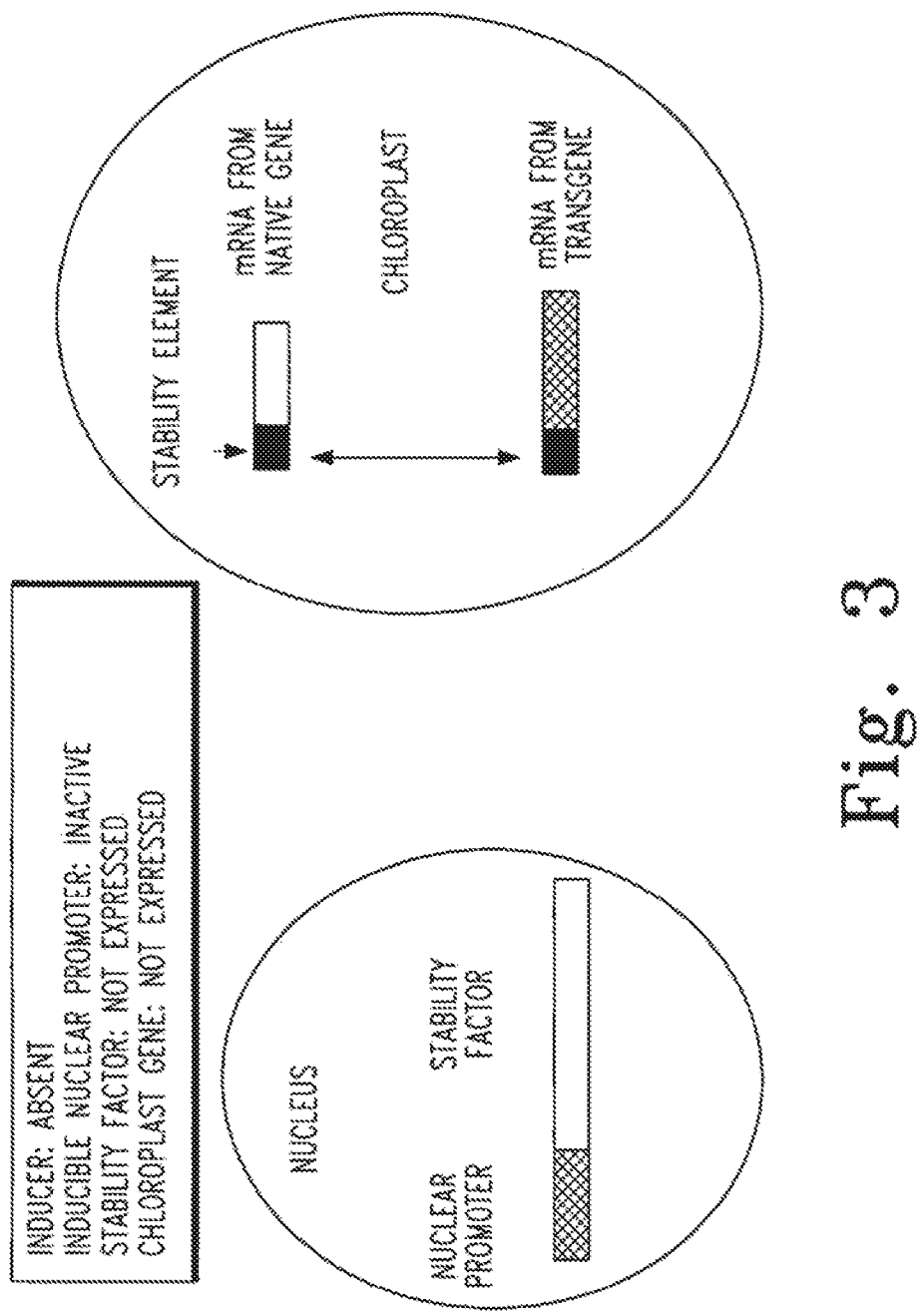
FIG. 3 shows a schematic outline of a plastid gene regulation system in which the nuclear inducible promoter is repressed in the absence of an inducer. The left-hatched box represents the nuclear inducible promoter and the right-hatched box represents the gene for the stability factor. The filled box represents the stability factor association element, in this embodiment located in the 5' untranslated region of the plastid mRNA. The open box represents an mRNA produced from a plastid native gene. The cross-hatched box represents an mRNA produced from a foreign gene in the plastid.

FIG. 3 shows a schematic outline of an exemplary plastid gene regulation system in which the nuclear inducible promoter is repressed in the absence of an inducer. In this embodiment, the absence of the inducer, the inducible promoter is not activated and the stability factor is not expressed. Without the stability factor, the mRNA in the plastid is degraded or not translated and the protein is not expressed.

Figure 4:
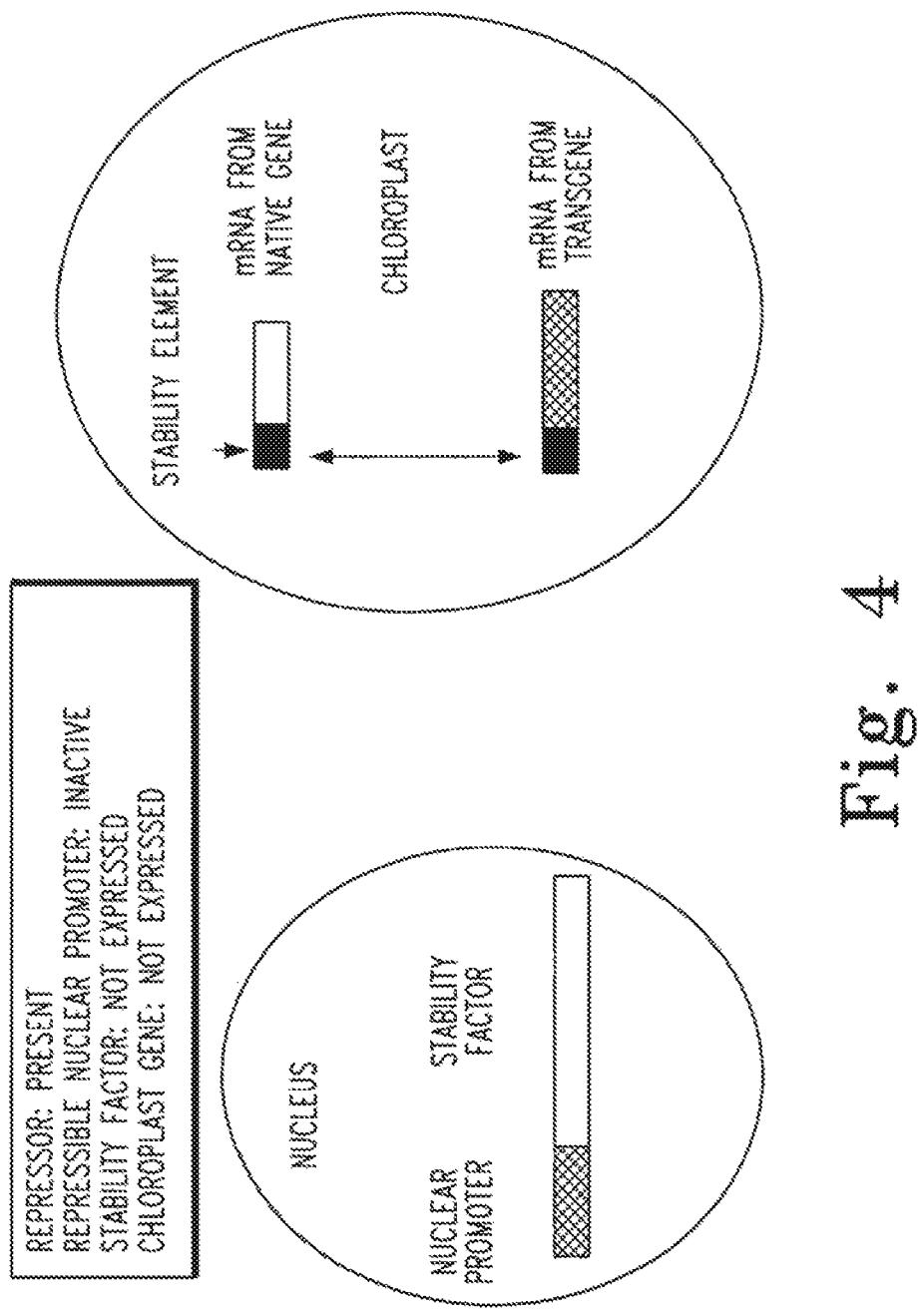
FIG. 4 shows a schematic outline of a plastid gene regulation system in which the nuclear repressible promoter is repressed in the presence of a repressor. The left-hatched box represents the nuclear repressible promoter and the right-hatched box represents the gene for the stability factor. The filled box represents the stability factor association element, in this embodiment located in the 5' untranslated region of the plastid mRNA. The open box represents an mRNA produced from a plastid native gene. The cross-hatched box represents an mRNA produced from a foreign gene in the plastid.

FIG. 4 shows a schematic outline of an exemplary plastid gene regulation system in which the nuclear repressible promoter is repressed in the presence of a repressor (e.g., a predetermined level of copper in the medium). In this embodiment, in the presence of the repressor, the repressible promoter is not activated and the stability factor is not expressed. Without the stability factor, the mRNA in the plastid is degraded or not translated and the protein is not expressed.

Figure 5:
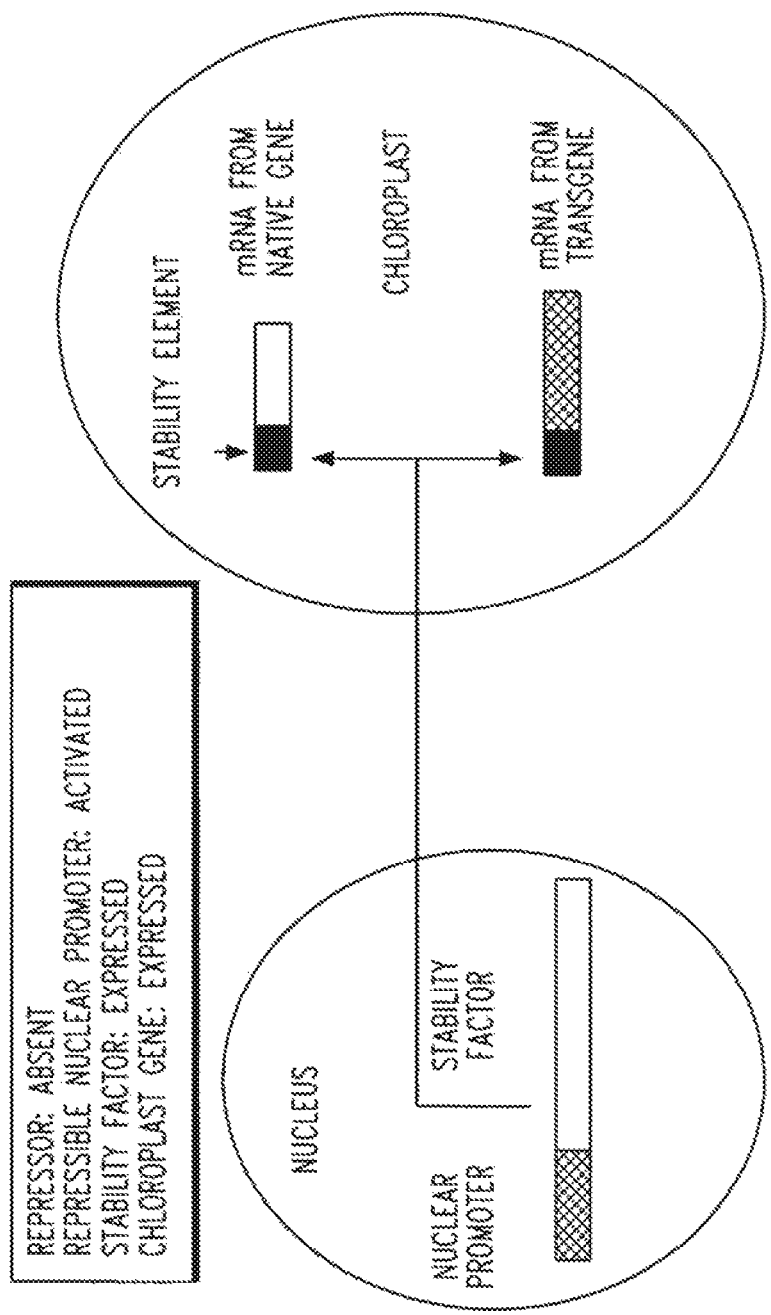
FIG. 5 shows a schematic outline of a plastid gene regulation system in which the nuclear repressible promoter is induced in the absence a repressor. The left-hatched box represents the nuclear repressible promoter and the right-hatched box represents the gene for the stability factor. The filled box represents the stability factor association element, in this embodiment located in the 5' untranslated region of the plastid mRNA. The open box represents an mRNA produced from a plastid native gene. The cross-hatched box represents an mRNA produced from a foreign gene in the plastid.
Figure 6:
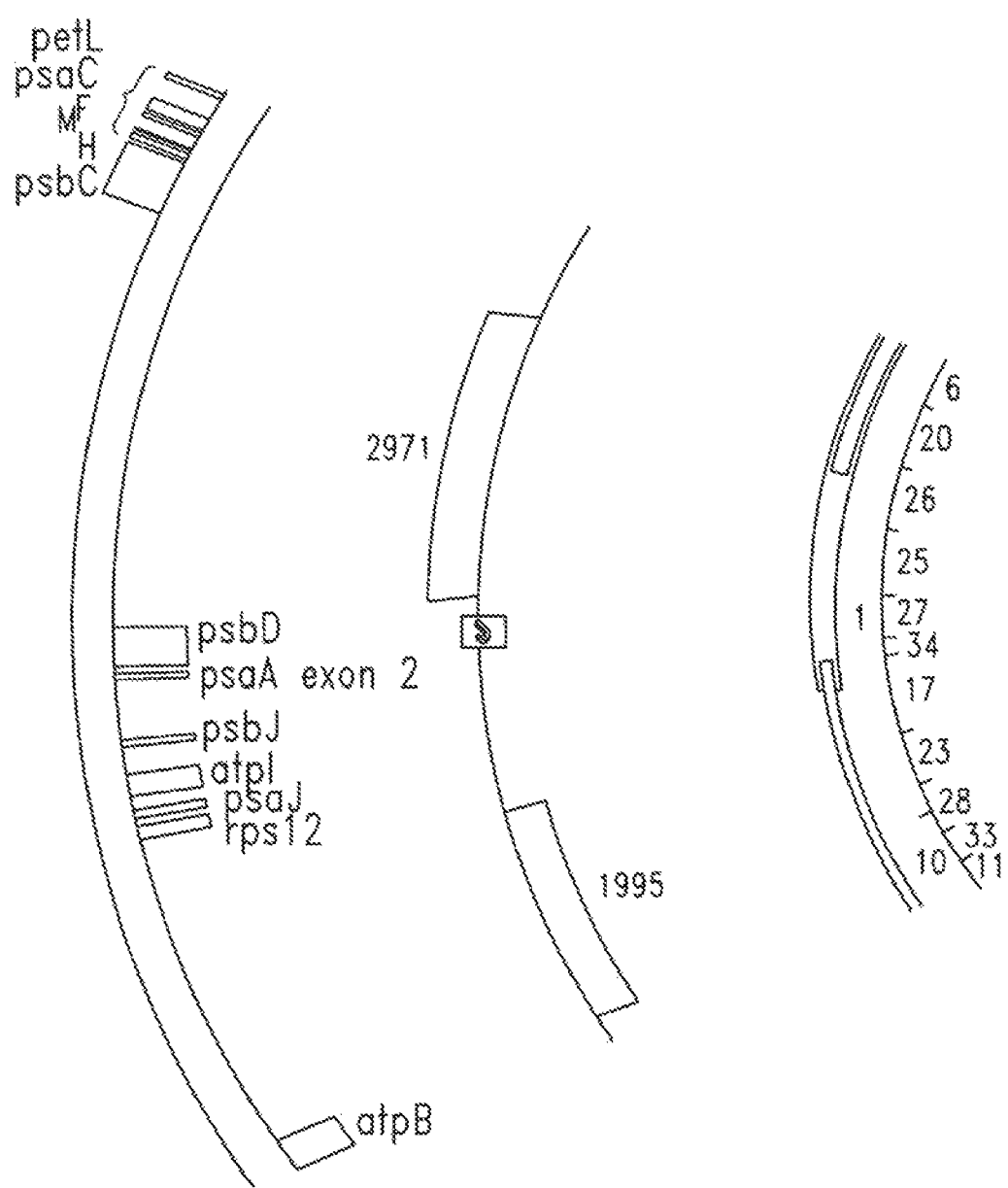
FIG. 6 shows a schematic of the Chlamydomonas chloroplast genome with the psbD gene location shown. The arrow indicates the site of insertion of pSK108.

FIG. 5 shows a schematic outline of an exemplary plastid gene regulation system in which the nuclear repressible promoter is induced in the absence a repressor (e.g., a reduced level of copper in the medium or the absence of copper in the medium). In this embodiment, in the absence of the repressor the nuclear promoter that regulates expression of the stability factor is induced and the stability factor is expressed. Following translation, the stability factor is targeted to the plastid where it associates with a specific mRNA, depending on the stability factor being expressed, and the mRNA and the protein it encodes are expressed.

In embodiments where it is desirable to isolate and purify the expressed proteins obtained using the methods and systems described herein, the proteins can be expressed and then purified using conventional techniques. For example, the proteins can be obtained in a form that is about 40% pure, about 50% pure, about 60% pure, about 70-80% pure, about 90% pure, about 95% pure, or about 98% pure. For purification from the cells, a lysate can, for example, be subjected to ammonium sulfate precipitation followed by DEAE-Sepharose column chromatography. Other conventional techniques known to those skilled in the art can be used such as gel filtration, ion exchange chromatography, DEAE-Sepharose column chromatography, affinity chromatography (such as using the FLAG-tagged system described in Example 2 below), solvent-solvent extraction, ultrafiltration, and HPLC. Alternatively, purification steps may not be required because the proteins may be present in such high concentrations that the protein is essentially pure in the lysate (e.g., 70-80% pure). The expressed protein can be concentrated by such techniques as, for example, ultrafiltration and tangential flow filtration.

In one embodiment, the cells can be lysed, for example, by sonication, heat, or chemical treatment, and the homogenate centrifuged to remove cell debris. The supernatant can then be subjected to ammonium sulfate precipitation, and additional fractionation techniques as required, such as gel filtration, ion exchange chromatography, DEAE-Sepharose column chromatography, affinity chromatography, solvent-solvent extraction, ultrafiltration, and HPLC to purify the expressed protein. It should be understood that the purification methods described above for purification of the expressed proteins from the culture medium or from cells are nonlimiting and any purification techniques known to those skilled in the art can be used to purify the expressed proteins if such techniques are required to obtain a substantially pure protein.

The cells (e.g., algal or plant cells) can be cultured using a variety of techniques to promote protein expression. Culture media for cells, including algal and plant cells, are known in the art and are typically supplemented with a carbon source (e.g., glucose or acetate). The cells can be cultured to maintain a desired density, for example, as described below using a culture system and device useful for the production of hydrogen gas as an example.

As discussed in detail above, the expression methods and systems described herein may be used to produce hydrogen. Thus, in another embodiment an apparatus for the production of hydrogen is provided. The apparatus comprises a first vessel configured to hold a cell culture in a substantially oxygen-depleted environment, a first pump in fluid communication with the first vessel and configured to pump a medium into the first vessel at a predetermined rate, and a measuring device coupled to the first vessel and configured to measure an amount of hydrogen produced by the cell culture.

Figure 7:
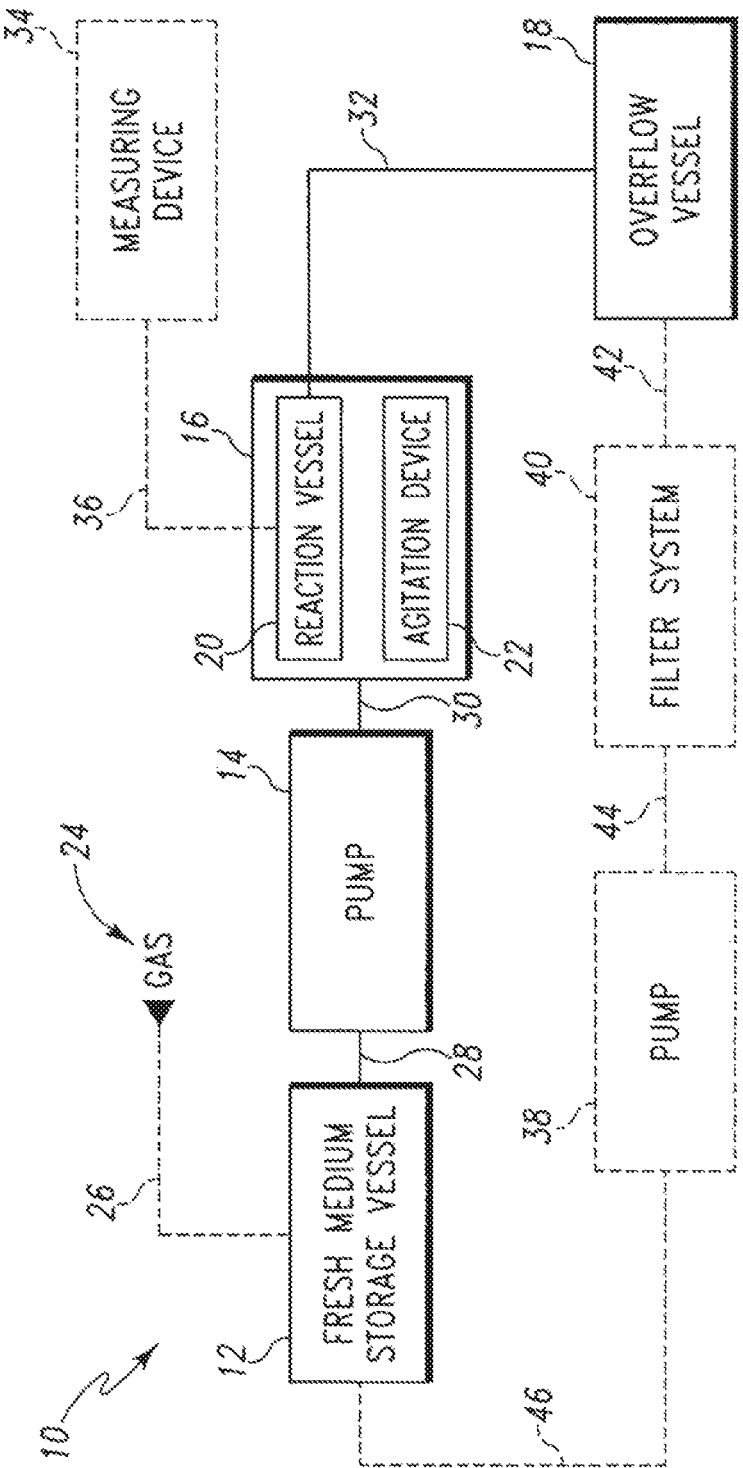
FIG. 7 shows a flow diagram for an apparatus for producing hydrogen.

FIG. 7 illustrates an apparatus 10 for producing hydrogen that may be used in some embodiments. The apparatus 10 includes a fresh medium storage vessel 12, a pump 14, a reaction system 16, and an overflow vessel 18. The fresh medium storage vessel 12 may be embodied as any type of vessel capable of storing an amount of medium, such as TAP (acetate) or HSM (minimal), in a substantially hermetically-sealed environment. In some embodiments, an amount of gas 24, such as argon gas, is pumped into the fresh medium storage vessel 12 via a conduit 26 to purge the vessel 12 of oxygen to thereby form a substantially oxygen-depleted environment therein. The conduit 26 may be embodied as any type of tube, line, or other conduit capable of facilitating passage of a fluid (e.g., a gas) into the fresh medium storage vessel.

The pump 14 is fluidly coupled to the fresh medium storage vessel 12 via a conduit 28 and to the reaction system 16 via a conduit 30. The conduit 28 (and the conduit 26 if included) is coupled to the vessel 12 such that the substantially hermetically-seal environment of the fresh medium storage vessel 12 is maintained. The conduits 28,30 may be embodied as any type of tubes, lines, or other conduits capable of facilitating passage of a fluid via a pumping action provided by the pump 14. The pump 14 may be embodied as any type of pump capable of pumping an amount of medium from the fresh medium storage vessel 12 to the reaction system 16 at a predetermined rate without adversely interacting with the fresh medium. For example, in one particular embodiment, the pump 14 is embodied as a peristaltic pump such that the potential for damage to the medium during the pumping process is reduced.

The reaction system 16 includes a reaction vessel 20 and an agitation device 22. The reaction vessel 20 is substantially similar to fresh medium storage vessel 12 and may be embodied as any type of vessel capable of storing an amount of medium and algae culture, or other type of host cell, in a substantially hermetically-sealed environment. Fresh medium is pumped from the fresh medium storage vessel 12 to the reaction vessel 16 via the conduits 28, 30 and the pump 14. Because the fresh medium is stored in a substantially oxygen-depleted environment, the likelihood of inadvertently introducing oxygen into the reaction vessel 16 is reduced. The conduit 30 is coupled to the reaction vessel 20 such that the substantially hermetically-sealed environment of the reaction vessel 12 is maintained.

The agitation device 22 is operably coupled to the reaction vessel 20 and may be embodied as any type of device capable of maintaining the culture stored in the reaction vessel 20 in an agitated state. For example, the agitation device 22 may be embodied as an automated stirring device such as a magnetic stir bar assembly or the like.

A conduit 32 drains any overflow of culture from the reaction vessel 20 to an overflow vessel 18. The overflow vessel 18 may be substantially similar to vessels 12, 20 and may be embodied as any type of vessel capable of storing an amount of culture therein. The conduit 32 is substantially similar to conduits 28, 30 and may be embodied as any type of tube, line, or other conduit capable of facilitating passage of a fluid from the reaction vessel 20 to the overflow vessel 18. Similar to conduit 30, the conduit 28 is coupled to the reaction vessel 20, such the that substantially hermetically-sealed environment of the reaction vessel 20 is maintained. The conduit 30 may be coupled to the reaction vessel 20 in a position such that the level of culture contained in the reaction vessel 20 remains at (or within) a predetermined level(s) by expelling a portion of the culture into the overflow vessel 18.

In some embodiments, a measuring device 34 may be coupled to the reaction vessel 20 via a communication link 36 such that the amount of hydrogen or other gas produced by the culture in the vessel 20 may be measured. The measuring device 34 may be embodied as any type of device capable of measuring an amount of the gas of interest. In one particular embodiment, the measuring device 34 is embodied as a mass spectrometer, but in other embodiments, other types of measuring devices may be used. The communication link 36 may be any type of communication link capable of facilitating the communication of data to the measuring device 24 such as, for examples, any number of wires, cables, fiber optic cables, tubes, conduits, or the like. In one particular embodiment, the communication link 36 includes an electrode portion positioned in the reaction vessel 20. The electrode portion may be, for example, a silver electrode.

In some embodiments, the apparatus 10 may include a filter system 40 and a secondary pump 38. The filter system 40 is coupled to the overflow vessel 18 via a conduit 42 and to the pump 38 via a conduit 44. The pump 38 is coupled to the fresh medium storage vessel 12 via a conduit 46. The conduits 42, 44, 46 are substantially similar to conduits 28, 30, 32 and may be embodied as any type of tube, line, or other conduit capable of facilitating passage of a fluid. The pump 38 may be similar to the pump 14 and may be embodied as any type of pump capable of pumping an amount of "spent" culture from the overflow storage vessel 18 to the reaction fresh medium storage vessel 12 at a predetermined rate without adversely interacting with the fresh medium. For example, in one particular embodiment, the pump 38 is embodied as a peristaltic pump. The filter system 40 may be embodied as any number and type of filters and associated interconnects that are capable of filtering the culture stored in the overflow vessel 18.

In operation, the pump 14 is configured to pump fresh medium from the fresh medium storage vessel 12 to the reaction vessel 20 of the reaction system 16 at a predetermined rate. In one particular embodiment, the pump 14 is configured to pump the fresh medium into the reaction vessel 20 at a rate substantially equal to a rate of cell growth of an algae stored in the reaction vessel 20. As discussed in detail above, because the algae, or other host cell type, is stored in the reaction vessel 20 in a substantially oxygen-depleted environment desirable gene expression is induced in the algae, or other host cell type, such that hydrogen production is increased. The substantially oxygen-depleted environment of the reaction vessel 20 is maintained while introducing fresh medium from the fresh medium storage vessel 12 because such fresh medium is also stored in a substantially oxygen-depleted environment in the vessel 12 as discussed above. Alternatively, in other embodiments, the algae, or other host cell type, stored in the reaction vessel 20 may be self-induced. Regardless, it should be appreciated that apparatus 10 is a single phase apparatus. That is, the algae, or another host cell type, stored in the reaction vessel 20 proliferate and are induced in the same vessel.

As fresh medium is introduced into the reaction vessel 20, the agitation device 22 is configured to keep the culture stored in the reaction vessel in a continual state of agitation. In addition, as fresh medium is introduced, a portion of the existing culture is removed from the reaction vessel to the overflow vessel 18. In this way, the amount of algae, or another host cell type, contained in the reaction vessel 20 is maintained at a substantially constant value. In embodiments including the pump 38 and the filter system 40, the pump 38 removes an amount of "spent" culture from the overflow vessel and reintroduces such medium into the fresh medium storage vessel after being filtered by the filter system 40 to remove any algae, or other host cell type, contained therein.

Figure 8:
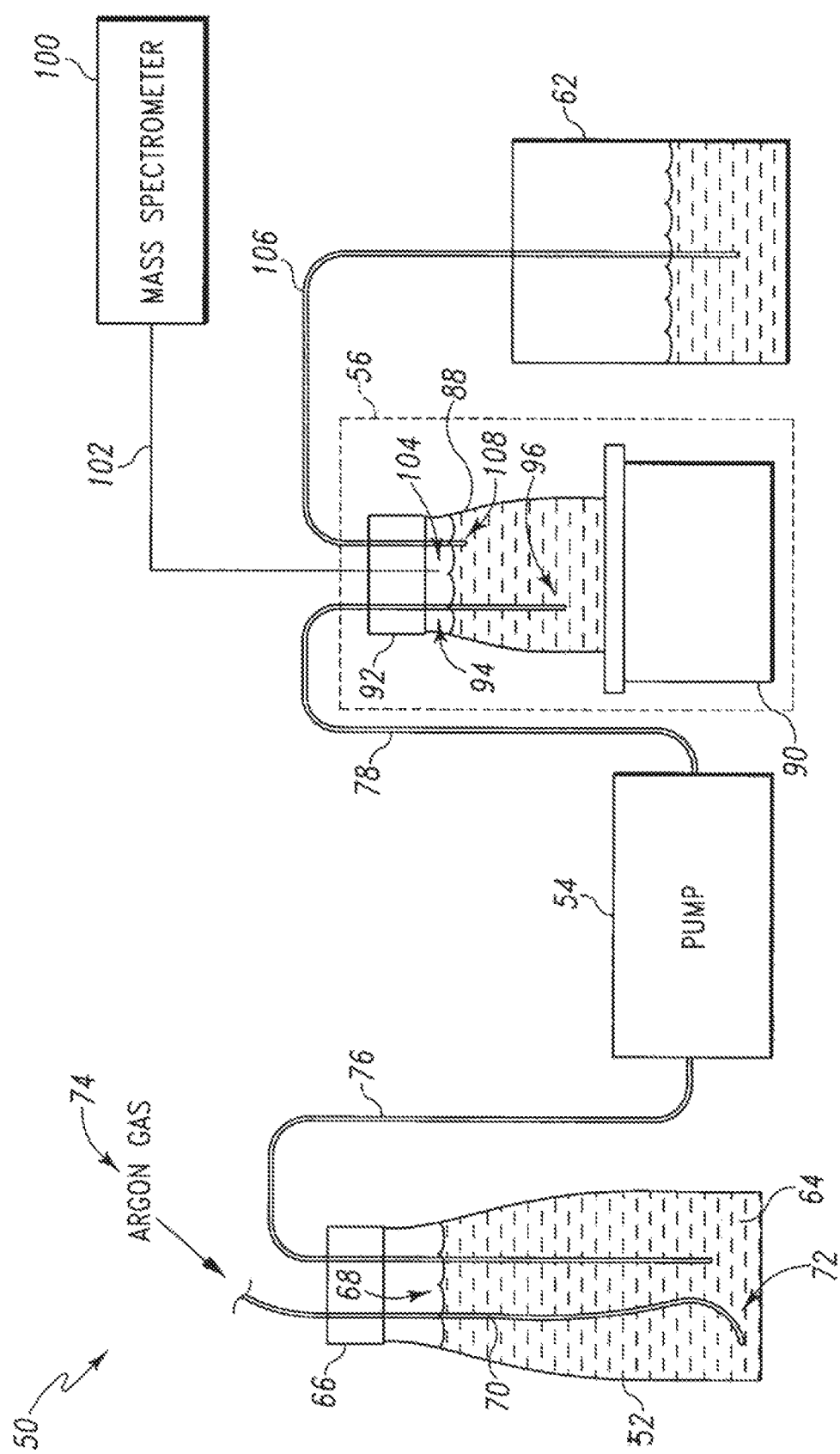
FIG. 8 shows an apparatus for producing hydrogen.

Referring now to FIG. 8, in one particular embodiment, an apparatus 50 for producing hydrogen includes a fresh medium storage vessel 52, a peristaltic pump 54, a reaction system 56, and an overflow vessel 62. The fresh medium storage vessel 52 is substantially similar to the fresh medium storage vessel 12 and is illustratively embodied as a 0.25 liter vessel. An amount of fresh medium 64, illustratively embodied as TAP (acetate) or HSM (minimal), is stored in the vessel 52. A cap 66 is coupled to the vessel 52 such that an inner cavity 68 of the vessel 52 is substantially hermetically-sealed from the outside environment. A conduit 70 is coupled to the cap 66 and includes an end portion 72 positioned in the inner cavity 68 of the vessel 52. An amount of argon gas 74 is introduced into the inner cavity 68 via the conduit 70 to thereby substantially purge the inner cavity of oxygen.

The peristaltic pump 54 is coupled to the fresh medium storage vessel 52 via a conduit 76 and to the reaction system 56 via a conduit 78. The peristaltic pump 54 is illustratively embodied as a model IP4 peristaltic pump, which is commercially available from Ismatec of Glattburg, Switzerland. The pump 54 is configured to pump an amount of fresh medium from the fresh medium storage vessel 52 to the reaction system 56 at a predetermined rate substantially equal to the growth rate of an algae culture, or another host cell type, stored in the reaction system 56.

The reaction system 56 includes a reaction vessel 88, illustratively embodied as a 0.25 liter vessel, and a magnetic stir bar system 90 configured to continually agitate an amount of medium and algae culture 94, or another host cell type, stored in the reaction vessel 88. The magnetic stir bar system 90 is illustratively embodied as a model KM02 magnetic stir bar, which is commercially available from Milian of Geneva, Switzerland. A cap 92 is coupled to the reaction vessel 88 such that an inner cavity 94 of the vessel 88 is substantially hermetically-sealed from the outside environment. The conduit 78 is coupled to the cap 92 and includes an end portion 96 positioned in the inner cavity 94 of the reaction vessel 88.

A mass spectrometer 100 is also coupled to the reaction vessel 88 via a communication link 102. The mass spectrometer 100 is illustratively embodied as a model MM8-80 mass spectrometer, which is commercially available from VG Instruments of Cheshire, United Kingdom. The communication link 102 includes an electrode 104 positioned in the inner cavity 94 of the vessel 88. The mass spectrometer 100 is configured to measure the amount of hydrogen (and, in some embodiments, the amount of oxygen) produced by the medium and algal culture, or another host cell type, stored in the reaction vessel 88.

Additionally, a conduit 106 is coupled to the cap 92 and includes an end portion 108 positioned in the inner cavity 94 of the vessel 88. A distal end 110 of the conduit 106 is positioned in an inner cavity of the overflow vessel 62. The conduit 106 is so positioned such that an amount of medium and algal culture, or another host cell type, is removed from the reaction vessel 88 at a rate substantially equal to a rate of cell growth of the algae, or another host cell type, stored in the reaction vessel 88.

The description above applies to all of the methods and systems described herein. The following examples are for purposes of illustration only and are not intended to limit the scope of the invention as defined in the claims which are appended hereto. The references cited in this document are specifically incorporated herein by reference.

EXAMPLE 1

Inducible Plastid Expression System for a Native Gene

A vector containing the Nac2 gene under the control of the Cyc6 promoter was constructed using molecular cloning techniques known to those skilled in the art. Cloning methods are described, for example, in Sambrook et al., "Molecular Cloning: A Laboratory Manual", 3rd Edition, Cold Spring Harbor Laboratory Press, (2001), incorporated herein by reference or in S. Surzycki, "Basic Techniques in Molecular Biology," Springer-Verlag (2000), incorporated herein by reference.

To place the Nac2 gene under the control of the Cyc6 promoter element, a chimeric DNA fragment comprising the Cyc6 promoter fused to the coding sequence of psbD was generated by overlap-extension PCR using 4 oligonucleotides specific for the Cyc6 promoter element and Nac2 genomic DNA. The resulting PCR fragment consisted of a 428 base-pair fragment of Cyc6 promoter sequence fused in frame with an 833 base-pair fragment of Nac2 genomic sequence. The PCR fragment was sub-cloned and sequenced. The PCR fragment was then cloned into the pNac2(midi) plasmid using the unique restriction sites Xbal and Aatll. The pNac2(midi) plasmid contains a 5.1 kb chimeric midi-gene of Nac2 which has been previously described by Boudreau et al. (2000), incorporated herein by reference. The gene is composed of the 5' genomic sequence of Nac2 fused to the 3' cDNA sequence and results in an open reading frame (ORF) encoding the entire Nac2 protein which is tagged with a triple HA epitope at the C-terminal end of the protein. The pNac2(midi) was digested with Xbal and Aatll. The PCR fragment was then ligated directionally into the plasmid. The resulting plasmid pcy6Nac2(midi) contains a 428 basepair fragment of Cyc6 promoter sequence fused in frame with the Nac2 midi gene.

Figure 9:
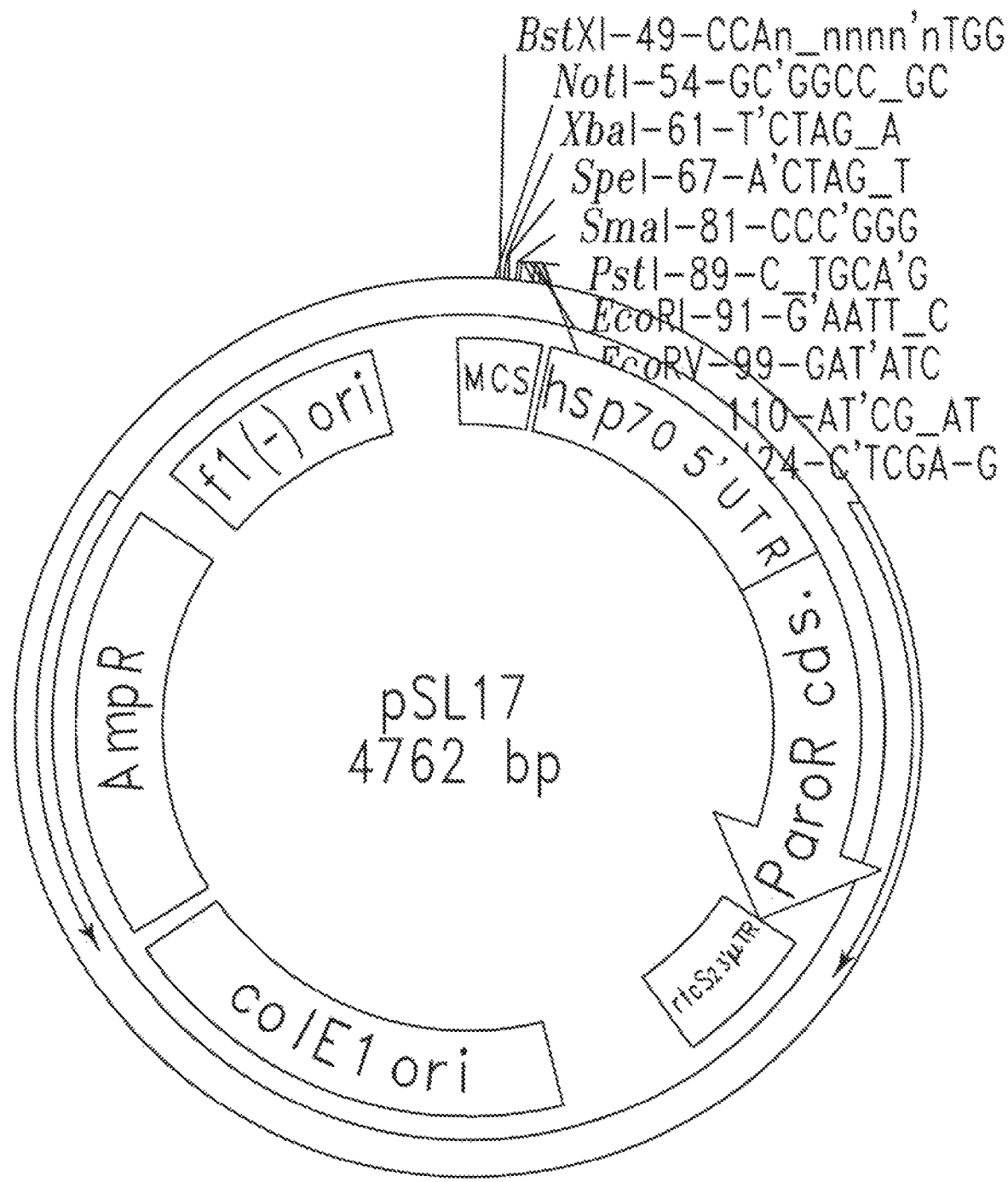
FIG. 9 shows a schematic of the nuclear expression vector pSL17 used to transform nuclear Nac2 mutants and to introduce the Cyc6 promoter and the Nac2 gene. The map shows the arrangement of promoters, enhancer element from HSP70A promoter, and restriction sites for inserting the Cyc6 promoter and Nac2 gene.

Finally, the 5.8 kb cyc6Nac2transgene was cloned into the pSL17 plasmid using the unique restriction sites in the multiple cloning site of pSL17 (i.e., EcoRI and Xbal; see FIG. 9). pSL17 contains the aphVII cassette conferring resistance to the antibiotic paromomycin and a multiple cloning site for cloning. The resulting 10.8 kb plasmid, pcy6Nac2(paroR) (see FIG. 10), was used to transform nac2-26 mutant cells. Sequences for Nac2 and Cyc6 used in the construction of the vector are provided in FIGS. 11 and 12, respectively.

The pcy6Nac2(paroR) vector was introduced into a nac2 null mutant, nac2-26 by electroporation. Algal and plant transformation methods are known to those skilled in the art and are described, for example, in Sambrook et al., "Molecular Cloning: A Laboratory Manual", 3rd Edition, Cold Spring Harbor Laboratory Press, (2001), incorporated herein by reference.

To isolate a transgenic *Chlamydomonas* strain containing a Cyc6 inducible Nac2 gene, nac2-26 cells were first treated with autolysin and then transformed by electroporation using pcyc6Nac2(paroR). The resulting transformants were plated on TAP medium supplemented with the antibiotic paromomycin (20 μg/ml). Paromomycin resistant colonies were screened for the ability to grow photo-autotrophically on minimal medium supplemented with 150 μM Nickel(II), (an inducer of Cyc6 transcription) and minimal medium lacking copper (HSM-$Cu^{+2}$; see FIG. 13). Photo-autotrophic strains were then tested for the abilitylinability to grow on minimal medium lacking the inducer (HSM).

Figure 13:
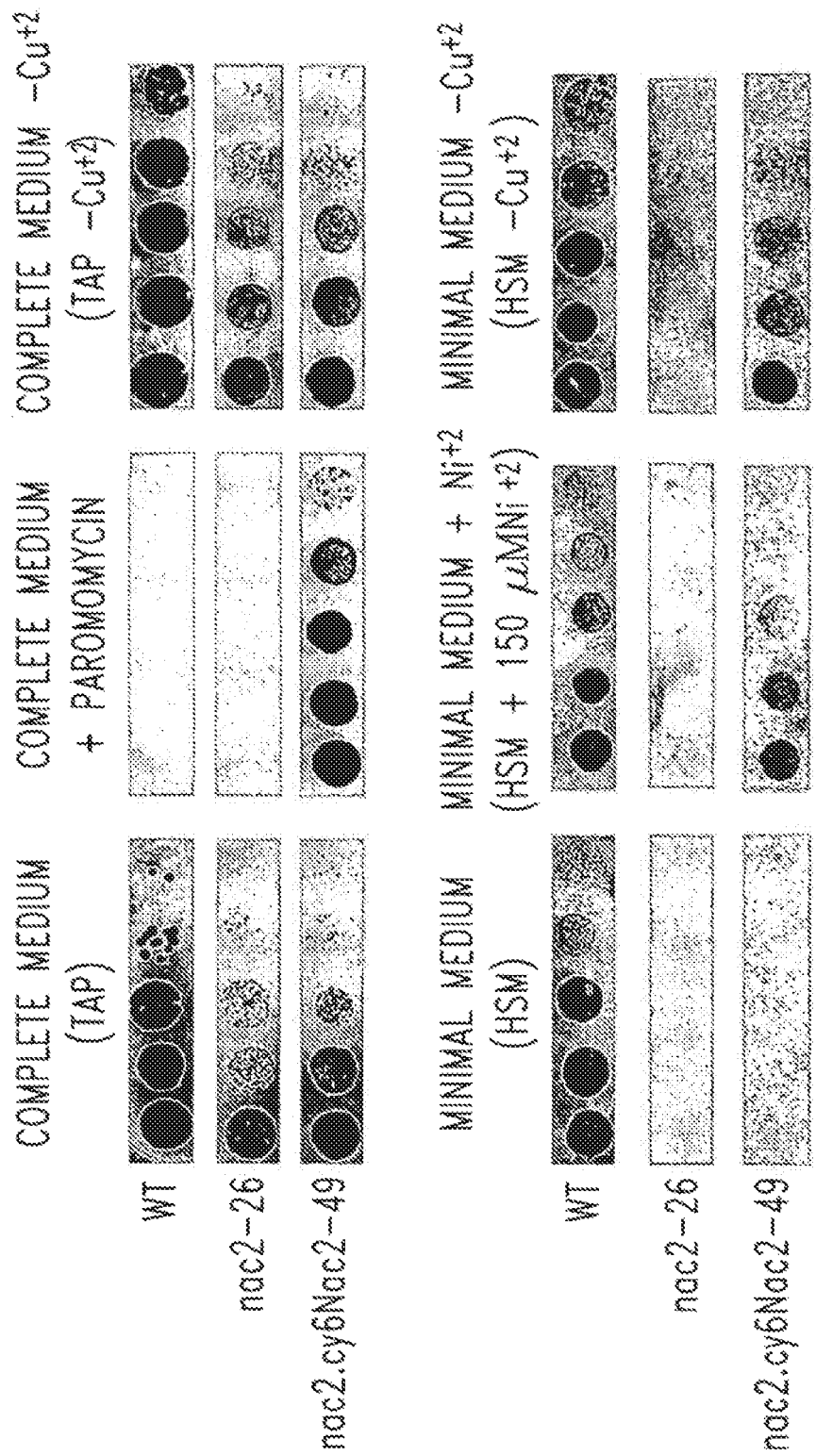
FIG. 13 shows the growth properties of the cy6Nac2.49 transgenic strain.

Using this regimen, the transgenic strain cy6Nac2.49 was isolated (see FIG. 13). This strain was capable of growing photoautrophically on HSM-$Cu^{+2}$ but, was unable to grow phototrophically on HSM supplemented with copper. The resulting strain, cy6Nac2.49, grows in two ways including 1.) photo-autotrophically in medium lacking copper or 2.) in anaerobically grown cultures when oxygen and copper are present in the growth medium where the cells lack PSII complexes (see FIG. 1). Thus, in the transgenic strain, cy6Nac2.49, the production of photosynthetic oxygen is controlled through a nuclear promoter, which responds to hypoxia.

Furthermore, sealed cultures of cy6Nac2.49 grown under non-inducing conditions will quickly become anaerobic, because photosynthetic oxygen is not released but oxygen consumption by mitochondrial respiration remains constant. In sealed cultures of cy6Nac2.49, a feedback inhibition loop exists where hypoxia induces photosynthetic oxygen production, which then re-represses PSII synthesis and photosynthetic oxygen evolution.

In fact, this is exactly what was observed when sealed illuminated cultures of cy6Nac2.49 were grown in complete medium. Initially, the oxygen content of the culture was present at atmospheric levels, and then it was quickly consumed, resulting in anaerobis and induction of hydrogen evolution. After a period of anaerobic growth, oxygen returned to the culture at 2 times the atmospheric levels inside the vessel, inhibiting hydrogen evolution (data not shown). In a conventional sealed vessel, only one cycle of oxygen consumption and hydrogen production was observed, possibly because the consumption of oxygen ceased when the reduced carbon was consumed by mitochondrial respiration while photosynthetic oxygen production remained constant.

Figure 10:
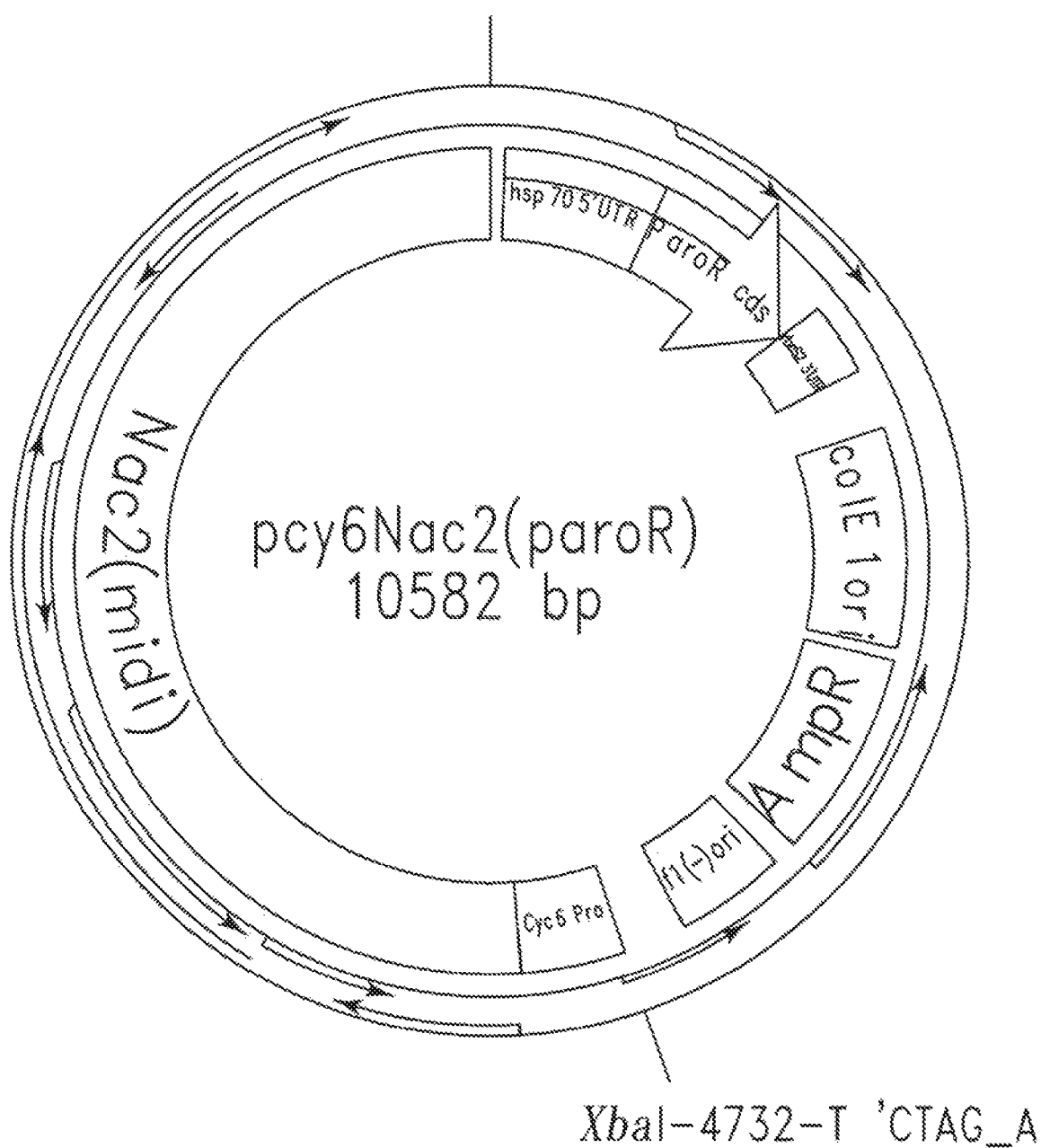
FIG. 10 shows a schematic of cy6Nac2(paroR).
Figure 14:
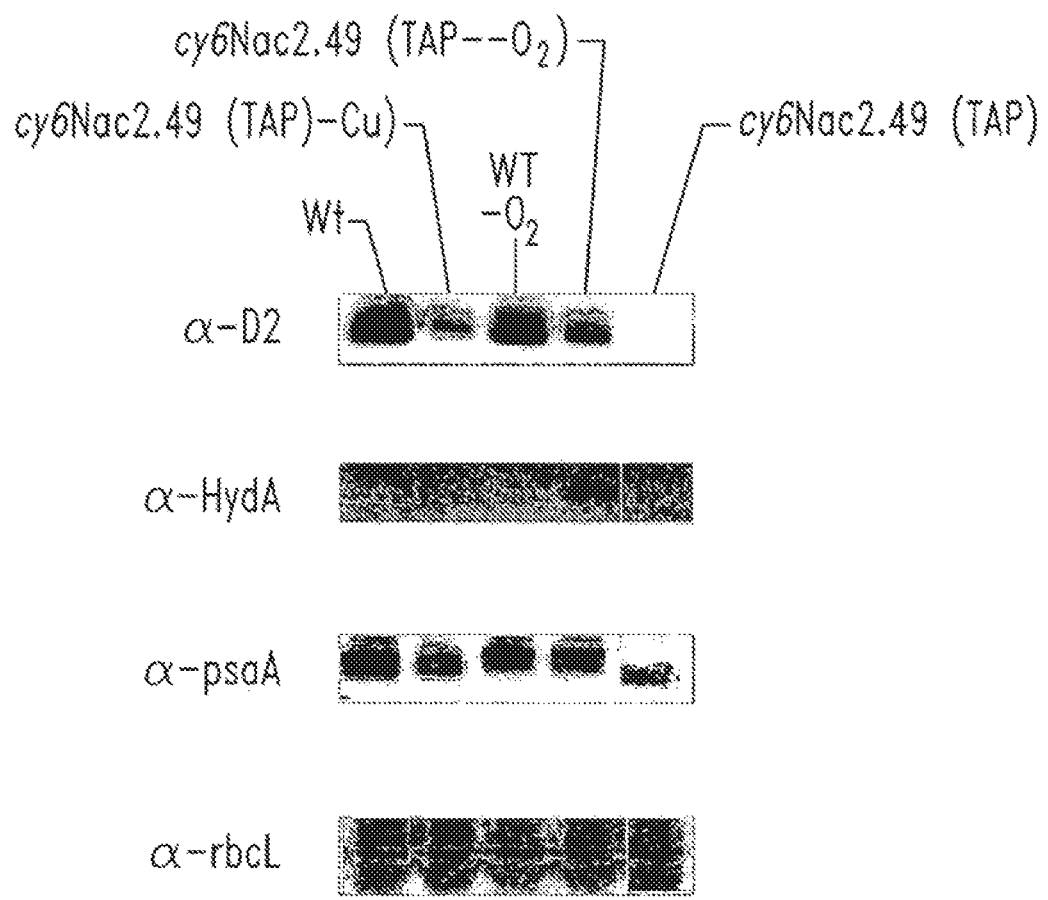
FIG. 14 shows Western blot analysis of the cy6Nac2.49 transgenic strain.

Wild-type, nac2-26 (the parental strain of cy6Nac2.49) and, cy6Nac2.49 cells were tested for their ability to grow on complete (TAP) medium, complete medium supplemented with the antibiotic paromomycin (TAP+Paro), minimal medium (HSM), and minimal medium lacking copper (HSM-$Cu^{+2}$) (FIG. 10). Western blot analysis performed on whole cell extracts of wild-type and cy6Nac2.49 cells grown in non-inducing (TAP) and inducing conditions (TAP-$Cu^{+2}$ and TAP-$O_2$) is shown in FIG. 14. Western blots were probed with antibody recognizing ?-HydA as a control for anaerobiosis, ?-D2 and ?-RbcL.

Figure 15:
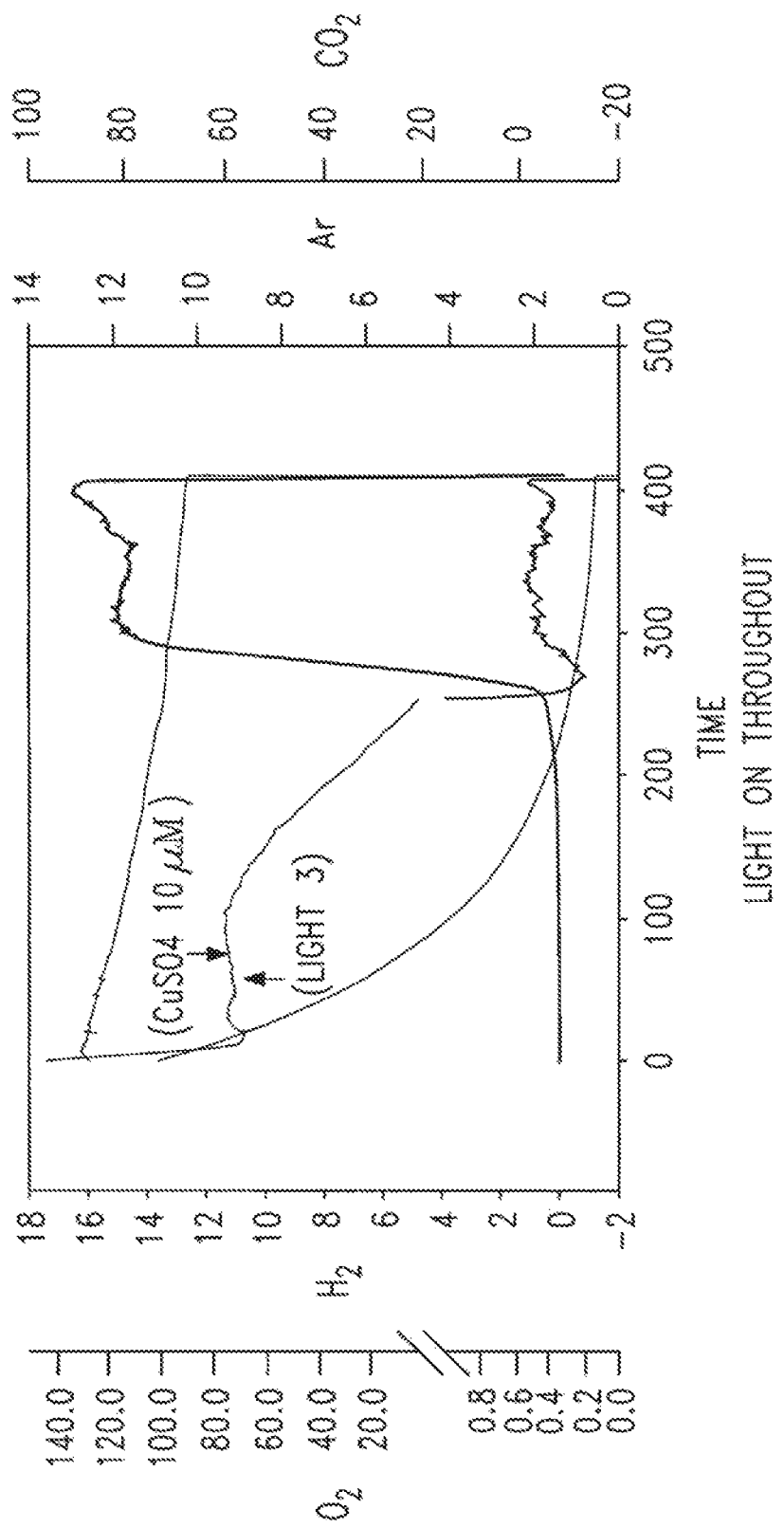
FIG. 15 shows the hydrogen production of the cy6Nac2.49 transgenic strain.

FIG. 15 shows the result of an experiment to measure hydrogen evolution. Cy6Nac2.49 cells were sealed in an illuminated vessel where dissolved gas in the culture medium could be measured using a mass spectrometer (oxygen-dashed line, hydrogen-solid line), then shifted from inducing to non-inducing conditions through the addition of copper to the growth medium (TAP-$Cu^{+2}$ to TAP). The concentration of $H_2$ was measured in the liquid phase and is indicated in mBar.

Conventional sealed vessels are not adequate to sustain hydrogen production using the transgenic strain cy6Nac2.49, so a sealed, anoxic system was designed to provide fresh, oxygen-depleted medium at a constant rate to a growing cy6Nac2.49 culture, to maintain it in exponential growth phase (see FIGS. 7 and 8). It was hypothesized that maintaining a culture in an exponential growth phase would result in the establishment of a cycle of oxygen consumptionlhydrogen productionloxygen production. When cells of cy6Nac2.49 were grown in this system, we observed an induction of hydrogen evolution shortly after the onset of hypoxia to the culture. Synthesis of PSII complexes was then induced along with a slight rise in oxygen in the vessel. Unlike the conventional sealed vessels, the photosynthetic oxygen released does not inhibit hydrogen production, presumably because photosynthetic oxygen production never exceeds the consumption of oxygen by mitochondrial respiration. In this system, the production of hydrogen is directly linked to light energy and therefore represents a direct biophotolysis method for the production of hydrogen. Using the anoxic system, we achieved a constant rate of hydrogen evolution reaching approximately 0.5% of the gas phase.

Oxygen is evolved as a byproduct of photosynthesis. As a result, a central challenge to sustaining algal hydrogen evolution using light energy (a process sometimes known as biophotolysis) has been to overcome oxygen sensitivity of the hydrogenase enzyme. In contrast to the direct biophotolysis method developed by these inventors, indirect biophotolysis methods (or two-stage photosynthesis and hydrogen production) apply spatial orland temporal separation of the photosynthetic oxygen and hydrogen production to overcome the oxygen-sensitivity of the hydrogenase enzyme (Benemann 1996; Melis 2000). The first stage involves normal oxygenic photosynthesis: the release of oxygen, fixation of $CO_2$, and accumulation of biomass. In the second phase, oxygenic photosynthesis is inhibited physiologically through the depletion of an important nutrient such as sulfur. Because rates of oxygenic photosynthesis decline drastically after about 22 hours of sulfur starvation, sealed cultures become anaerobic owing to the net consumption of oxygen caused by mitochondrial respiration (Melis 2000). Once anaerobia is established, the hydrogenase pathway is induced and hydrogen is evolved using electrons derived primarily from the remaining photo-oxidation of water, but also from the catabolism of endogenous substrates such as protein and starch (Ghirardi 2000).

The differences between the anoxic system, a direct biophotolysis method, and indirect biophotolysis methods reveals several important advantages for the use of the anoxic system. First, inherent to the anoxic system, there is a 50% gain in capacity for hydrogen production simply because oxygen and hydrogen production occur in a single illuminated sealed vessel. The two-stage photosynthesis and hydrogen production method or indirect biophotolysis implies the temporal andlor spatial separation of the oxygen and hydrogen production phases and as a result, requires two vessels with one of the vessels not being used during hydrogen production with a loss of 50% of capacity for production. Secondly, two-stage photosynthesis and hydrogen production methods rely on physiological depletion of sulfur to inhibit oxygenic photosynthesis. Severe sulfur starvation has a wide range of effects on a variety of cellular processes. The hydrogenase enzyme that catalyzes the release of hydrogen contains Fe—S clusters, assembly of which is required for its function (Posewitz, et al. (2004)). In addition, sulfur depletion negatively affects other important chloroplast complexes important to hydrogen evolution like PSI. Clearly, physiological depletion of sulfur severely affects important parts of the hydrogen evolution machinery. In contrast, the anoxic system does not rely on depletion of an important micronutrient to induce hydrogen production. In fact, hydrogen production occurs under optimum physiological conditions (in an exponentially growing culture in complete medium).

Finally, a major hurdle in the large-scale production of hydrogen using, for example, algae is providing light-energy to large dense cultures. In large dense cultures of algae, large quantities of chlorophyll in the light-harvesting complexes can prevent light energy from reaching cells at the center of the vessel. In our direct biophotolysis method, hydrogen production occurs in a system, where an optimum cell density can be established for maximum light absorption and hydrogen production.

EXAMPLE 2

Inducible Plastid Expression System for a Foreign Gene

Figure 16:
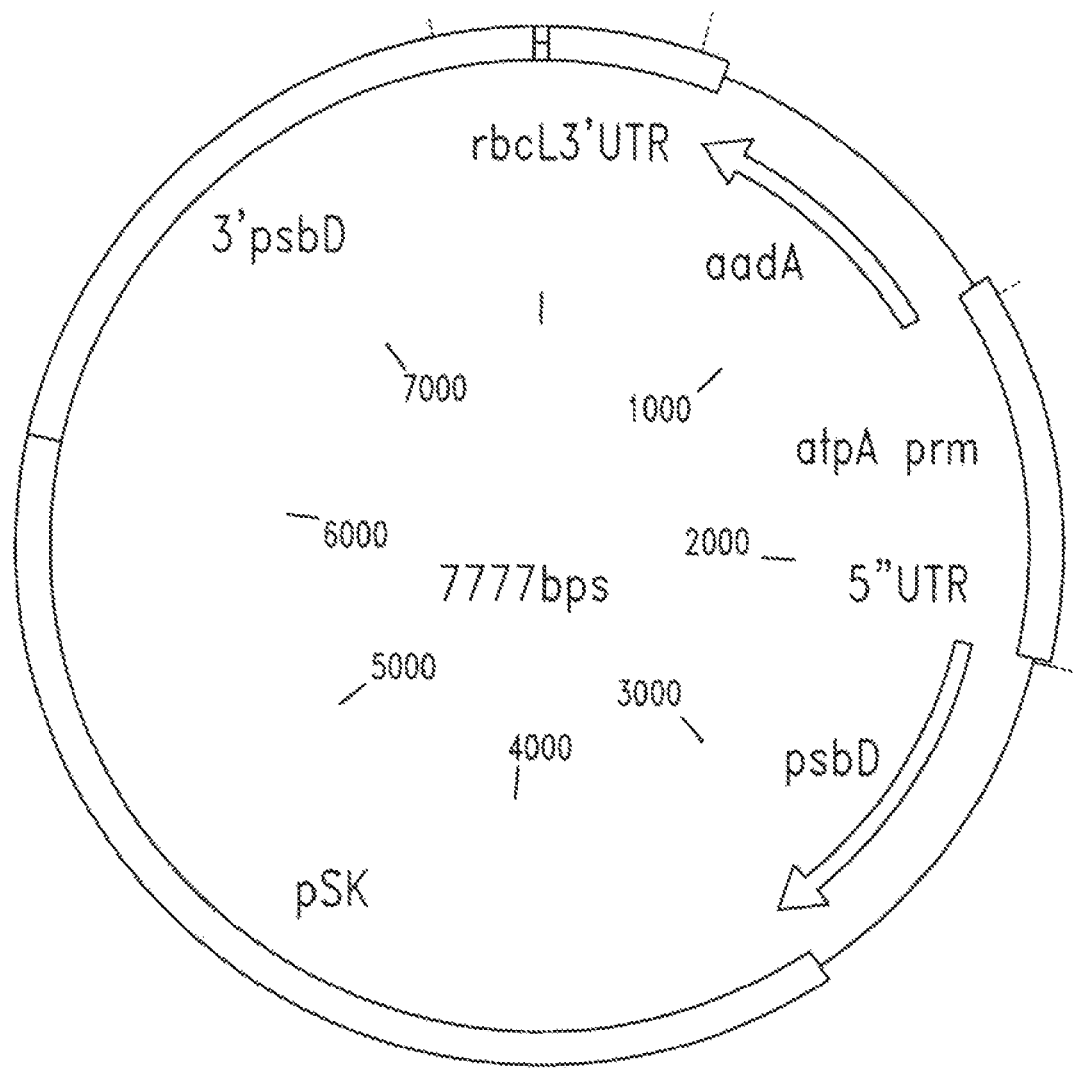
FIG. 16 shows a map of the pSK108 vector. The pSK108 vector has flanking chloroplast DNA to direct it to the region surrounding the psbD gene.

Chloroplast transformation vector. The plasmid pSK108 contains a 3 kb fragment of chloroplast DNA which includes the psbD gene and 5' flanking sequences to direct it to the region surrounding the psbD gene (FIG. 16). The construct also contains the aadA cassette inserted upstream of the psbD gene. A transgene can be inserted in frame using the NcoI and SphI sites of pSK108. Once ligated, the new vector would contain the transgene (plus 3 bps) with the 5' end of atpA driving its expression and the 3' sequence of rbcL acting as a terminator. The atpA promoter drives the expression of a gene encoding the ATP-generating proton pump of the chloroplast, and, thus, is not subject to the D1 repair mechanism.

Figure 17:
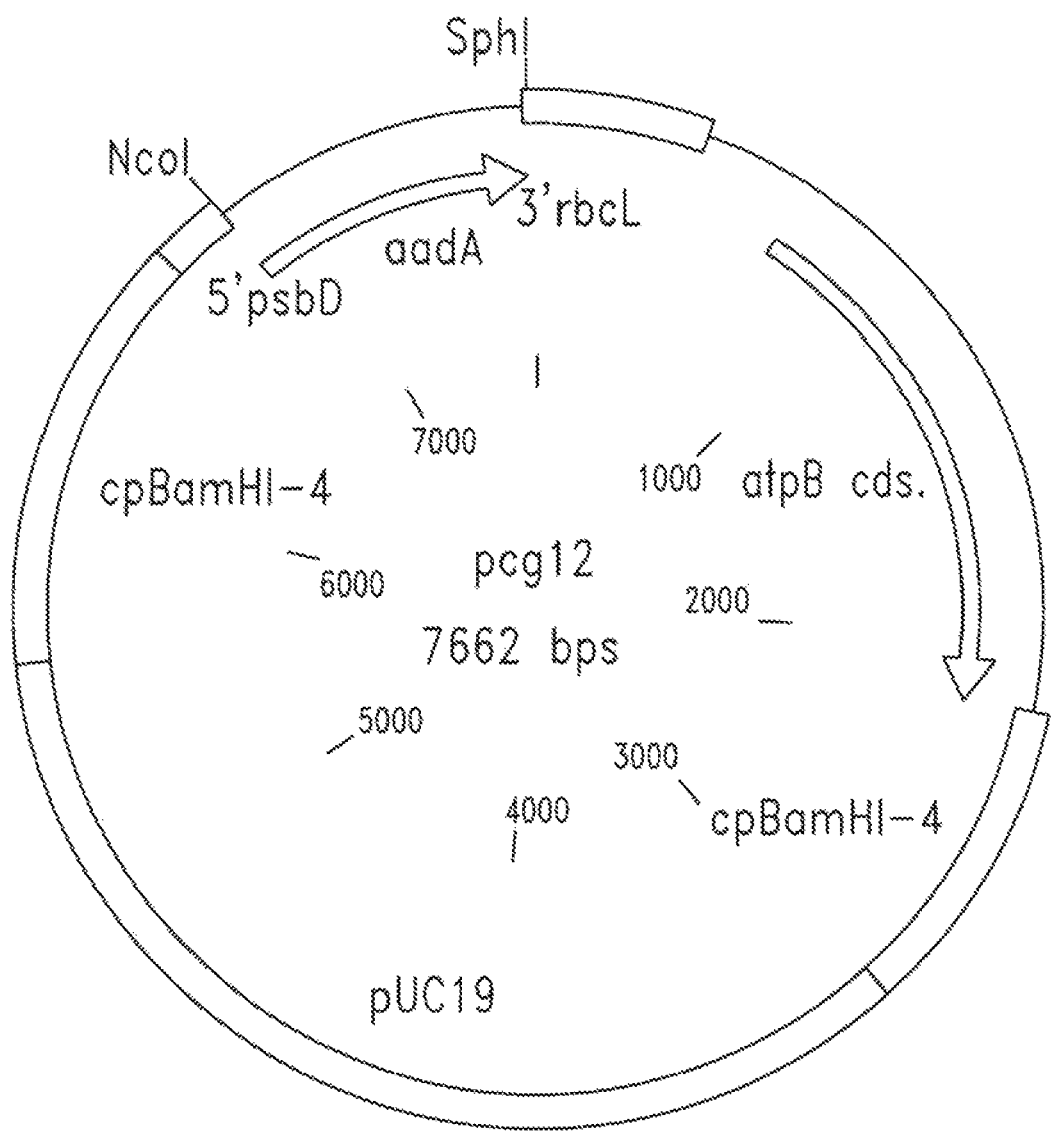
FIG. 17 shows a map of pcg12.
Figure 18:
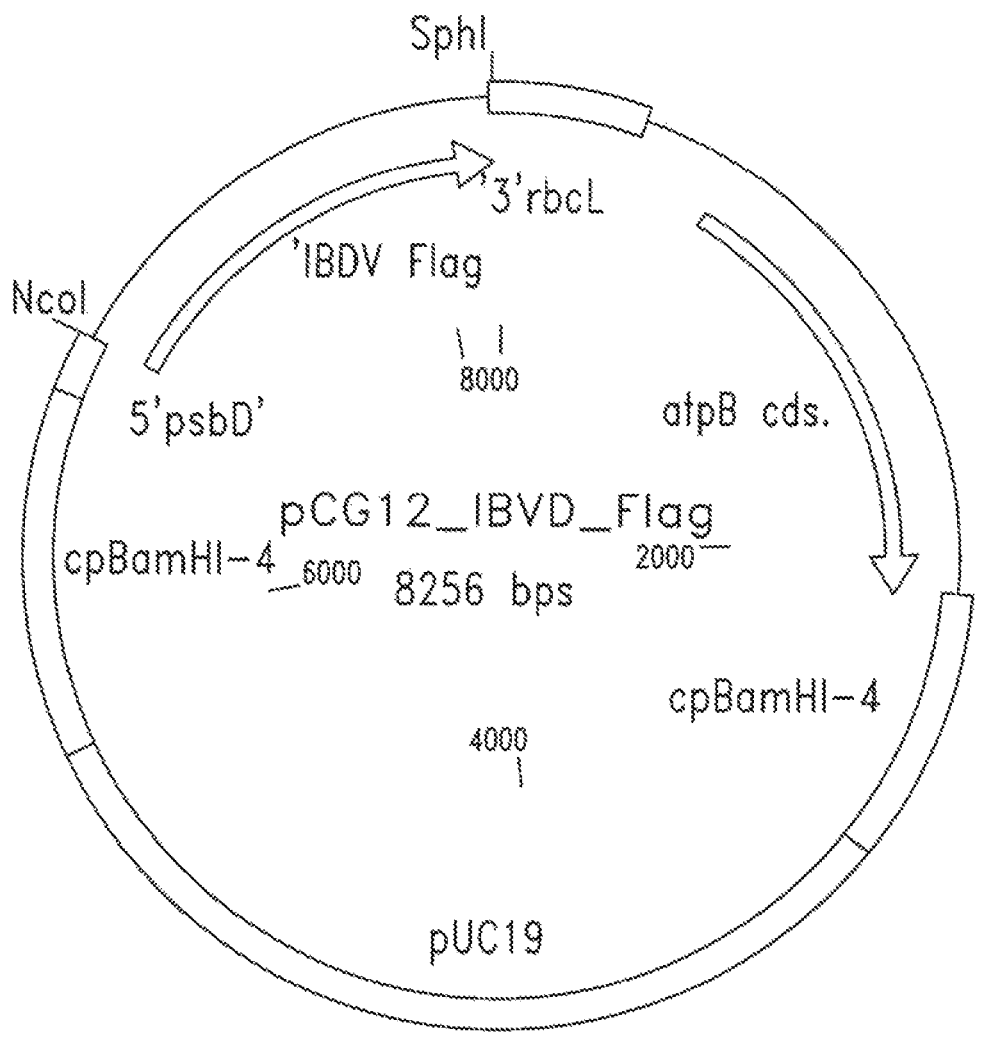
Figure 19:
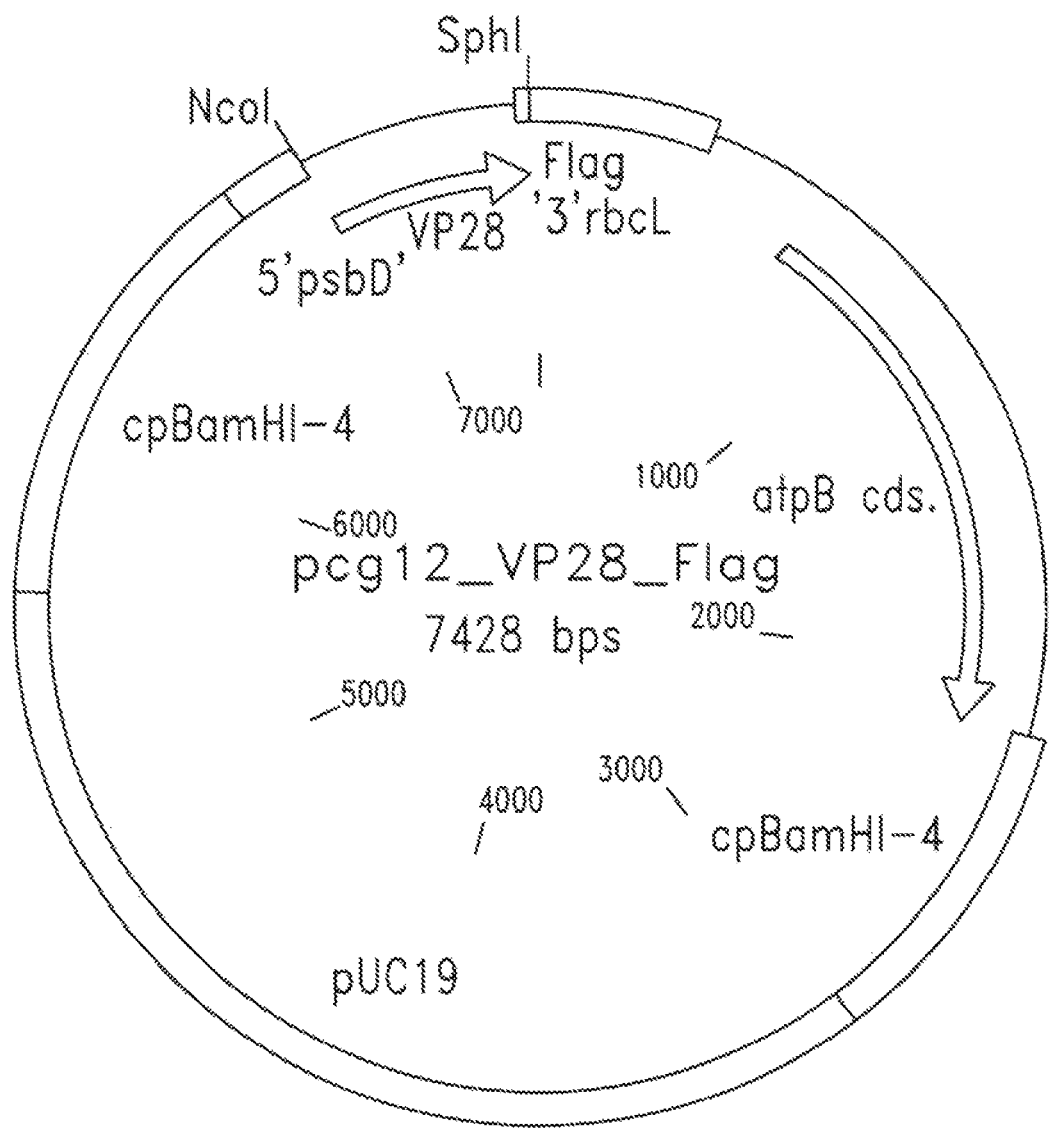
FIG. 19 shows a map of the chloroplast expression plasmid pcg12 VP28 Flag.

Three FLAG-tagged foreign genes wVP28, DILP, and IBVD were individually subcloned into the chloroplast transformation and expression vector pCG12 (FIG. 17). The vector integrates downstream of the atpB chloroplast locus. The transgenes are driven by the atpA promoter and carry the stability factor association site of the 5' UTR of psbD (FIGS. 18 and 19).

These vectors were co-transformed with the p228 vector, which carries the 16S rRNA gene of *Chlamydomonas* and confers resistance to spectinomycin, into the cyc6/Nac2 inducible strain (Cyc6 promoter as the control promoter and Nac2 as the stability factor).

EXAMPLE 3

Overexpression of the Hyda1, HydEF, and HydG Genes In *C. Reinhardtii* Chloroplasts Whether hydrogenases can be overexpressed in *C. reinhardtii* and whether this leads to enhanced hydrogen production will be tested. Recent experiments have shown that coexpression of HydEF, HydG and HydA1 in *E. coli* is sufficient for producing active Fe hydrogenase (Posewitz, et al, (2004)).

Overexpression of proteins in the nuclear compartment of *C. reinhardtii* has met with little success mostly because transgenes are often silenced. Therefore, these genes will be expressed in the chloroplast compartment using biolistic transformation. There are several advantages for using this strategy. First, gene silencing does not occur in the chloroplast. Second, each plastid gene is present in 80 copies in *C. reinhardtii*. Third, recent experiments have shown that it is indeed possible to achieve high expression levels of foreign proteins in the chloroplast if these genes are driven by chloroplast promoters, 5' and 3' UTRs, and if the coding sequence is resynthesized using biased chloroplast codon usage (Mayfield, et al. (2001)). There is a strong AT bias for chloroplast genes.

Each of the coding sequences of HydA1, HydEF and HydG will first be reconstructed taking into account the chloroplast codon usage of *C. reinhardtii*. This will be achieved by using published methods which have been used successfully for synthesizing foreign genes for expression in the chloroplast. As an example, we have recently successfully overexpressed two viral proteins in the chloroplast of *C. reinhardtii* (see below). The transgene will be inserted in the chloroplast inverted repeat so as to increase its copy number twofold. As a host strain, the cyc6Nac2 strain will be used. This strain contains the nuclear nac2 mutation and the Nac2 gene driven by the Cyc6 promoter which is induced by copper depletion or anaerobic conditions.

At this time it is not known which protein among the HydA1p, HydEFp and HydGp proteins is limiting for hydrogen production. To test this, each of the three genes fused to the psbD promoter and 5' UTR will first be inserted individually within the chloroplast inverted repeat using biolistic transformation for overexpression. One possibility is to insert the gene in the ribosomal operon within the spacer between the 16S and 23S rRNA genes, a strategy which has been used successfully for high expression in the chloroplasts of higher plants. Because the transgene is under control of the psbD 5' UTR which is driven via Nac2 by the Cyc6 promoter, the transgene will only be expressed under anaerobic conditions. Expression will be monitored by RNA blot hybridizations or real time RT-PCR. For each of the three genes tested, hydrogen production will be assayed by growing the transformed cells in a closed bottle connected with a tubing to an upside-down burette filled with water and by measuring the volume of the gas directly from the volume of water that is displaced as described by Zhang and Melis (2002). If hydrogen production is increased relative to the cyc6Nac2 control, this will indicate that the overexpressed protein is limiting. If these experiments reveal that more than one of these proteins is limiting for hydrogen production, both proteins will be expressed using the same strategy. It is possible that expression of these three proteins is adjusted in wild-type cells so that each protein needs to be overexpressed to increase the yield of hydrogen production. In this case overexpresson of the three proteins will be required. Expression of multiple transgenes has been achieved in higher plant chloroplasts (Quesada-Vargas, et al. (2005)). If expression with the psbD 5'UTR is not sufficient, other strong chloroplast promoters-5'UTRs such as psbA, atpA and the ribosomal promoter will be tested.

EXAMPLE 4

Expression of Genes that Affect Hydrogen Production

In addition to the above, several other genes will be tested for increased hydrogen production using the inducible and-lor repressible system for the expression of proteins in plastids. Two examples are oxygen-insensitive hydrogenases or reducing antenna size (Melias, et al. (2004); Ghirardi, et al. (2005)). Briefly, the former involves cloning and characterizing native and mutagenized hydrogenase genes from *Chlamydomonas* and other organisms for reduced sensitivity to oxygen. The objective of the latter, antenna reduction, is to reduce the amount of photons captured by algal cells, so that light may penetrate deeper into photoreactors, thus becoming available for use by normally shaded cells. Algal cells are very effective at capturing but not utilizing light, wasting as much as 80% of absorbed photons. Genes that regulate antenna size have been identified through DNA insertional mutagenesis. The PSII and PSI antenna size of mutant, tla1, was 50% and 65% of the wild type strain. Finally, mutants strains have been identified with presumably increased rates of respiration that consequently lower the levels of oxygen available for inhibiting hydrogenases (Krause, et al. (2005)). The genes will be inserted into the cy6Nac2.49 transgenic strain and evaluated for their contribution to increasing hydrogen production of the strain.

One important limiting factor for hydrogen production is the competition with the Calvin-Benson cycle. One possibility to enhance electron flow to the hydrogenase is to decrease the activity of the Calvin-Benson cycle by decreasing the amount of an enzyme which participates in this cycle. For example, phosphoribulose kinase (PRK) could be utilized because two mutants of *Chlamydomonas*, F60 and ac214, deficient in PRK activity are available. The PRK gene will be fused to the inducible Cyc6 promoter and this construct will be inserted into F60. The advantage of this strategy is that PSII and the Calvin-Benson cycle will be operational together in the absence of copper (or oxygen) thus allowing for storage of reducing power. Both genes will be shut off in the presence of copper (or oxygen). Thus, under conditions in which hydrogenase is induced, electron flow will be diverted from the Calvin-Benson cycle to the hydrogenase and hydrogen production will be enhanced.

In another illustrative embodiment, PRK temperature-sensitive mutants will be screened for. In this way the Calvin-Benson cycle can be shut off at the restrictive temperature and electrons diverted to the hydrogenase. The PRK mutants will be transformed with a library of mutagenized PRK genes generated by PCR. Transformants will be selected on minimal medium at the permissive temperature (24° C.). Colonies will be replica-plated to minimal medium and will be grown at the restrictive temperature (32° C.) and mutants unable to grow will be identified. To verify that the PRK gene carries a mutation, the gene will be amplified by PCR and sequenced. It will also be possible to screen the mutants by fluorescence since a block in the Calvin-cycle is likely to increase the fluorescence yield of these mutants.

In another embodiment, cyclic electron flow represents another route of diversion of electrons from the hydrogenase, and we will use mutants deficient in state transitions that are blocked in state 1. State transitions involve a rebalancing of the light excitation energy between the antenna of PSII (LHCII) and PSI through a reversible displacement of the mobile part of LHCII from PSII to PSI under changing light conditions which allows for an optimal photosynthetic yield. In state 1, the mobile part of LHCII is associated with PSII, whereas in state 2 it is associated with PSI. Moreover, in *Chlamydomonas*, state 1 favors mostly linear electron flow while state 2 leads to cyclic electron flow (Finazzi et al., 2002). Thus, there is no cyclic electron flow in mutants blocked in state 1. The stt7 mutant which is known to be blocked in state 1 (Depege et al., 2003) will be crossed with nac2-26 containing the Cyc6-Nac2 and Cyc6-PRK construct and it will be determined whether this leads to improved hydrogen production when PSII activity is repressed. Alternatively, once the temperature-sensitive PRK mutants are available, the mutations will be crossed to the nac2-26 stt7 Cyc6-Nac2 strain. These strains will be tested for hydrogen production under the conditions described above.

Other mutants besides stt7 deficient in state transitions will be analyzed. The analysis of these mutants is of particular interest because alterations in state transitions can be caused indirectly by alterations in the regulation of photosynthetic and mitochondrial electron flow which may change the ratio of mitochondrial respiration relative to photosynthetic oxygen evolution. Mutants of this sort have already been reported to have increased hydrogen production in comparison to WT cells (Kruse et al., 2005).

EXAMPLE 5

Inducible Plastid Expression System for Foreign Genes

The selectable marker gene, aadA, was used for inducible chloroplast gene expression. It can be expressed in a Nac2-dependent fashion, can be easily screened using the antibiotic spectinomycin, and it is known to have a high specific activity. Even low aadA expression results in some antibiotic resistance, and therefore provides a measure for the "tightness" of cy6Nac2 regulation in Ind41_18 (described below).

A chloroplast integration vector had been constructed that carries the promoter and 5'UTR of psbD driving the expression of the aadA gene.

The nac2-26 mutant strain was previously described (Kuchka, et al. EMBO J. 7, 319-324; Nickelsen, et al. EMBO J. 13, 3182-3191). The cyc6Nac2.49 strain contains a trans-gene consisting of the Cyc6 promoter fused to the Nac2 midi-gene inserted into the nuclear genome of the nac2-26 mutant (? nac2::cy6proNac2). Ind41 was derived from cy6Nac2.49 by replacing the psbD promoter and 5'UTR with a 675 fragment containing the petA promoter and 5'UTR (? nac2::cy6pro Nac2::5'petA-psbD). Ind41-18 is related to the Ind41 strain, except that the aadA cassette in the Ind41-18 strain has been completely excised from the chloroplast DNA and the strain is therefore sensitive to spectinomycin (? nac2::cy6proNac2::5'petA-psb[Spc$^s$]). Ind_aadA_117 was derived from Ind41-18 and contains the aadA cassette driven by the psbD promoter and 5'UTR inserted downstream of the atpB gene (? nac2::cy6proNac2::5'petA-psbD::5'psbD-aadA).

Screening for Ind_aadA transgenic strains

Integration of the 5' psbD-aadA cassette into the chloroplast genome of Ind41_18 cells was accomplished through biolistic transformation of copper-starved Ind41_18 cells with the pcg12 chloroplast integration vector (FIG. 21). Selection of the transformants was on copper-depleted TAP medium containing 100 ? g/ml spectinomycin. Colonies resulting from the transformation were picked and re-plated three times on TAP-$Cu^{+2}$ medium supplemented with 100 ? g/ml spectinomycin to ensure complete segregation of the 5'psbD-aadA cassette.

A schematic diagram of the pcg12 vector used in the experiment is shown in FIG. 21. The aadA cassette in the vector is expressed using the psbD 5' UTR. Growth of wild type, Ind41_18, and Ind_aadA_X transgenic strains is also shown. The strains were serially diluted, then spotted on solid TAP, copper-depleted TAP media (TAP-$Cu^{+2}$), TAP supplemented with 100-1000 µg/ml spectinomycin (TAP-$Cu^{+2}$+Spc), and TAP-$Cu^{+2}$ supplemented with 100-1000 µg/ml spectinomycin (TAP-$Cu^{+2}$+Spc) and cultured for 7-10 days at a light intensity of 100 µE $m^{-2}s^{-1}$.

Figure 21A:
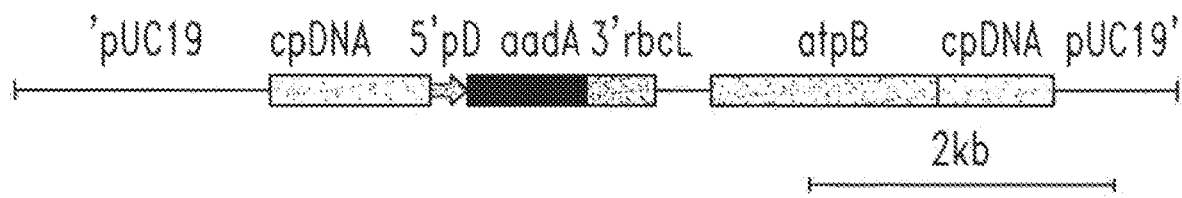
FIG. 21A-FIG. 21B shows isolation of IND_aadA_X transgenic strains and growth on various media.
Figure 21B:
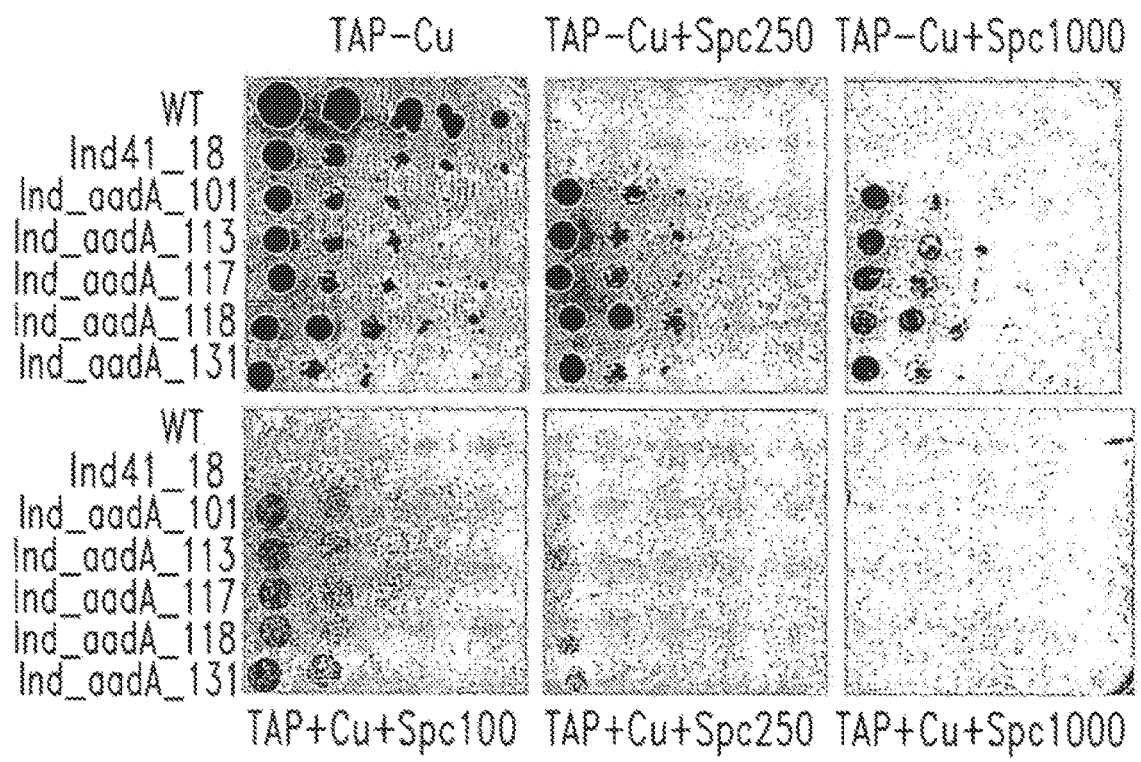

Screening of transformants was accomplished by replica plating the putative inducible aadA transgenic lines on TAP+Spc100 and TAP-$Cu^{+2}$+Spc100 solid agar medium. All of the colonies tested grew equally well on both culture media, indicating a loss of promoter control of the Cyc6Nac2 transgene in these strains (FIG. 21A). However, when higher concentrations of spectinomycin were tested, 85% of the strains tested were sensitive to spectinomycin when copper was supplemented in the growth medium, but not when copper was omitted from the medium (FIG. 21B). Several of these strains, named Ind_aadA, were chosen for further characterization. The genotype of these strains is nac2::cy6proNac2::5'petA-psbD::5'psbD-aadA.

Growth analysis of Ind_aadA transgenic strains

Growth analysis of several inducible strains retained from the initial screening process was accomplished by serial diluting, then spotting wild-type, Ind41_18 and Ind_aadA cells on either TAP, TAP-$Cu^{+2}$, HSM, HSM-$Cu^{+2}$ and solid agar medium supplemented with a range of spectinomycin concentrations (0, 100, 250, 500, 750, 1000, 2000 ? g/ml) (FIG. 21B). Of the 11 strains tested in this fashion one, Ind_aadA_36 was capable of growing on TAP medium supplemented with >500 μg/ml spectinomycin. On the other hand, 6 of 11 strains tested were able to grow on copper-depleted TAP medium at low spectinomycin concentrations but could not grow with spectinomycin concentrations above 250 μg/ml (FIG. 21B). One strain named Ind_aadA_117 was sensitive to spectinomycin when cultured on TAP+250 μg/ml spectinomycin, but was capable of growing on copper-depleted TAP medium at all concentrations of spectinomycin tested.

Northern analysis of total RNA extracted from Ind_aadA_117

Figure 22:
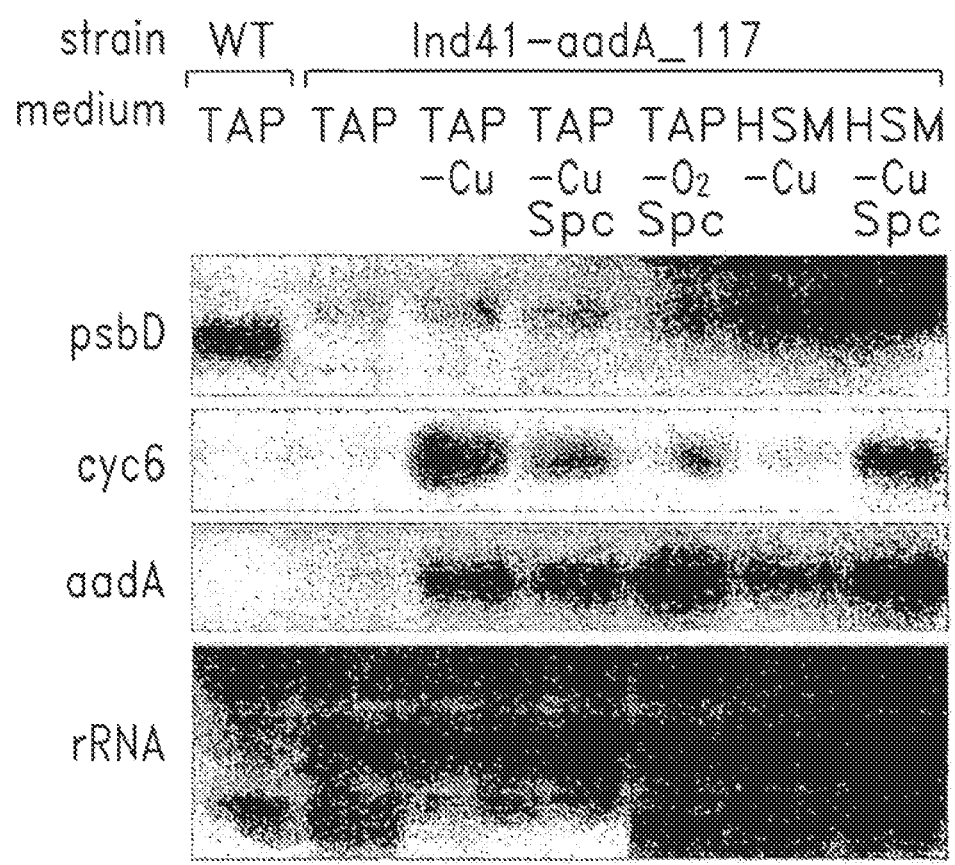
FIG. 22 shows Northern blot analysis of total RNA extracted from wild-type and isolation of IND_aadA_117.

To gain insight into the induction of aadA expression in Ind_aadA_117, total RNA was isolated from Ind_aadA_117 cells cultured in either non-inducing (TAP) or inducing conditions (TAP-$Cu^{+2}$, TAP-$Cu^{+2}$+Spc, TAP-$O_2$, HSM-$Cu^{+2}$). Northern analysis of these samples revealed that psbD transcripts accumulated to the same levels as was described for the parental strain, Ind41_18 or approx. 25% of the wild-type psbD RNA. As expected, the psbD RNA of Ind_aadA_117 was larger than wild-type psbD transcripts, indicating that the authentic psbD gene is no longer present in this strain, a characteristic inherited from the parental strain, Ind41_18 (FIG. 22). Importantly, accumulation of aadA transcripts was observed in all cultures in which Cyc6 transcription was induced (FIG. 22). The "leaky" phenotype of the Ind_aadA strains was confirmed by the presence of a small amount of aadA RNA in TAP grown Ind_aadA_117 cultures (FIG. 22). Surprisingly, aadA transcripts were more abundant in anaerobically grown cultures than copper-starved cultures of Ind_aadA_117, a characteristic not shared by the "grand-parental" strain cy6Nac2.49 with respect to psbD/D2 expression (FIG. 22). In the assay shown in FIG. 22, total RNA was extracted from wild-type, and Ind_aadA_117 cells cultured in TAP, TAP-$Cu^{+2}$, TAP-$Cu^{+2}$+Spc TAP-$O_2$+Spc, HSM-$Cu^{+2}$ and HSM-$Cu^{+2}$+Spc liquid media. Probes are indicated on the left in FIG. 22.

Analysis of Ind_aadA_117 protein extracts

Figure 23:
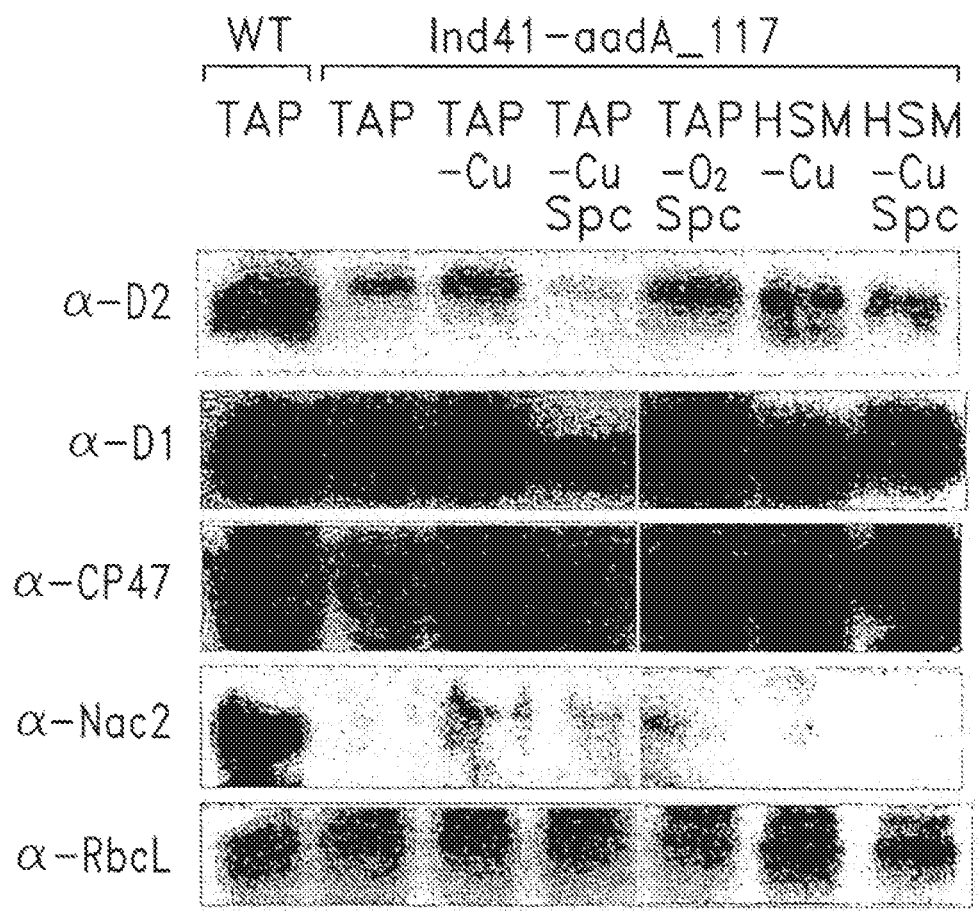
FIG. 23 shows analysis of total and soluble (α-Nac 2) extracted from wild type and IND_aadA_117.

Total proteins extracted from Ind_aadA_117 cells were analyzed by immunoblots using antisera specific for several important chloroplast-encoded proteins. D2 protein levels were found at approximately 25% of wild-type levels in all cultures of Ind_aadA_117 examined, less than in the parental strain Ind41_18 which accumulated 50% of D2 protein (FIG. 23). On the other hand, full restoration of D1 and CP47 protein accumulation was observed in most of the Ind_aadA_117 protein extracts tested and, in this case, D2 protein accumulation was estimated to be reduced by 75%. Therefore, surprisingly, D1 and CP47 accumulation was not adjusted to D2 protein levels. Nac2 protein accumulation in Ind_aadA_117 was determined using soluble extracts prepared from Ind_aadA_117 cultured under a variety of conditions. Induction of Cyc6Nac2 was observed in soluble extracts from anaerobic and copper-starved Ind_aadA_117, although, a small amount of Nac2 was detected in TAP grown Ind_aadA_117 cultures (FIG. 23). The presence of trace amounts of Nac2 in TAP cultures, a condition where the transcription of Cyc6 is repressed, demonstrated that the system was slightly "leaky" in the Ind_aadA strains (FIG. 23). Therefore, the initial observation that Ind_aadA transgenic strains cultured on TAP medium were able to grow in the presence of low concentrations of spectinomycin is due to some leakiness of Cyc6Nac2. In FIG. 23, total proteins were extracted from wild-type, and Ind_aadA_117 cells cultured in TAP, TAP-$Cu^{+2}$, TAP-Cu+2+Spc TAP-$O_{2+}$Spc, HSM-$Cu^{+2}$ and HSM-$Cu^{+2}$+Spc liquid media and were size fractionated and immobilized on PVDF membranes. Probes are indicated on the left of FIG. 23.

aadA assay of Ind_aadA_117

The amount of aadA was estimated indirectly by measuring its activity (Table 1). The assay is based on the ability of the aadA enzyme to transfer the adenyl moiety of an ATP molecule to spectinomycin, thereby adding a positive charge to the spectinomycin molecule. Positively charged spectinomycin molecules can bind a phospho-cellulose membrane that carries a negative charge. Thus, if crude extracts of Chlamydomonas expressing aadA are incubated in the presence of spectinomycin and $^{32}$P-labeled dATP, the amount of radioactivity present on the phospho-cellulose membranes after spotting the reactions and washing off the non-specific products provides a relative measure of the activity of the aadA enzyme. Crude extracts of Ind_aadA_117 cells cultured in either TAP, TAP-$Cu^{+2}$,TAP-$Cu^{+2}$+Spc liquid media were used to measure the aadA activity in this transgenic strain compared to the parental strain and another strain expressing the traditional aadA cassette in the wild-type background. The combined results of several independent assays are presented in Table 1. No aadA activity was detected in Ind41_18 thus demonstrating that the removal of the cassette in this strain is complete. On the other hand, aadA activity in both the wild-type strain expressing the traditional aadA cassette, and in Ind_aadA_117 grown in TAP-$Cu^{+2}$ and TAP-$O_2$ was similar to that previously reported for aadA-expressing transgenic strains (Table 1). A small but significant aadA activity was also present in crude extracts of Ind_aadA_117 cultured in TAP medium. This result confirmed, that a small amount of aadA activity was present in uninduced Ind_aadA_117, although the activity was only a fraction of the activity of induced cultures of Ind_aadA_117.

Screening for strains capable of inducing the expression of the aadA gene using the cy6Nac2 chloroplast inducible gene expression system consistently resulted in the recovery of strains that had a "leaky" phenotype. Because the Cyc6Nac2 transgene was demonstrated to be tightly regulated in the parental strain, de-repression of Cyc6Nac2 transgene in Ind_aadA was, by inference, considered a prerequisite for surviving the screening process. One possible explanation for this observation is that there was initially a very small amount of copper contamination in the copper-depleted medium used at each step in the screening process, including in the media used for the biolistic transformation of Ind41_18 with pcg12. If this was indeed the case, a transient repression of Cyc6 transcription would be predicted to occur until copper contamination dropped below $2 \times 10^6$ ions/cell, and as a result, only those transformants that de-repressed Cyc6Nac2 would survive the original transformation with the pcg12 plasmid. In other words, given that repression of Cyc6Nac2 transcription was long enough to negatively effect cell survival in spectinomycin-supplemented media; all colonies that survived the original transformation were generated from a single cell that would not have divided unless Cyc6Nac2 had been de-repressed. Contamination of the culture medium was considered to be unavoidable as it has been well documented that even minute concentrations of copper repress the transcription of Cyc6. Indeed experiments designed to study the kinetics of copper-mediated repression in cy6Nac2.49 revealed that re-suspension of copper-starved cy6Nac2.49 cells in copper-depleted media, transiently repressed Cyc6Nac2 transcription, as well as transcription of the authentic Cyc6 locus for 1-2 cycles of division.

Nevertheless, the Ind_aad_117 transgenic strain shows that the design for an inducible chloroplast gene expression system based on the nucleus-encoded Nac2 protein is possible for *Chlamydomonas*. The transgenic Ind41_18 strain can be used to induce the expression of any chimeric gene driven by the psbD 5'UTR integrated in the chloroplast genome, provided that the psbD 5' UTR is capable of driving the expression of the gene of interest.

For the assays in Table 1, aminoglycoside adenyl transferase activity in Ind41_aadA-117 was determined under inducing and repressing conditions. Extracts from WT-aadA, Ind41_18 and Ind41_aadA-117 strains were assayed for aadA activity and for total protein content. The activity is indicated as cpm incorporated per µg of protein. Numbers of independent measurements are indicated in parenthesis.

TABLE 1

| Strain | +Cu | −Cu |
|---|---|---|
| WT | 1.4 +/− 2.0 | nd |
| WT-aadA | 207.0 +/− 49.5 (3) | 192.6 +/− 51.4 (4) |
| Ind41_18 | 9.2 +/− 4.1 (4) | 12.2 +/− 7.9 (4) |
| Ind41_117 | 24.2 +/− 12.5 (4) | 274.3 +/− 90.6 (7) |

Inducible expression of the VP28_FLAG, IBVD_FLAG, and DILP_FLAG

To test if the inducible chloroplast gene expression system described here could be applied to the production of foreign proteins, three different foreign proteins were selected for heterologous expression using the 5' psbD driven transgenes, VP28, DILP, and IBVD. IBVD (or VP2) is used to generate a vaccine for the control of Infectious Bursal Disease Virus (IBDV) in poultry (Mundt 1995). VP28, the 23 kD fragment of a major structural envelope proteins of White spot syndrome virus of *Penaeus monodon*, was demonstrated to protect shrimp from infection when fed as a subunit vaccine (Witteveldt 2004).

Figure 24:
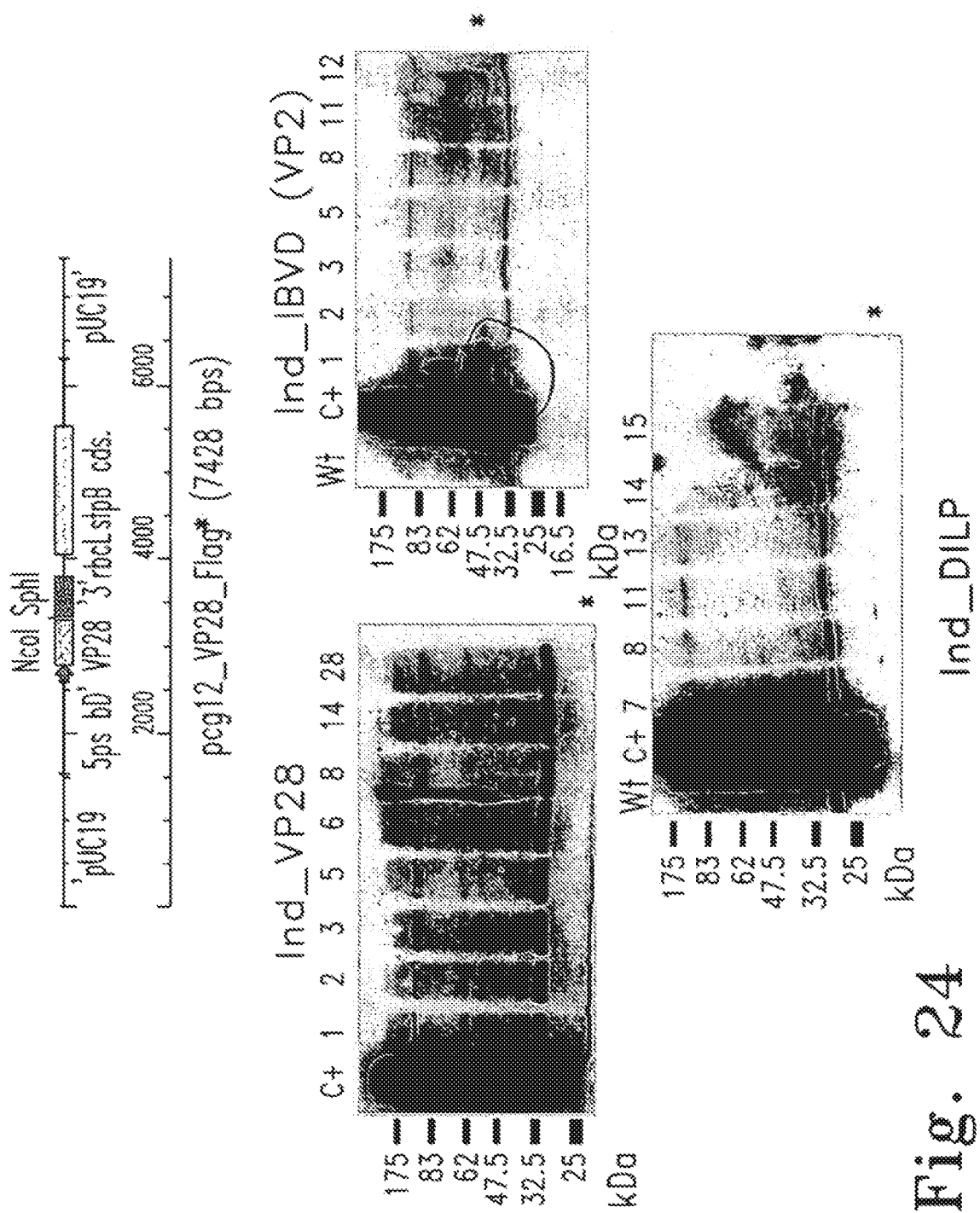
FIG. 24 shows screening for transgenic strains that induced the expression of three foreign proteins (DILP, IBVD, and VP28).

Three FLAG-tagged foreign genes VP28, DILP, and IBVD with a codon bias that was optimized for the *C. reinhardtii* chloroplast genetic machinery were provided as a gift from Dr. Stefan Surzycki (Indiana University, Bloomington) and were individually subcloned in the chloroplast transformation and expression vector pcg12 so that the 5'UTR of psbD was driving the expression of the foreign protein with the rbcL 3'UTR as a terminator (FIG. 24A). Because these new constructs lacked a selectable marker, the generation of transformants required co-transformation with another chloroplast integration vector carrying a selectable marker (FIG. 24A).

A schematic diagram of the pcg12_DILP vector used in experiments to induce the expression of *Drosophila* insulin-like peptide is shown in FIG. 24A. The black box represents DILP coding sequence. The arrow represents the 5' leader of the psbD gene. The asterisks indicate insertion of the 3HA-11 epitope. In FIG. 24B, immunoblots using total proteins extracted from Ind_VP28 (upper left), Ind_IBVD (upper right) or Ind_DILP (lower panel) are shown, probed with antibody that recognized the FLAG epitope. The predicted molecular weight of the proteins are VP28-23 kD, IBVD-49 kD, and DILP-12 kD and are indicated with an asterisk.

These vectors were co-transformed with the pY1_INT vector, which carries the ycf1 gene and flanking chloroplast sequence and the aadA cassette which confers resistance to spectinomycin into the Ind41_18 strain. Following selection on TAP plates amended with spectinomycin, putative transformants were tested for the presence of the gene using PCR with oligonucleotides that amplified the foreign gene. Of the 10 colonies tested by PCR for co-insertion of the transgene, seven were positive for VP28 and DILP and five were positive for the presence of the IBVD gene. These lines were named IndVP28_x, IndDILP_x and IndIBVD_x and had the genotype of nac2.Cyc6$_{pro}$ Nac2::5'petA-psbD::5'psbD-VP28/DILP/IBVD.

Colonies that tested positive for the insertion of the foreign gene in the chloroplast genome were tested for protein production using immunoblot analysis with the Flag® antibody following induction of the gene by copper starvation. Of the 22 transgenic lines tested in this way, 8 of 8 appeared to accumulate the VP28 protein, as a 23 kD protein was induced in extracts from IndVP28 that was not present in either the wild-type or the non-induced controls (FIG. 24B—Upper left). Total protein extracted from 4 of 6 IndDILP strains analyzed also accumulated a >25 kD protein when these cells were induced (FIG. 24B—Lower panel). A 50 kD protein accumulated in 3 of 7 IndIBVD strains assayed in this way (FIG. 24B—Upper right).

Figure 25:
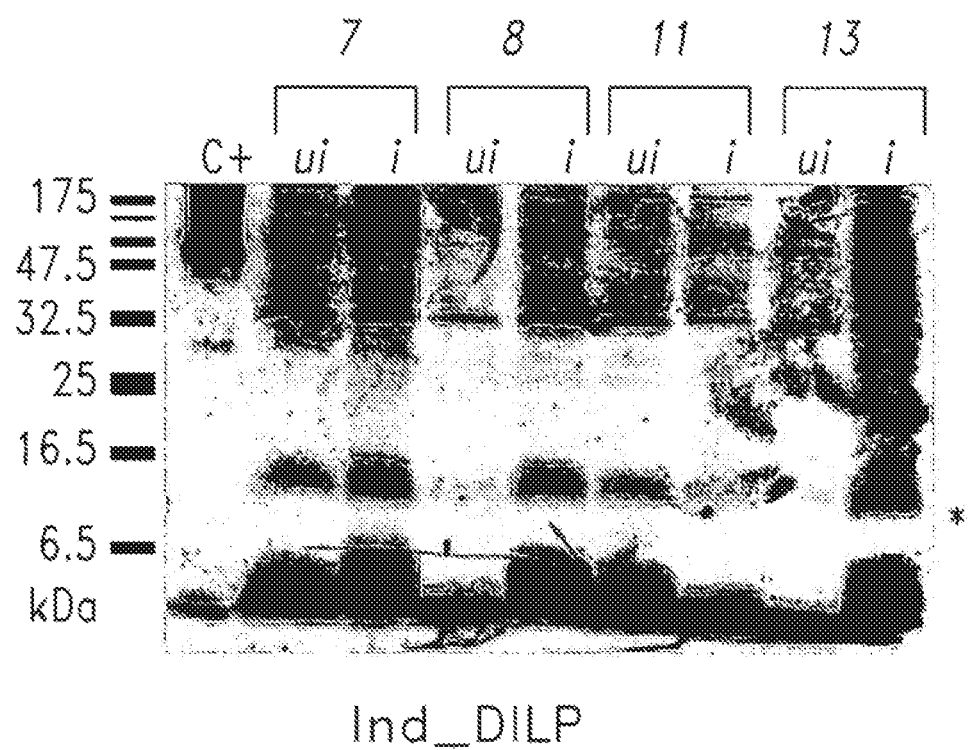
FIG. 25 shows inducible production of a foreign protein (DILP) using the Nac2 inducible chloroplast gene expression system.

FIG. 25 shows based on immunoblots with total proteins extracted from IndDILP strains that the expression of DIL-P_FLAG was induced in initial screening experiments. IndDILP strains were cultured in either TAP (ui) or TAP-Cu$^{+2}$ (i) liquid media supplemented with 50 µg/ml spectinomycin and size fractionated on 15% SDS-PAGE gels. The resulting immunoblots were then incubated with antibodies that recognized the FLAG epitope. Total proteins extracted from a transgenic strain that expressed a FLAG-tagged Alb3.1 protein were used as a positive control for the detection of the FLAG epitope in the experiment. The asterisk indicates predicted size of the DILP_FLAG peptide inserted in the pcg12_DILP vector.

Proteins extracted from three IndDILP lines shown to express the DILP protein were characterized further by comparing the proteins extracted from these strains when Cyc6 transcription was repressed versus induced. Of the four IndDILP strains tested, two seemed to correctly induce the production of DILP_FLAG, as a 12 kD protein. Therefore, the chloroplast inducible expression system developed here induced the expression of DILP. This finding was particularly interesting as previous attempts to expression the DILP protein in a constitutive fashion in the chloroplasts of *Chlamydomonas reinhardtii* never resulted in a high level of expression (Stefan Surzycki, personal communication). Thus, the inducible chloroplast gene expression system may provide a commercially relevant tool for the inducible expression of foreign proteins, especially those proteins resistant to constitutive expression.

EXAMPLE 6

Expression of Genes that Affect Hydrogen Production

Strains and Media

The nac2-26 mutant strain was previously described (Kuchka, et al. EMBO J. 7, 319-324; Nickelsen, et al. EMBO J. 13, 3182-3191). The cyc6Nac2.49 strain contains a trans-gene consisting of the Cyc6 promoter fused to the Nac2 midi-gene inserted into the nuclear genome of the nac2-26 mutant (nac2::cy6proNac2). Ind41 was derived from cy6Nac2.49 by replacing the psbD promoter and 5'UTR with a 675 fragment containing the petA promoter and 5'UTR (⬜ nac2::cy6pro Nac2::5'petA-psbD). Ind41-18 is related to the Ind41 strain, except that the aadA cassette in the Ind41-18 strain has been completely excised from the chloroplast DNA and the strain is therefore sensitive to spectinomycin (⬜ nac2::cy6proNac2::5'petA-psbD[Spcs]). Ind_aadA_117 was derived from Ind41-18 and contains the aadA cassette driven by the psbD promoter and 5'UTR inserted downstream of the atpB gene (⬜ nac2::cy6proNac2::5'petA-psbD::5'psbD-aadA). All strains were maintained on TAP (Tris-acetate-phosphate) medium supplemented with 1.5% Bacto-agar at 25° C. under dim light. In experiments where copper-supplemented or copper-deficient ($-Cu^{+2}$) solid agar and liquid TAP and HSM medium was employed, medium was prepared according to Quinn and Merchant (Methods in Enzymol. 297, 263-279). TAP and TAP-$Cu^{+2}$ media was supplemented with 100 ⬜ ⬜ g/ml spectinomycin (Sigma-Aldrich) or 20 ⬜ g/ml paromomycin (Sigma-Aldrich) where necessary. In experiments where cells were deprived of oxygen, liquid cultures where bubbled with $N_2$ gas with 150 rpm/min agitation and constant light illumination (20 ⬜ $E/m^{-1}s^{-2}$). Cell density was determined using a hemacytometer.

Plasmid Construction

Standard techniques were used to manipulate and analyze all plasmid constructs. Sequencing of constructs was carried out using BigDye terminator sequencing kit (Applied Biosystems, La Jolla, Calif.) and an ABI Prism 377 automated sequencing machine (ABI). The bacterial host used for cloning in *E. coli* was DH10B (Amersham Biosciences). All oligonucleotides were ordered from Microsynth GmbH (Balgach, CH).

Transformation of *Chiamydomonas* Cells

Nuclear transformation of *Chiamydomonas reinhardtii* strains nac2-26 was performed by electroporation essentially as described in Shimogawara, et al. Genetics 148, 1821-8.

Chlorophyll and Oxygen Evolution Rate Measurements

Oxygen evolution and respiration rates were determined using a Clark type oxygen electrode attached to a X type light source at 25° C. (Hansatech Instruments Ltd., Norfolk, UK).

Hydrogen Measurements and Calculations

All liquid phase and gas phase measurements of $N_2$, $O_2$, $H_2$ and $CO_2$ were performed as follows. Continuous monitoring of dissolved gases were made using a sealable, thermo-stated Clarks type vessel where gases were fed into the ion source of a mass spectrophotometer (model MM 880; VG Instruments, Cheshire, United Kingdom) through a polypropylene membrane under continuous agitation and constant illumination using a fiber-optic illuminator (model KL 1500, Schott, Mainz, Germany). In experiments where transcription of the Cy6Nac2 transgene was repressed, 12 ⬜ M copper was added to the growth medium within the vessel (TAP-$Cu^{+2}$ to TAP). Calibration of the mass spectrometer before all gas phase time-points was achieved through injection of air and pure hydrogen gas samples directly into the ion source.

Assay for aadA Activity

Assays for aadA activity were carried out on wt, Ind41-18, and Ind_aadA_117 strains essentially as described in Goldschmidt-Clermont, Nucleic Acids Res 19, 4083-9. except that $^{32}$P-labeled dATP was used in place of the radiolabeled rATP used in the original experiments.

Plasmid Constructions—pRS1_rcy_aadA Construction

The plasmid pKS-108#14 was used for the construction of plasmid pRS1_rcy_aadA. The pKS-108#14 plasmid contains the chloroplast DNA EcoRI R3 fragment of *C. reinhardtii*, with the aadA cassette inserted at position −263 bps relative to the psbD ATG initiation codon. In order to replace the psbD 5'UTR with the petA 5'UTR, a 943 bp chimeric DNA fragment comprised of the petA 5'UTR fused to the coding sequence of psbD was generated using overlap-extension PCR with oligonucleotides RS1, RS2, RS3 and RS4 (Tablet). The resulting PCR product was digested with Pvull/Clal restriction endonucleases and ligated into plasmid pKS-108#14 digested with the same enzymes to generate the pRS1 plasmid. The design of the chloroplast inducible expression system involves two successive chloroplast transformations which would require two different selectable markers. Alternatively, recycling of aadA is possible using a modified aadA cassette that is flanked by 483 bp direct repeats, allowing for the efficient removal of the cassette by homologous recombination after the selective pressure has been removed. Cloning of the recyclable aadA cassette into pRS1 was achieved by first cutting pRS1 with Clal and Sphl, and then filling the 5' and 3' ends of the resulting 6.3 kb plasmid with T4 DNA polymerase. This resulted in the excision of the atpA promoter and 5'UTR fused to the aadA coding sequence from the pRS1 plasmid, but did not remove the 3' sequence of rbcL. Insertion of the recyclable cassette into pRS1⬜ aadA was achieved by first excising the recyclable aadA cassette from pKS-483-aadA-483 plasmid using Sacl and Kpnl restriction endonucleases and blunting both ends with T4 DNA polymerase and PNK kinase. Blunt end ligation of the 2.8 kb recyclable aadA cassette into pRS1⬜ aadA was accomplished to generate pRS1_rcy_aadA (FIG. 27).

Construction of pcy6Nac2(paroR)

To construct a plasmid with the 428 bp Cyc6 promoter sequence fused in frame with the Nac2 coding sequence, a 5.1 kb chimeric midi-gene of Nac2 was employed. In brief, the plasmid pKS(-)nac2(midi) contains 3.0 kb of 5' Nac2 genomic sequence ending at the Sfrl restriction site within the Nac2 coding sequence fused to a 1.96 kb Sfr1/Xhol fragment containing the 3' cDNA sequence tagged with 3 HA, 6 His and 9 Myc epitopes, introduced in frame with the Nac2 coding sequence just upstream of the stop codon. In order to place the Nac2 gene under the control of the Cyc6 promoter, a chimeric DNA fragment comprising the Cyc6 promoter fused to the coding sequence of Nac2 was generated by overlap-extension PCR using 4 oligonucleotides specific for the Cyc6 promoter element and Nac2 genomic DNA. The resulting PCR fragment consisted of the 428 bp Cyc6 promoter fragment fused in frame with an 833 bp genomic Nac2 fragment. The PCR fragment was then cloned into the pNac2(midi) plasmid using the unique restriction sites Xbal and Aatll of pKS(-)Nac2(midi). Finally, the 5.8 kB Cyc6Nac2 trans-gene was cloned into the pSL17 plasmid using the unique sites EcoRI and Xbal of pSL17. This plasmid contains the aphVII cassette conferring resistance to paromomycin. The resulting 10.8 kb plasmid, pcy6Nac2 (paroR), was used to transform nac2-26 mutant cells.

Transformation of *Chlamydomonas* Cells

Cells of nac2-26 cells were grown in TAP medium, harvested in mid-log phase ($2-4 \times 10^6$ cells/ml), and treated with gamete autolysin, then re-suspended in TAP+40 mM sucrose medium. ⬜ For each electroporation, $10^8$ treated cells were incubated with 2.5 linearized pcyc6Nac2(paroR) or pSL17 plasmid DNA (to determine electroporation efficiency), plus 50 μg salmon sperm DNA, then transformed by electroporation in a 0.2 ml electroporation cuvette (Biorad, USA) using the Biorad (SIC) set to 0.75 kV, 25 μF and no resistance (Biorad, USA). The treated cells were recovered in 1 ml fresh TAP, 40 mM sucrose, 0.4% PEG-8000, 20% starch medium for 10 minutes, and plated on TAP medium supplemented with the antibiotic paromomycin (20 μg/ml). Paromomycin resistant colonies were screened for the ability to grow photo-autotrophically on minimal medium lacking copper (HSM-Cu$^{+2}$) at 25° C. in high light (45 μEm$^{-2}$s$^{-1}$). Photo-autotrophic strains were then tested for the abilitylinability to grow on minimal medium (HSM).

Chloroplast biolistic transformation of *Chlamydomonas* was performed with a helium-driven particle gun. $10^8$ cells of TAP-grown cy6Nac2.49 were plated on solid agar TAP supplemented with 100 μg/ml spectinomycin (TAP+Spc100) and bombarded with tungsten particles coated with 1 μg pRS1_rcy_aadA plasmid DNA. After 2 weeks in dim light (5 μEm$^{-2}$s$^{-1}$), single colonies were picked and re-cloned four times on TAP+Spec 100 medium, then cultured at 25° C. in dim light (5 μEm$^{-2}$s$^{-1}$) to ensure that the strains were homoplasmic for the selectable marker. To test for photo-autotrophic growth, cells were plated on solid HSM medium and grown at 25° C. under medium light (45 μEm$^{-2}$s$^{-1}$). In the case of transformation of Ind41_18, $10^8$ TAP-Cu$^{+2}$ cells were plated on solid TAP-Cu$^{+2}$ medium supplemented with 100 μg/ml spectinomycin (TAP-Cu$^{+2}$+Spc100) and bombarded with tungsten particles coated with 1 μg pcg12 plasmid DNA. After 2 weeks in dim light (5 μEm$^{-2}$s$^{-1}$), single colonies were picked and re-plated three times on TAP-Cu$^{+2}$+Spc 100 medium and cultured at 25° C. under dim light (5 μEm$^{-2}$s$^{-1}$).

Growth Analysis

For growth analysis of wt, nac2-26, cy6Nac2.49 strains, cells were grown in TAP-Cu$^{+2}$ medium to a density of $2-4 \times 10^6$ cells/ml, then diluted to a density of $1 \times 10^6$ cells/ml, followed by 10× serial dilution so that the final dilution was estimated to contain 100 cells when plated. Ten μl aliquots of each dilution were then spotted onto the appropriate solid agar plates, and grown under high light at 25° C. for 10 days. In the case of the Ind41 and Ind41-18 strains, $10^3$ cells were plated on the appropriate medium and cultured at 25° C. under continuous illumination (100 μEm$^{-2}$s$^{-1}$) for 10 days. For growth analysis of the inducible aadA transgenic lines, experiments were performed. In brief, wt, Ind41-18 and Ind_aadA transgenic lines were grown in either TAP-Cu$^{+2}$ or TAP liquid medium then transferred 3 times to either fresh TAP-Cu$^{+2}$ or TAP liquid media. Serial dilutions of TAP and TAP-Cu$^{+2}$ grown cultures were plated on TAP medium or TAP-Cu$^{+2}$ solid agar plates supplemented with increasing concentrations of spectinomycin (0-1000 μg/ml) and cultured at 25° C. in under continuous illumination (100 μEm$^{-1}$s$^{-2}$) for 10 days.

Fluorescence Transients Fluorescence transients were performed. Cells grown on TAP agar in
dark were analyzed with a Plant Efficiency Analyzer (PEA, Hansatech Instruments, UK) after dark adaptation for 5 minutes.

RNA Analysis

Isolation of total RNA from wt, nac2-26, cy6Nac2.49, Ind41_18 and Ind_aadA_117 strains was achieved using the RNA Plant Mini RNA extraction kit according to manufacturer's instructions (Qiagen Ghmb, Germany). In the case of RNA samples taken during time course experiments, $10^8$ cells were centrifuged at 3000 g and processed using RNAeasy RNA protection solution according to manufacturer's instructions (Ambion, USA).

RNA blot analysis was performed. RNA (2 μg) was electrophoresed in a 1.2% agarose-4% formaldehyde gel in 1× MOPS buffer, then transferred to a Hybond N+ nylon membrane (Amersham, USA) in 20×SSC buffer and UV-cross-linked to the membrane using a Stratalinker cross-linking oven. Pre-hybridization and hybridization of the membrane was carried out at 65° C. in modified Church's hybridization solution (0.5 M phosphate buffer (pH 7.2), 7% SDS (wlv), 10 mM EDTA). A 380 bp DNA fragment of psbD was isolated by digesting plasmid pks-108#14 with Accl and Styl for use as a probe and labeled with [α-$^{32}$P]dATP using the random priming technique. The 685 bps DNA fragment of Cyc6 cDNA was labeled with [α-$^{32}$P]dCTP using the random priming technique. A 804 Ncol/Sphl fragment of aadA coding sequence was isolated by digestion of the pcg12 plasmid for use as a probe and labeled with [α-$^{32}$P]dATP using the random priming technique. A 693 bps fragment of atpB was isolated by digesting pcg12 with EcoRV and Hpall for use as a probe and labeled with [α-$^{32}$P]dATP by random priming. After hybridization, membranes were washed at 65° C. for 10 min with high stringency washing buffer [0.1% SDS, 0.1% SSC].

Protein Analysis

Total protein extracts of *Chlamydomonas* strains wt, nac2-26, cy6Nac2.49, Ind41_18, and Ind_aadA_117 were prepared by collecting $3 \times 10^6$ cells in a 1.5 ml Eppendorf tube and resuspending the pellet in a 2× solution of Sigma protease inhibitor cocktail (Sigma-aldrech, USA) followed by lysis in an equal volume of cell lysis buffer (100 mM Tris-HCl pH 6.8, 4% SDS) at 37° C. for 30 minutes. To pellet cell debris, the samples were centrifuged at 10,0000 g for 5 min and the supernatant was used as total protein extract. To determine protein concentration 5 μl of supernatant was assayed using Bradford method (Bio-Rad Protein Assay, BioRad, USA).

For immunoblot analysis, 20 μg total protein was separated on a 12% SDS poly-acrylamide gel and transferred to Protran 0.45 μm nitrocellulose membrane (Schleicher and Schuell). When Nac2 antibody was employed, 8000 g protein was loaded on 8% poly-acrylamide gels. Membranes were blocked in Tris-buffered saline solution (containing 5% of non-fat dry milk and 0.1% Tween-20 (TBS-T). For the primary antibody reaction, dilution in TBS-T was as follows: D2 antibody, 1:10,000 dilution; D1, antibody 1:10,000; Nac2 antibody, 1:10,000; PsaA antibody, 1:10,000; AtpB antibody, 1:10,000; RUBISCO-Holo antibody, 1:50,000. Incubation was performed for 1 hr at room temperature. Subsequently, the membrane was washed five times for 5 minutes in TBS-T containing 1% non-fat dry milk. For the secondary antibody reaction, the membrane was incubated for 1 hr at room temperature with peroxidase-linked anti-rabbit IgG (in TBS containing 1% non-fat milk) at a final antibody dilution of 1:10,000. The membrane was washed 5 times for 5 minutes in TBS and the signal was visualized by enhanced chemiluminescence.

Copper-Mediated Repression and Time-Course Experiments

To folllow the copper-mediated repression over time of Cy6Nac2 in the cy6Nac2.49 transgenic strain cy6Nac2.49 cells were grown in TAP-Cu+2 medium to a density of $4 \times 10^6$ cells/ml, diluted in fresh TAP-Cu+2 media to a density of $5 \times 10^5$ cells/ml, then split into two independent production e.g. by using state transition mutants blocked in state 1 which are unable to perform cyclic electron flow or by driving one of the Calvin-Benson enzymes with the Cyc6 promoter. In this way carbon assimilation would be diminished at the same time as PSII activity and competition for electrons during the hydrogen production phase would be decreased.

TABLE 2

List of oligonucleotides.

| Name | Sequence 5'->3' | Restriction Site |
|---|---|---|
| RS1 | 5'GG*ATCGAT*GCAGGCAGTGGCGGTACC3' | EcoRI |
| RS2 | 5'GATATGTACCGATCGCAATTGTCATAATTTTATTAATCTTAAAAC3' | N/A |
| RS3 | 5'GTTTTAAGATTAATAAAATTATGACAATTGCGATCGTACATATC3' | N/A |
| RS4 | 5'GG*CAGCTG*TTAAGAAGTTACAACCTTC3' | PvuI |
| Cy6Pro-1 | | XbaI |
| Nac2-Cyc6-1 | 5'CGGTAGAGCCCC*CATATG*GATGGAGTAGGT3' | NdeI |
| Nac2-Cyc6-2 | 5'ACCTACTCCATC*CATATG*GGGGCTCTA3' | NdeI |
| Nac2(+1260) | 5'ACCACAGAGCCCTGCCAG 3' | N/A | cultures, one of which was left untreated while the other had copper added to the growth medium to a final concentration of 6 µM. Time points were then taken for each culture every 8 hours for 40 hours. Two independent samples were used for Fv/Fm measurements and the average for each culture was determined at the indicated time points.

Experiments to test the copper-mediated induction of cy6Nac2.49 were carried as described for the copper-mediated repression experiments except that pre-cultures of cy6Nac2.49 were grown in TAP medium and the cells were washed two times in copper-depleted medium before dilution in TAP-$Cu^{+2}$ medium at a concentration of $5 \times 10^5$ cells/ml. To initiate the time course experiment, cells were split into two separate cultures and copper was added to a final concentration of 6 µM in one of them.

Hydrogen Measurements

The hydrogen production in the cy6Nac2.49 strain was compared with that of the wild type under sulfur deprivation. In the cy6Nac2.49 culture used in FIG. 32, 20 µmol $H_2$/L was produced during one cycle corresponding to a maximal rate of 1 mmol $H_2$ $mol^{-1}$ Chl $s^{-1}$. These rates varied from one experiment to another and reached in some cases 3.1 mmol $H_2$ $mol^{-1}$ Chl $s^{-1}$. Under conditions permissive for photosynthesis (Cu-deprived medium) the net rate of oxygen evolution was 23 mmol $O_2$ $mol^{-1}$Chl $s^{-1}$ in Cy6Nac2.49 cells. This rate was 1.5-2 fold higher in wild-type cells. Thus, the maximal rate of hydrogen production ranged between 4 and 13% of the rate of net oxygen production. In the case of a culture subjected to sulfur starvation for 100 hrs, the average value can be estimated at 4 mmol $H_2$ $mol^{-1}$Chl $s^{-1}$. If one compares the 20 µmol $H_2$/L produced by cy6Nac2.49 cells during one cycle with the 4 mmol $H_2$/L produced during 100 hrs in a sulfur-starved wild-type culture, it is apparent that in order to achieve a similar hydrogen production, the cy6Nac2.49 system still needs further improvement, either a higher efficiency per cycle or a close enchainment of cycles. It is in principle possible to modify genetically Chlamydomonas so as to improve hydrogen No natural inducible chloroplast gene expression system is available for *Chlamydomonas*. Such a system was developed by taking advantage of the properties of the nucleus-encoded chloroplast Nac2 protein. This protein is required for processing and stable accumulation of the psbD mRNA which encodes the D2 reaction center polypeptide of PSII. The target site of Nac2 is comprised within the 74 nucleotide psbD 5'UTR. Fusion of this 5'UTR to another coding sequence renders expression of this gene dependent on Nac2. The Nac2 coding sequence has been fused to the Cyc6 promoter of the cytochrome $C_6$ gene whose expression is induced by copper depletion, anaerobiosis and also by addition of nickel, but which is repressed under copper replete conditions. Because of the specificity of Nac2 for the psbD 5'UTR, this system can be used in principle for the inducible expression of any chloroplast gene by fusing its coding sequence to the psbD 5'UTR.

Figure 26A:
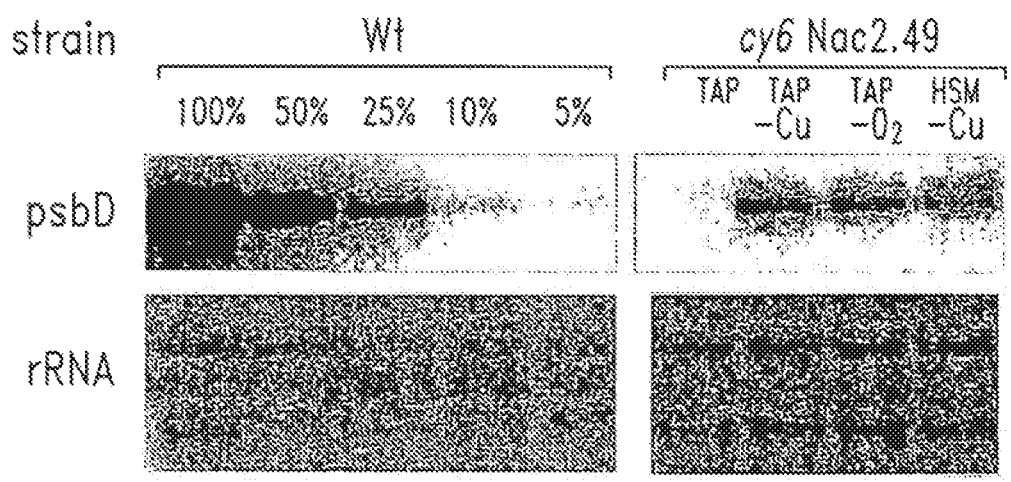
FIG. 26A-FIG. 26B shows accumulation of psbD RNA, D2 and Nac2 proteins in cy6Nac2.49.
Figure 26B:
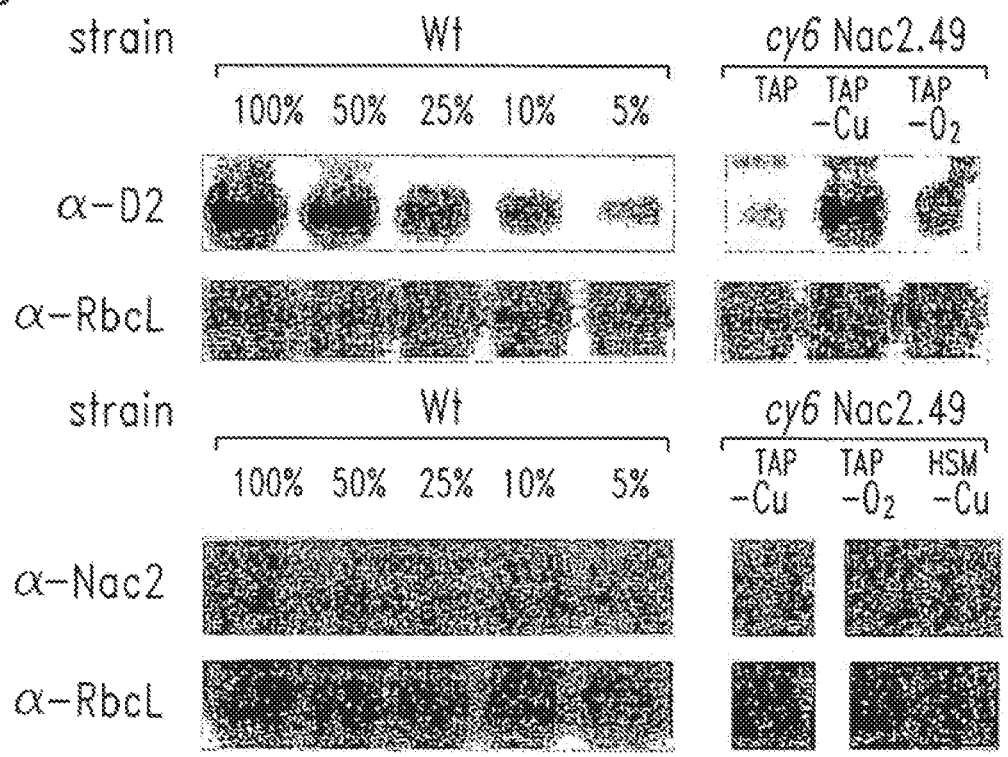
Figure 28A:
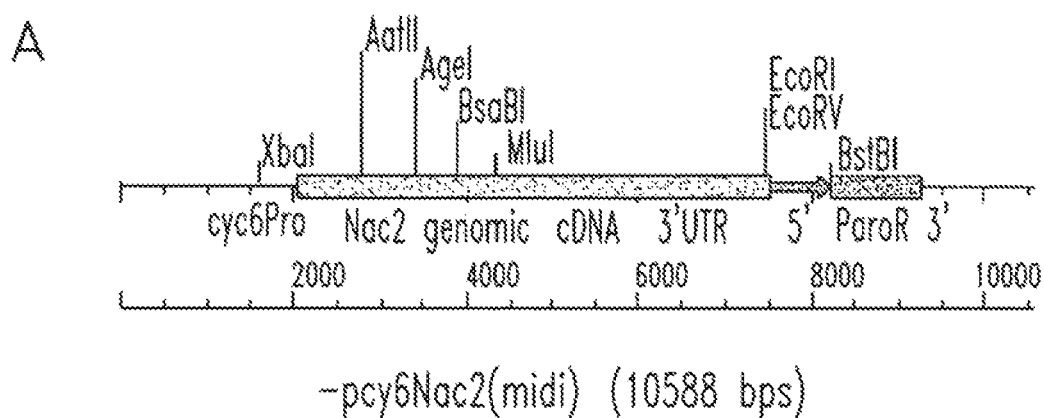
FIG. 28A-FIG. 28D shows inducible expression of the chloroplast psbD gene.
Figure 28B:
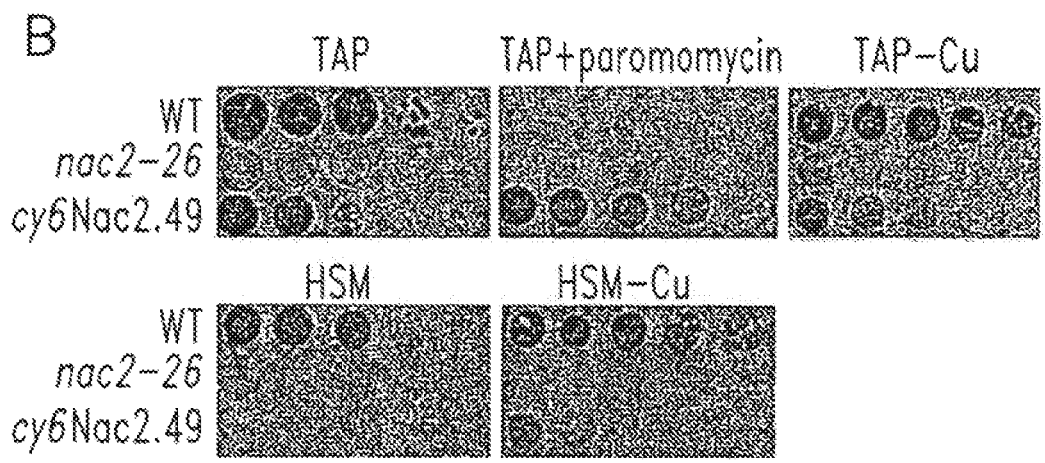
Figure 28C:
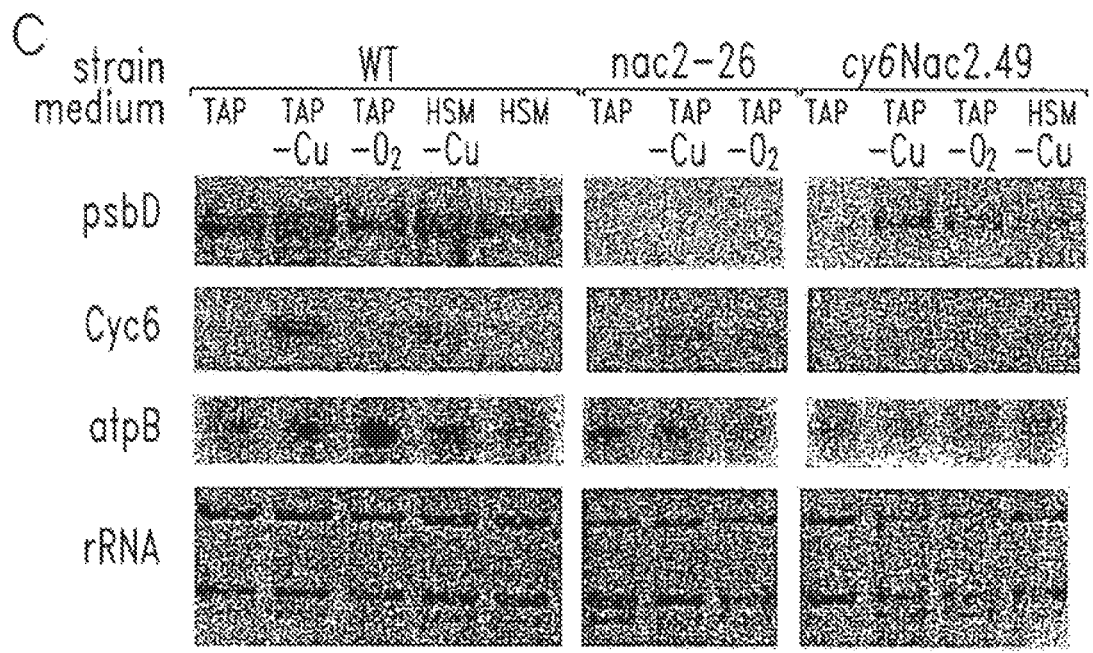
Figure 28D:
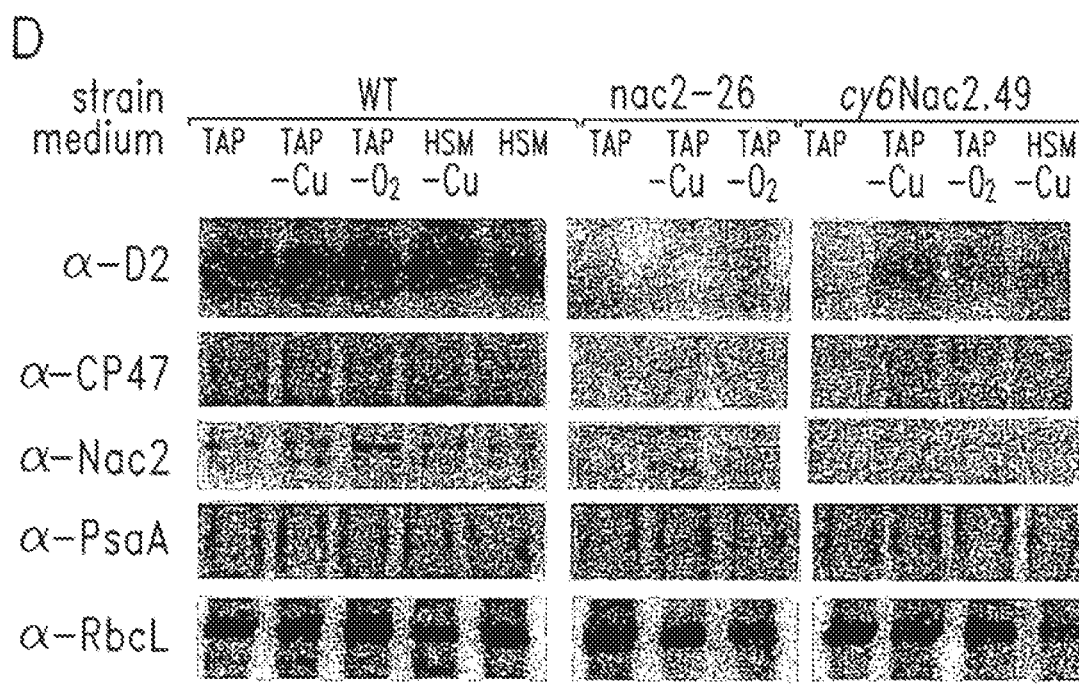

As described above, the Cyc6-Nac2 construct was inserted into a plasmid containing the aphVIII gene conferring resistance to paromomycin (FIG. 28A). This plasmid was used for transformation of the Chlamydomonas nac2-26 mutant using paromomycin resistance for selection. Amongst 55 transformants tested, two displayed proper control of Nac2 expression by copper. The growth properties of one of these transformants, cy6Nac2.49, of WT and of the nac2-26 mutant are discussed above (FIG. 28B). As expected, all three strains grow on TAP medium with and without copper and the transformants also grow in the presence of paromomycin because they contain the selectable marker aphVIII. Only WT cells grow on minimal medium containing copper. However, growth of the cy6Nac2.49 strain is restored on minimal medium lacking copper. Growth can also be restored by adding nickel because the Cyc6 promoter is induced by this metal. The level of psbD expression was determined by RNA blot hybridization under different growth conditions (FIG. 28C). As expected psbD RNA is undetectable in the nac2-26 mutant strain. In contrast in the cy6Nac2.49 strain, expression of psbD follows that of Cyc6 and is induced in the absence of copper or under anaerobic conditions (FIG. 28C). The level of the psbD product D2 was examined by immunoblotting using D2 antiserum (FIG. 28D). D2 protein is undetectable in nac2-26 cells grown on TAP plates under all conditions. However in cy6Nac2.49, it accumulates to 20% of wild-type levels when cells are grown in the absence of copper or under anaerobic conditions (FIG. 26). On minimal medium the induction of D2 is slightly lower. As expected other PSII proteins such as CP47 follow a similar pattern as D2 because it is known that these proteins are unstable in the absence of the D2 protein. In contrast the level of the Rubisco protein (RbcL) is not affected in nac2-26 (FIG. 28D).

Figure 29A:
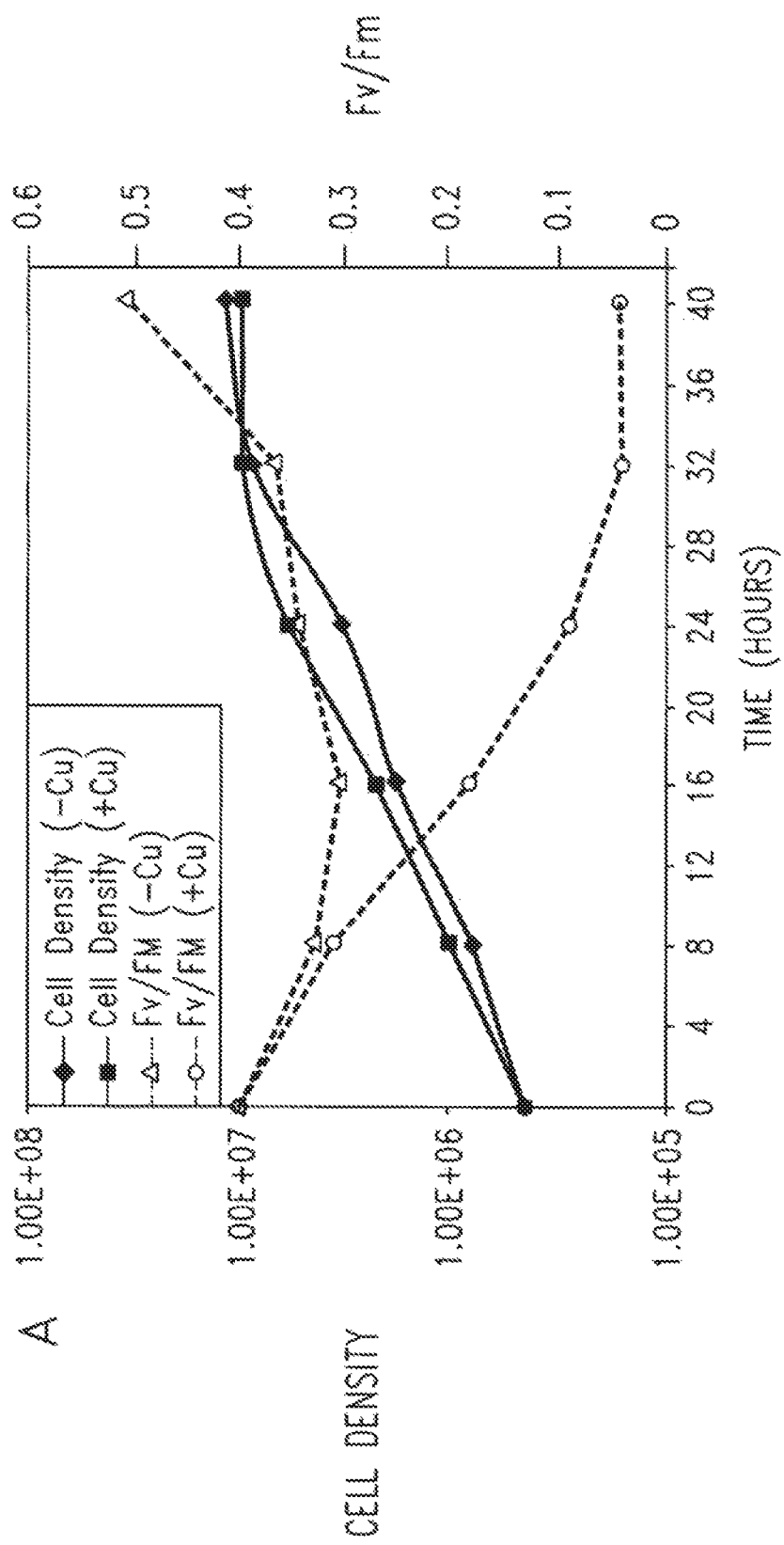
FIG. 29A-FIG. 29C shows a time course of copper-mediated repression of P511 synthesis in cy6Nac2.49.
Figure 29B:
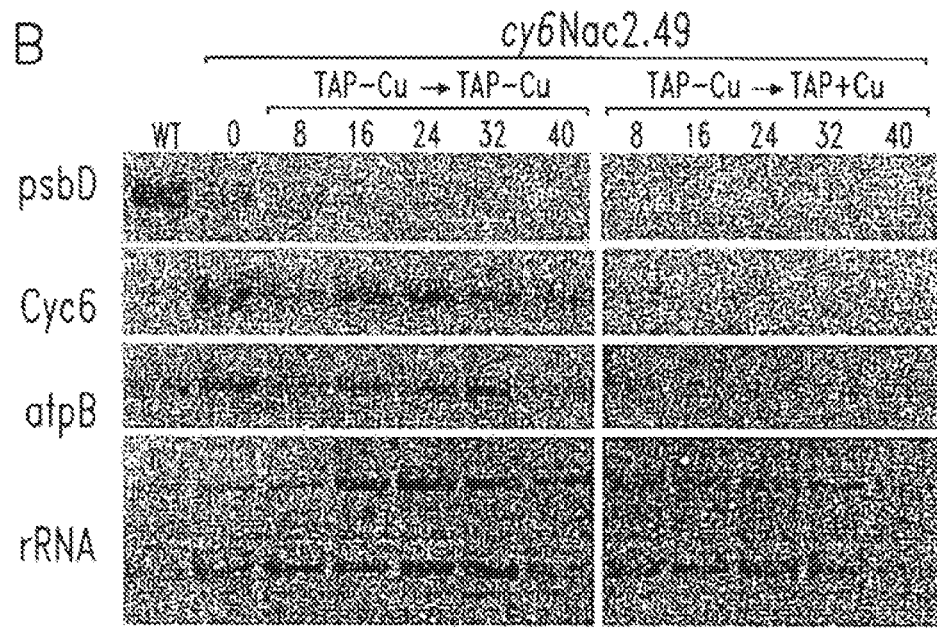
Figure 29C:
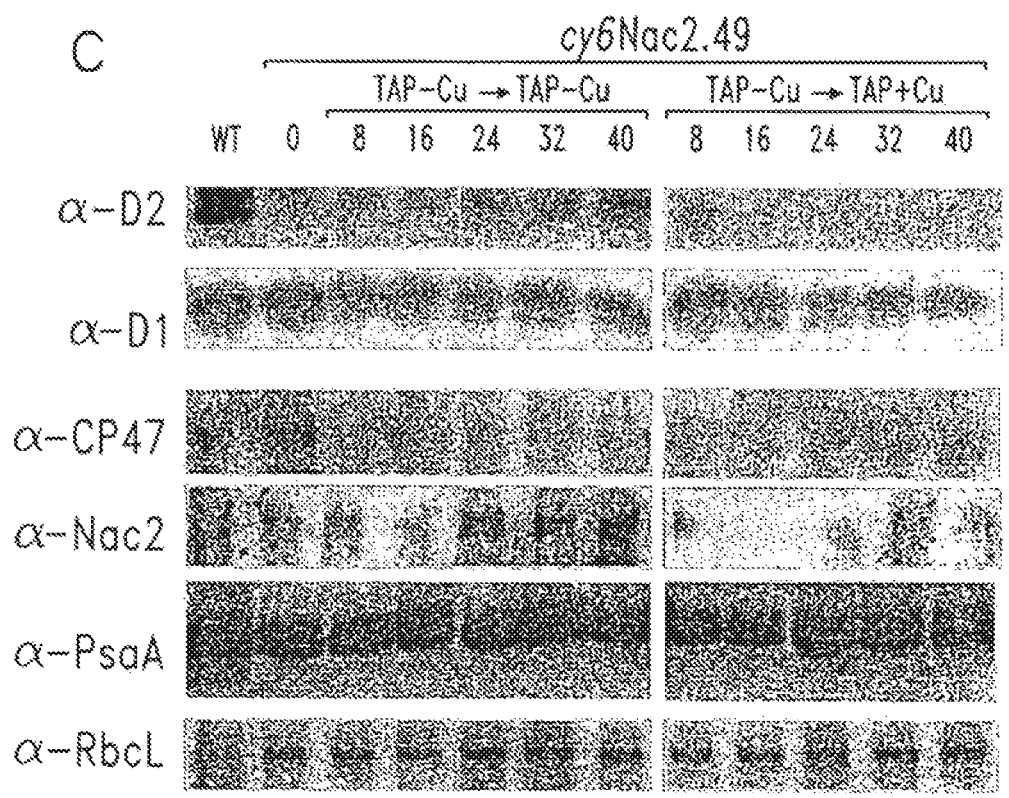

To assess the time required to deplete cells of PSII upon arrest of Nac2 synthesis, cells of cy6Nac2.49 were first grown in copper-depleted TAP medium. Under these conditions PSII is synthesized and accumulates. The culture was split in half and one culture was maintained under copper deprivation whereas copper was added to the other culture. The time course of cell density and the Fv/Fm ratio (variable/maximal fluorescence), which provides an estimate of PSII quantum yield, was determined at various time points (FIG. 29A). In the presence of copper the Fv/Fm ratio declined to a minimal value within 32 hours. During this period, cells divided 3-4 fold under both conditions and reached stationary phase. Cell extracts were prepared at various times for RNA and protein analysis. The levels of Cyc6 and psbD RNA were significantly decreased 8 hrs after copper addition and were undetectable thereafter (FIG. 29B). Other chloroplast RNAs (atpB, rRNA) were stable under these conditions. Immunoblotting revealed that the amount of D2 diminished after copper addition with a lag compared to the decrease of its mRNA (FIG. 29C) and the other PSII core protein D1 also decreased. As expected a decrease in Nac2 was also observed. In contrast chloroplast proteins from PSI (PsaA) and Rubisco were stable (FIG. 29C).

Figure 30A:
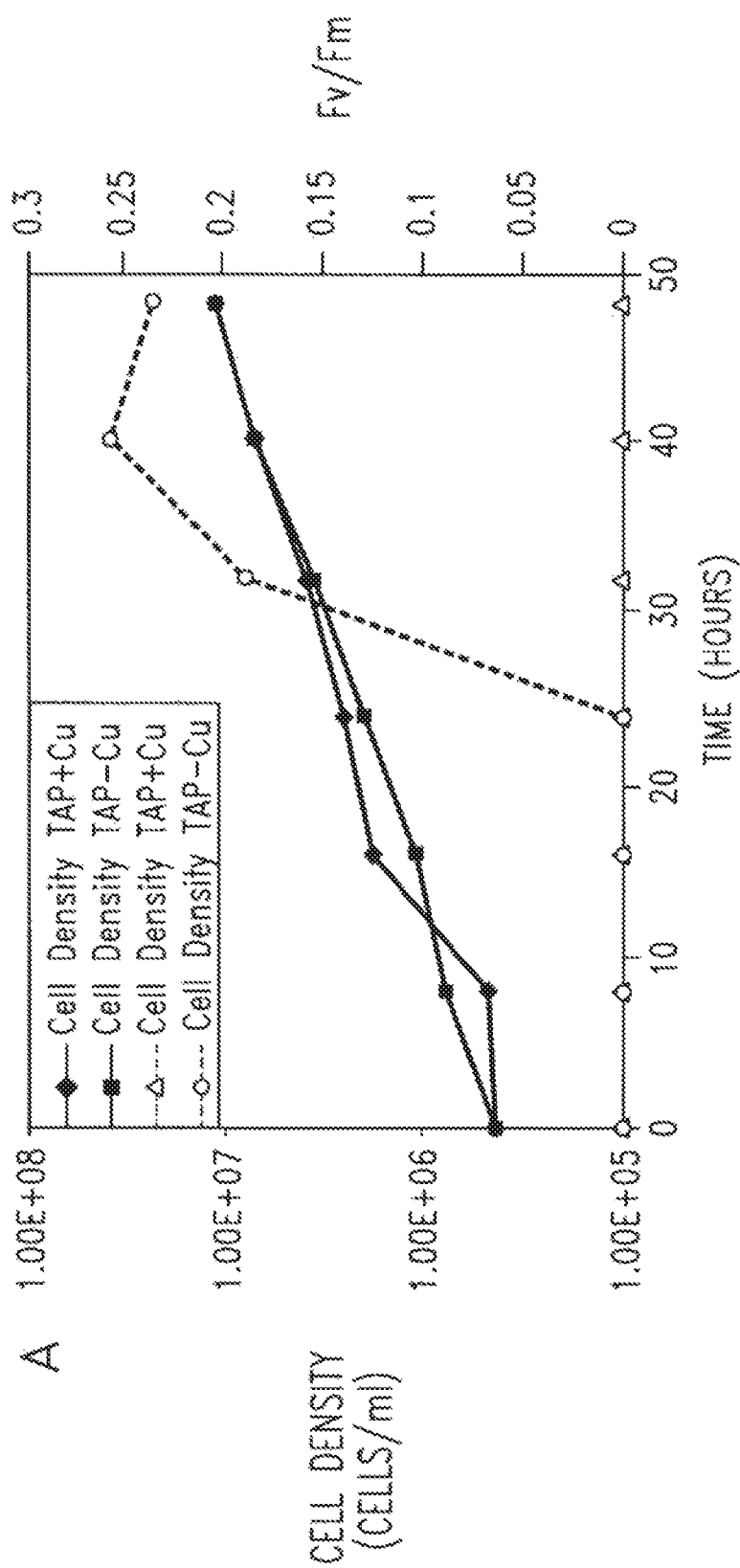
FIG. 30A-FIG. 30C shows a time course of accumulation of P511 in cy6Nac2.49.
Figure 30B:
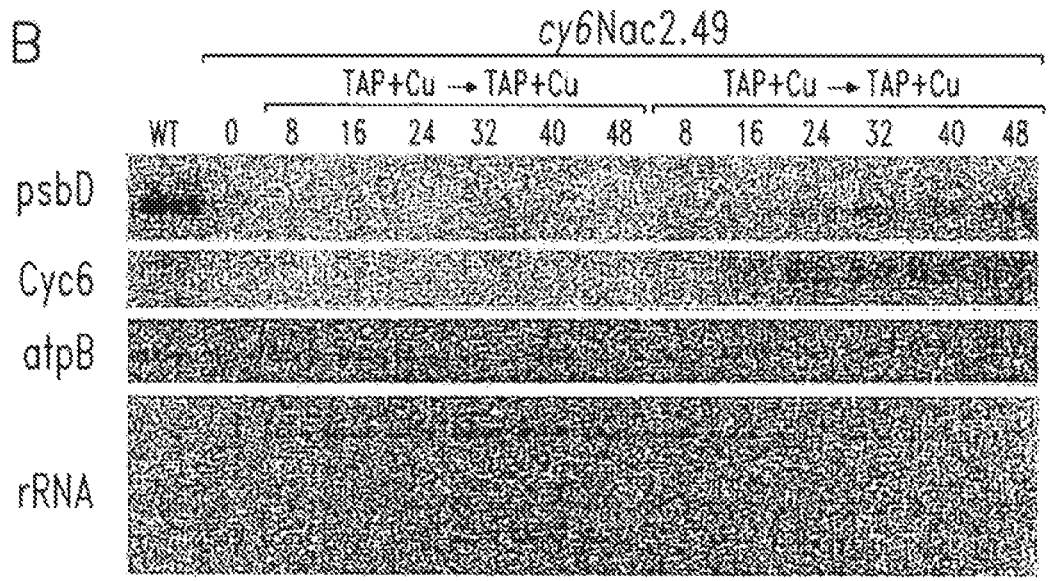
Figure 30C:
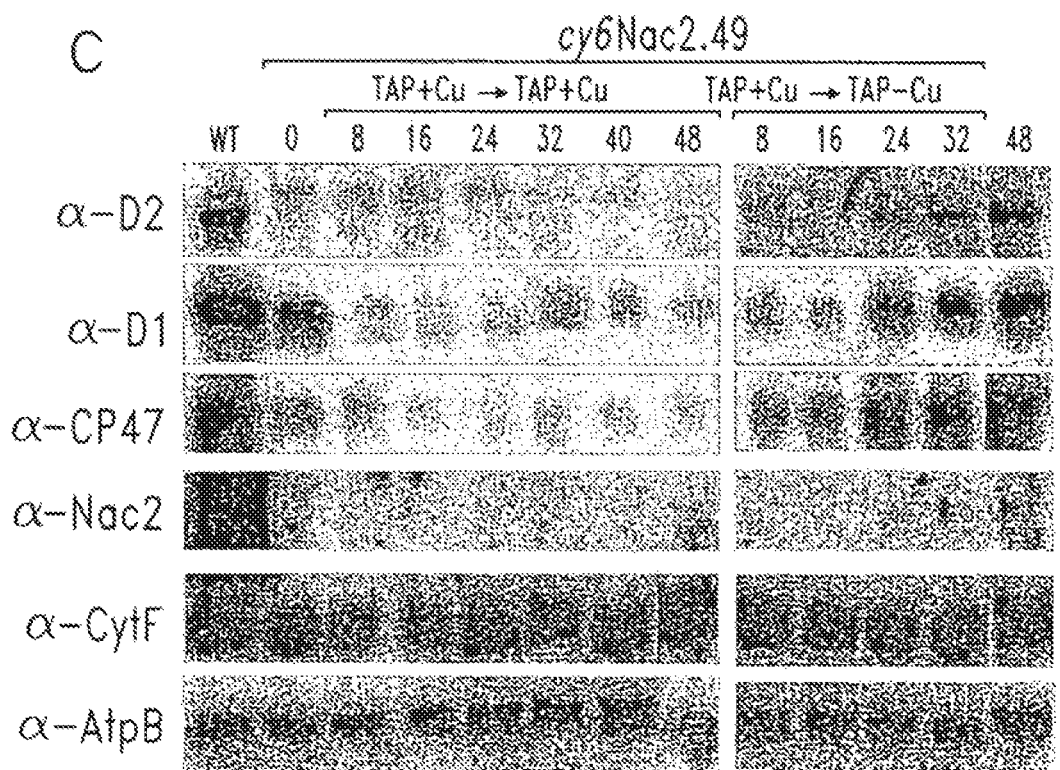

In a reciprocal experiment, cells grown in the presence of copper were transferred to TAP medium lacking copper and the time course of cell density and of Fv/Fm was determined. Fv/Fm started to increase only after a lag of 25 hours which is presumably due to the time needed to deplete the internal cellular copper reserve (FIG. 30A). RNA and protein from cell extracts at different time points were examined by RNA blot analysis and protein immunoblotting (FIG. 30B, C). While the Cyc6 RNA was detectable after 16 hours, there was a delay in psbD RNA accumulation and PSII activity presumably due to the fact that a threshold level of Nac2 is required for the accumulation of psbD mRNA and D2 synthesis.

Inducible Expression of Chloroplast Genes Unrelated to PSII

Figure 27A:
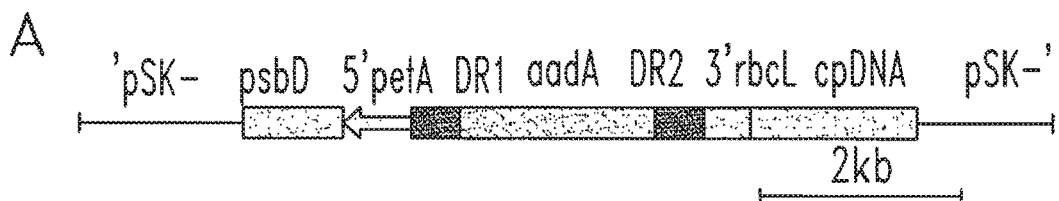
FIG. 27A-FIG. 27D shows restoration of constitutive PSII accumulation in cy6Nac2.49 by replacement of the psbD 5' UTR with the petA 5' UTR.
Figure 27B:
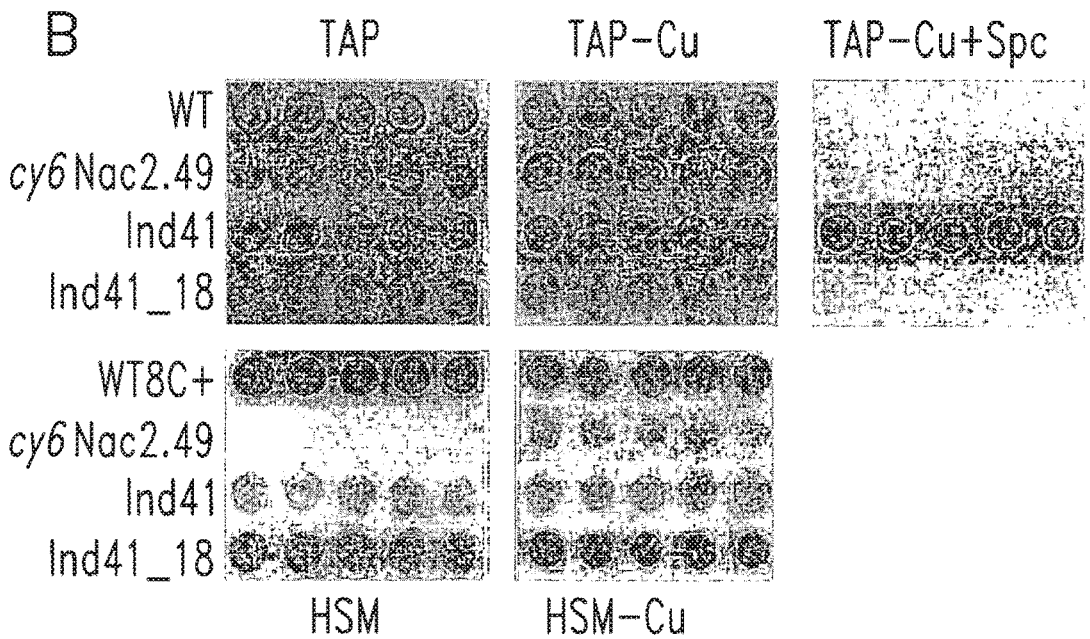
Figure 27C:
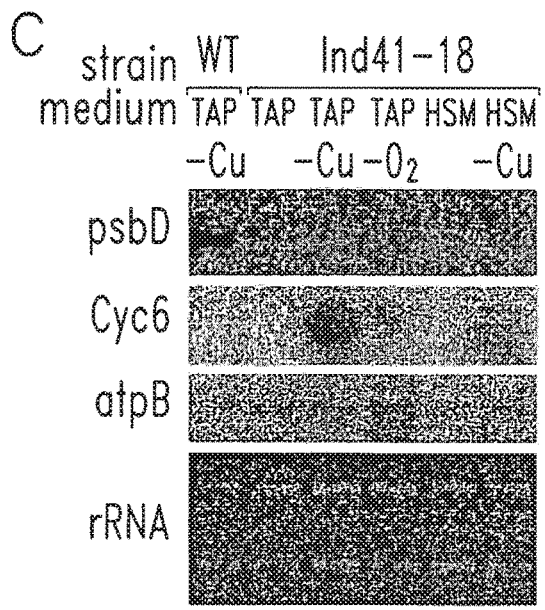
Figure 27D:
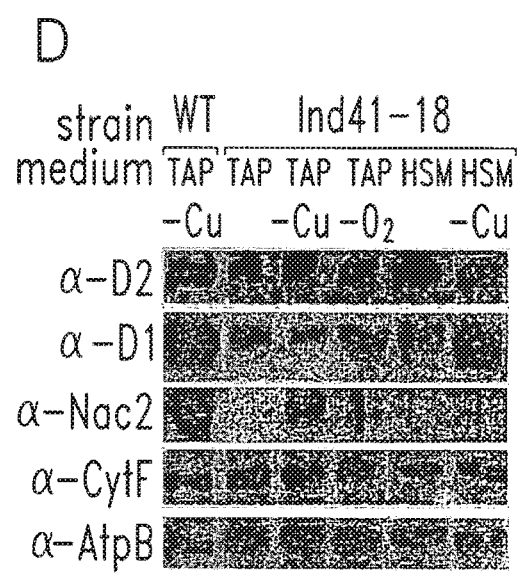

While the Nac2 system can be used to deplete PSII in a reversible manner, we tested whether it can be extended to any other chloroplast gene. This is in principle possible because the Nac2 protein acts specifically on the psbD 5'UTR and can drive chimeric psbD 5'UTR reporter genes. Hence it should suffice to fuse the psbD promoter and 5'UTR to the gene of interest. However, under those conditions PSII no longer accumulates because of the nac2-26 mutation which leads to the loss of psbD RNA. To circumvent this situation, the petA promoter and 5' UTR were fused to the psbD coding sequence and this construct was introduced into a modified version of the p108-14 chloroplast transformation vector. In this vector the recyclable aadA cassette is inserted upstream of the psbD gene which is driven by the petA promoter and 5'UTR (FIG. 27A). This DNA was inserted into the chloroplast genome by biolistic transformation using the aadA cassette as selectable marker. In this way the endogenous psbD gene was replaced by the petA-psbD construct and thus accumulation of its transcript was no longer dependent on Nac2. Transformants were restreaked three times on spectinomycin plates and the homoplasmicity was tested by DNA blot and PCR analysis and one of the transformants, Ind41 was selected. The aadA cassette used was flanked by two repeats. To allow for the excision of the cassette, the homoplasmic transformant Ind41 was plated repeatedly on medium lacking spectinomycin. In this way a strain was obtained, Ind41_18, which is sensitive to spectinomycin because it lacks the aadA cassette. The growth properties of Ind41, Ind41_18 and cy6Nac2.49 were tested on different media (FIG. 27B). As expected ind41 grows in the presence of spectinomycin in contrast to Ind41_18 which is sensitive to the antibiotic. Moreover both Ind41 and Ind41_18 grow on HSM minimal medium with or without copper. RNA blot analysis revealed that the chimeric petA-psbD RNA in Ind41_18 accumulates under all conditions independent of the Cyc6 RNA level (FIG. 27C). The psbD RNA is larger because the size of the petA 5'UTR exceeds that of the psbD 5'UTR. Immunoblot analysis revealed that D2 and D1 proteins accumulate to the same level under all conditions tested, in particular when Nac2 is not expressed (FIG. 27D).

Figure 31A:
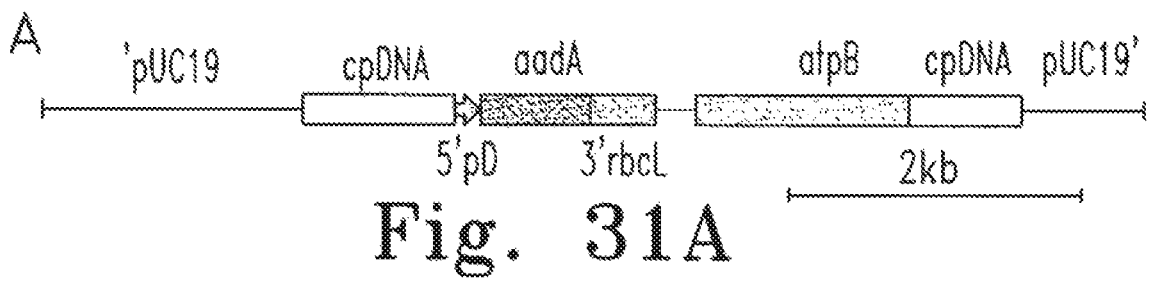
FIG. 31A-FIG. 31D shows expression of the psbD-aadA gene is induced by copper depletion and repressed by copper in the IND_aadA_117 transformnants.
Figure 31B:
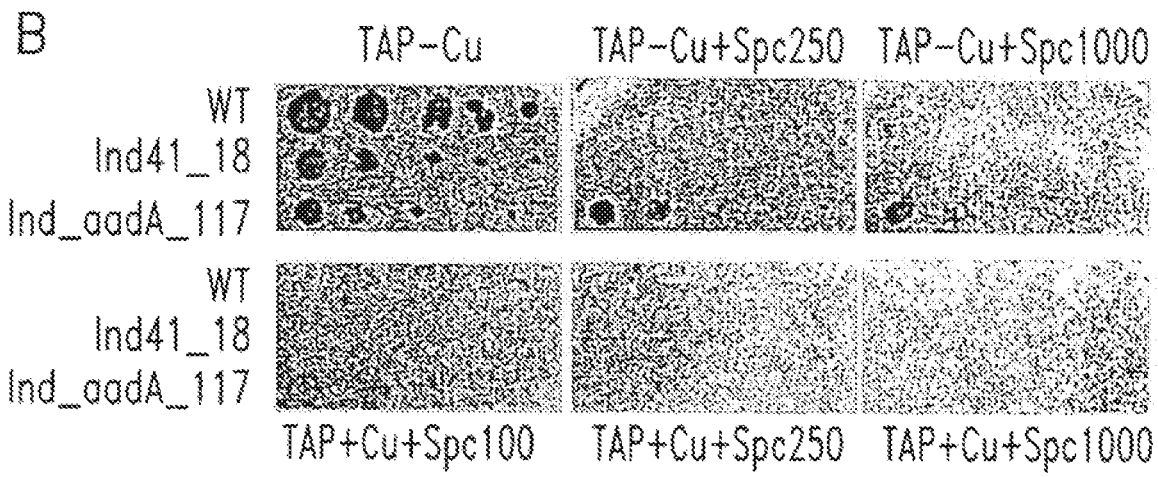
Figure 31C:
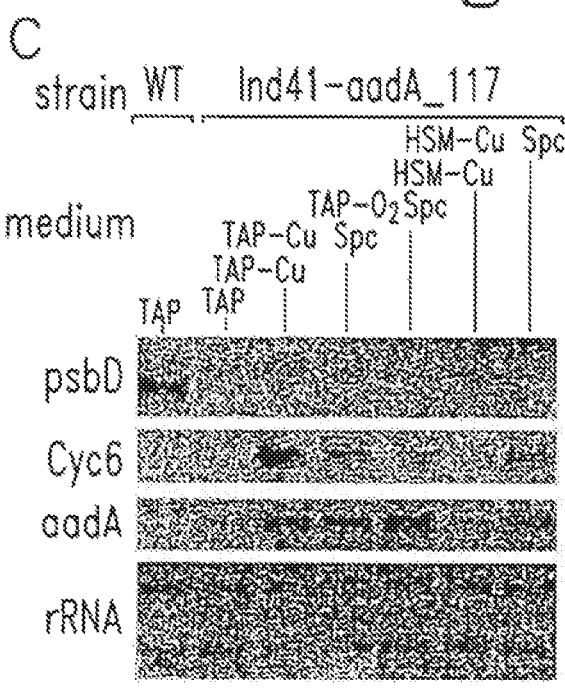
Figure 31D:
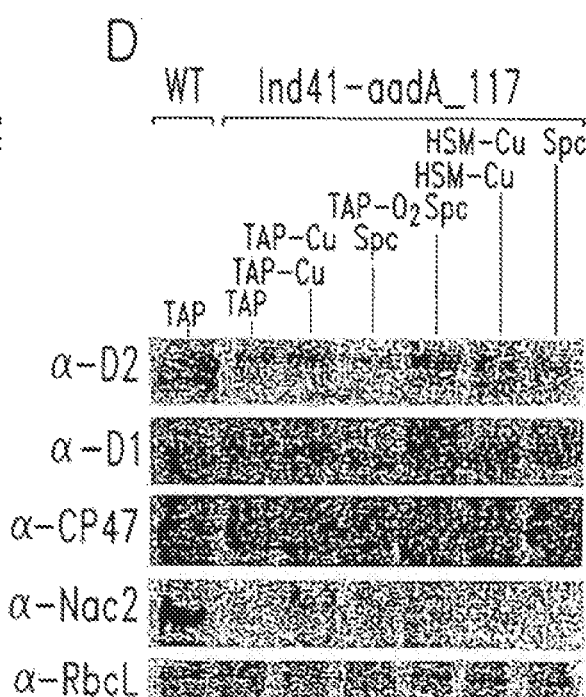

Next, the aadA cassette fused to the psbD promoter and 5'UTR was introduced into this strain by transformation using the cg12 vector (FIG. 31A). Growth of the transformants Ind_aadA-117 and of Ind41_18 was tested on TAP plates containing increasing amounts of spectinomycin with and without copper (FIG. 31B). All strains grow in the absence (FIG. 31B) or presence of copper. As expected the Ind_aadA-117 grows on spectinomycin plates at concentrations of 250 $\mu$g/ml or higher only in the absence of copper. A faint growth was also observed in the presence of copper on plates containing 100 $\mu$g/ml spectinomycin. RNA blot analysis revealed that aadA RNA accumulates only under inducing conditions for the Cyc6 promoter (FIG. 31C). Protein levels of D2, D1, CP47, and RbcL were largely unaffected but Nac2 was only detected under inducing conditions (FIG. 31D). Because of a lack of reliable aadA antibody, the amount of this protein was assayed by measurements of aminoglycoside adenyl transferase activity. The activity was significantly elevated under conditions when Nac 2 is expressed (Table 3).

TABLE 3

Aminoglycoside adenyl transferase activity in Ind41_aadA-117 under inducing and repressing conditions.

| Strain | +Cu | −Cu |
| --- | --- | --- |
| WT-aadA | 207.0 +/− 49.5 (3) | 192.6 +/− 51.4 (4) |
| Ind41_18 | 9.2 +/− 4.1 (4) | 12.2 +/− 7.9 (4) |
| Ind41_117 | 24.2 +/− 12.5 (4) | 274.3 +/− 90.6 (7) |

Extracts from WT-aadA, Ind41_18 and Ind41_aadA-117 strains were assayed for aadA activity and for total protein content as described above. The activity is indicated as cpm incorporated per $\mu$g protein. Numbers of independent measurements are indicated in parenthesis.

The inducible chloroplast gene expression system can be used to trigger hydrogen production

Figure 32A:
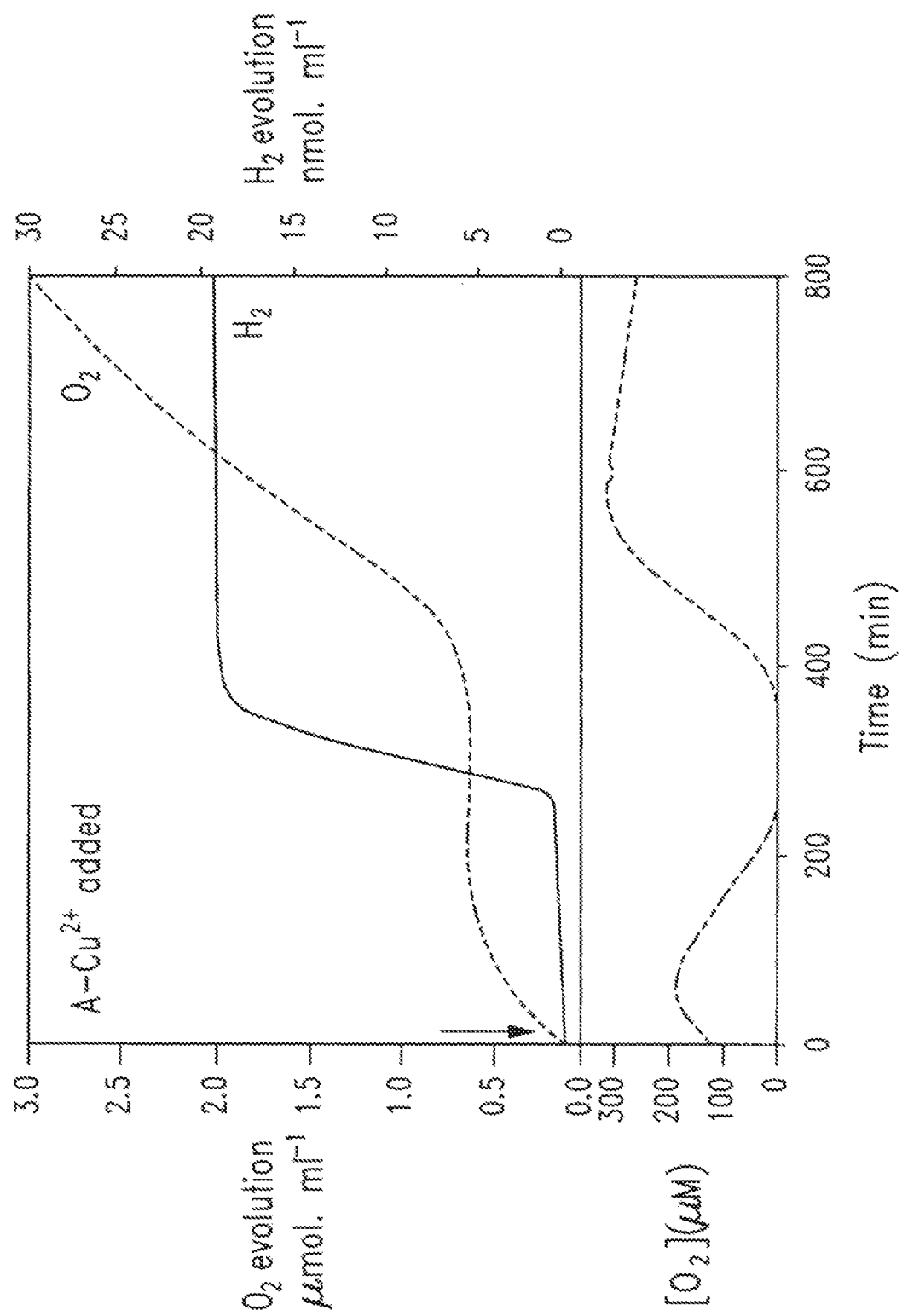
FIG. 32A-FIG. 32B shows hydrogen production in the cy6Nac2-49 strain.
Figure 32B:
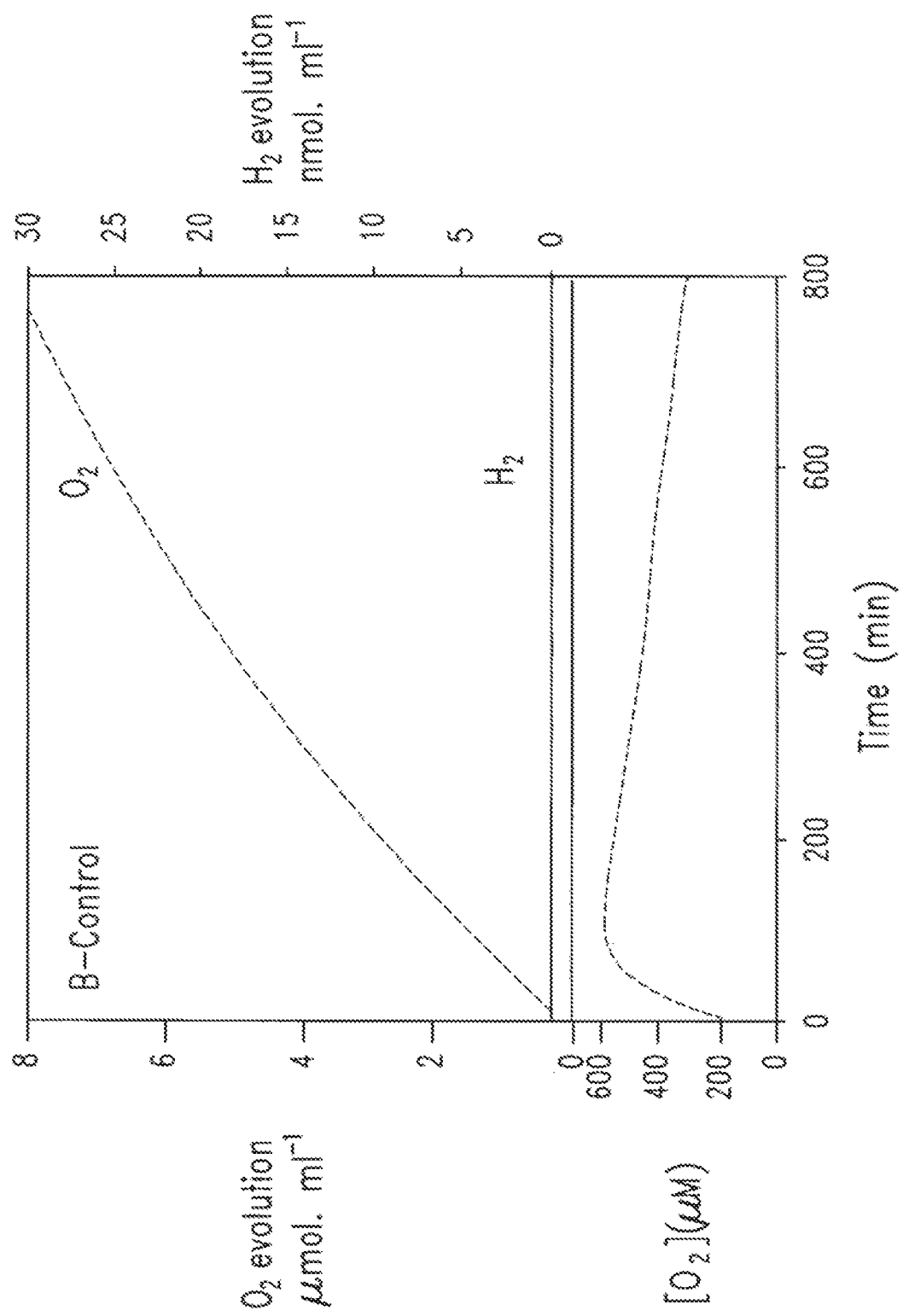

*Chlamydomonas* is able to induce hydrogenase and produce hydrogen under anaerobic conditions in the light. It was therefore tested whether the inducible Nac2 system could be used to turn off PSII activity and $O_2$ evolution, so that respiration would lead to anaerobic conditions suitable for induction of hydrogen production. Cells of cy6Nac2.49 were grown in TAP medium lacking copper to a concentration of $2 \times 10^6$ cells/ml. Copper was added and the cells were transferred into a chamber connected to a mass spectrometer and illuminated with white light (250 $\mu E\ m^{-2}s^{-1}$). In this system the bottom of the chamber is sealed with a polypropylene membrane which allows dissolved gases to diffuse directly into the ion source of the mass spectrometer. In this way the abundance of $O_2$ and $H_2$ could be measured at discrete time intervals. Because the chamber was closed and because copper repressed the synthesis of PSII, $O_2$ evolution diminished. Within a period of 200 min the $O_2$ was consumed by respiration. An anaerobic state was reached which led to the synthesis of active hydrogenase and $H_2$ production (FIG. 32A). The maximal rate of hydrogen production ranged between 1 and 3.1 mmol $H_2$ $mol^{-1}$ Chl $sec^{-1}$, slightly lower than that obtained with sulfur-starved cells, and of much shorter duration (around 1.5 h vs 3-4 days).

An interesting feature of the Cyc6 promoter is that it is also induced under anaerobic conditions even in the presence of copper. It would therefore be expected that once anaerobic conditions have been reached and hydrogenase is induced in cy6Nac2.49 cells, Nac2 synthesis resumes, PSII is synthesized and oxygen levels rise thus inactivating hydrogenase and blocking hydrogen production. This was observed. PSII synthesis was switched on during the anaerobic hydrogen production phase with concomitant $O_2$ evolution and inactivation of hydrogenase so that the hydrogen levels remained constant (FIG. 32A). As a control, the same cell culture was examined without addition of copper. Under these conditions no hydrogen was produced (FIG. 32B) with a constant production of $O_2$ and a gradual decrease of $CO_2$ as observed in the copper-treated cells. Because the Cyc6 promoter is expected to be switched off under aerobic conditions in copper-replete medium, a new cycle of hydrogen production would be expected. To test this possibility further cy6Nac2.49 cells were grown in TAP medium lacking copper in a sealed vessel for 50 hrs and measurement of hydrogen and oxygen were performed by mass spectrometry. The results suggest that two successive phases of hydrogen and oxygen production occurred.

Although the invention has been described in detail with reference to certain preferred embodiments, variations and modifications exist within the scope and spirit of the invention as described and defined in the following claims.

---

What is claimed is:

1. A method for preparing an expression system for inducing the production of a protein in the plastid of a cell, the method comprising the steps of providing a *Chlamydomonas* cell that comprises in its plastid a construct comprising a promoter and a psbD 5'UTR operably linked to a nucleic acid encoding a heterologous protein, wherein the heterologous protein is *Drosophila* insulin-like peptide (DILP);

introducing a recombinant nucleic acid into the nucleus of the cell, wherein the recombinant nucleic acid comprises an inducible promoter operatively linked to a nucleic acid encoding a stability factor, wherein the stability factor is Nac2; and contacting the cell with an inducer or treating the cell under conditions that result in the removal of a repressors;

wherein the inducer or repressor associates with the inducible promoter in the nucleus; and wherein the association of Nac2 with the mRNA encoding DILP enhances expression of the mRNA, resulting in the production of DILP in the plastid.

* * * * *

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggatcgatgc aggcagtggc ggtacc                                          26

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatatgtacc gatcgcaatt gtcataattt tattaatctt aaaac                     45

<210> SEQ ID NO 4
<211> LENGTH: 44
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 4
gttttaagat taataaaatt atgacaattg cgatcgtaca tatc                        44

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggcagctgtt aagaagttac aaccttc                                           27

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cggtagagcc cccatatgga tggagtaggt                                        30

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acctactcca tccatatggg ggctcta                                           27

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
accacagagc cctgccag                                                     18

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 9
ccannnnnnt gg                                                           12

<210> SEQ ID NO 10
<211> LENGTH: 5893
```

<212> TYPE: DNA
<213> ORGANISM: Chlamydomonas sp.

<400> SEQUENCE: 10

| | | | | | |
|---|---|---|---|---|---|
| gaattctgct | gcggaaaggt | taactggccc | aaagacttgc | ggcgcagcgc | tgaaatagct | 60 |
| cccaaaacct | agatacgctc | cgtcatgaaa | caaaacatgt | atatattagc | aaaagggcgt | 120 |
| gactgccggg | gcgagcggcc | tcgcccagcc | gatctctcca | tcgtgcttgc | tgtcaccgct | 180 |
| cgctgctcaa | cacaggctaa | cttagcttgc | ctttggtaga | cattgtgcaa | tcagtcacac | 240 |
| ctcaagcgct | aatcttcaaa | atctttcggt | cgactgaaac | gatagtgagc | gtctcagaac | 300 |
| gagtcttgtg | taggccgcac | gtttgaagcg | gtcggggccg | tgtccaacgt | ataggttgct | 360 |
| gttatcaaga | agaaacaaac | cagctggtag | caaacctcga | acgaagtatg | gcacggccat | 420 |
| agaagcccgg | ccttgcggga | gaactccgga | aaatggggc  | tctaccgtgc | ccagctcata | 480 |
| tcgagcatca | tcagggctta | tcatcgtttg | ggacacggcg | agtcctgcgg | caaagcgtgg | 540 |
| cttgtggagc | tcaccgcagt | cggcgaaggt | ccctgtgggc | aggcgcttct | cccgcgcac  | 600 |
| ctaaatatga | cgagggcgca | ttatcgtgta | gctttcaact | gggctcggcg | agcctgcacg | 660 |
| tcagcgaggt | aggcttgttt | tcttgccaca | gtgtatgggt | ggctcgggag | acctgggaga | 720 |
| tcggagcgtt | gggtgttcgg | ggctcgcgaa | tggtgcagaa | acaagcttcg | tggcatttaa | 780 |
| ggcgtcccgc | gacaataaac | gcaggttcga | ggttcgcgac | acgcgacacc | aagggcccct | 840 |
| ccaaccggcg | gatgtatcga | gctcccgaaa | actctcgcgc | tcacggagga | gcaggaccag | 900 |
| cgggctgcgc | gggcgaccag | ccagctgcta | aatgccatca | gtcgctgtgc | cgcgggctcg | 960 |
| cctttggcgc | gcttactgac | tggtcctcat | ggagccgcga | gcgcaactgg | tgccgggagc | 1020 |
| cactcgtcgt | cggccgggc  | gcccacgccg | acgccgcggc | cggacatcgc | ggccgctgca | 1080 |
| gcgctgctcc | cctcgctgac | ttggcgctgg | gtgtcggtgg | cggacctgga | aggaggctgg | 1140 |
| gttgaccgcg | gcgtagcgca | cctgctgcgg | gaagccttgc | tcgtgcagaa | agccgcgtcc | 1200 |
| gacgtcaacg | catccgtcag | gtgggcagca | ccgcgttctt | aaggcgtgac | ctgccgtaca | 1260 |
| ttgctgcag  | ggctctgtgg | tatggagcca | tggatgtccg | ttgcagtttg | ttgactcagc | 1320 |
| acgcgctggc | aggctgacac | gctgcggcat | gtgtgcacgt | ccggaaacgt | tccttgcgcg | 1380 |
| agctgggctc | aacctgacat | aatctgctgc | ccgcctgccg | ctgctaccct | gcgtattcct | 1440 |
| ctgccgtagt | gagctggtcg | ggtggtgcat | ggacaactgc | agcgcacccg | cggcggcact | 1500 |
| ggcggcgctc | tgggggcagc | agcagggagc | tgcgctgccc | gcccgcagcc | gcagcttcta | 1560 |
| cggcctgctg | cttcagcgcc | tggacggcgg | tggcgccagc | tcagcagttg | ctgctgcggc | 1620 |
| aggccgccag | ccgcacgagc | accaacagga | gcgatcatca | gctgaggcgt | acggtctgtc | 1680 |
| cccggcactg | gtgttttgca | gctcagtcgc | ccgcaccgca | ctctccacct | cctcacgccg | 1740 |
| cggtgggcgc | tcctcctctt | cagaggaaga | cggcgatgcg | cacgacgacc | ggtcgcaccc | 1800 |
| acatacgcag | cagctgctgg | agcaggacgg | gtcgagccg  | ctggttggtg | ctgctgcgtc | 1860 |
| cccctccagc | aatggcaagc | gctcggcggc | tggccctagc | gccggtgccg | acgttatcct | 1920 |
| tgttggtgag | ctgcccggtg | acgtgctatt | ggacgagtcg | gtgggcaacg | tccgccgcca | 1980 |
| gcagccgcac | gcgaacggct | ccggcgctaa | gcacaacggc | gtgaatggca | gcggtaaaag | 2040 |
| cggatccggt | ggggccaagg | tggcgcatgc | gcatgtcaac | ggctctgcag | cagacacgga | 2100 |
| cccagggcaa | gcagccctgg | gcgtgaaggg | gagcgcagag | tctcctctgg | agcagccggc | 2160 |
| gccggcggca | aagcggtcag | ctgcaggaaa | ggcctcccgg | cctgccgcgc | ttctcctgaa | 2220 |

```
gcgcccgtcc cgcagcgccg ccccgccagc accaacgctg cccgacggtg cggaggcgga    2280
cggattcgca tcggacggga gcggcctgcc aggacacggg cagcagcagc tctccgccat    2340
tgcggcggcg gcagcagcct catcgctcct ggccggcccg gcggcgccca tgtcgttcct    2400
ggagacgctg agcgacgacg acgacgaggc gcggcgcgcg cgtcgctcc tgaacggcgc     2460 cggcatgtcc gaccccgcct ccgctagcag caccagcacc agtagcaaca gcggcaccag    2520
caacctggtg gggcgtgtgt tcgtgcccat gcggctggta tcggtcagcc gcttccgcct    2580
ccgcgacgct ctgggccggc cgctgcccga cggcctggcc gtgccgccta ctgggcccat    2640
cgtgctcagc aacgacgccc gcgtgttccc cggcactgag ggcctgctgt ccgactacgc    2700
cacgcccgcc ggcgacaaac tcgccgtacg gctggaatac atcacggacc gctcgtacgc    2760
gtacggcgac gtgcgcgctgc agctgttcaa catcagccgc gtgacgcgca agcgtacgga    2820
caactgccag atgctggtca acggcaagcc ggtcaacgtc ggcgacccgg tgtgccgct     2880 ggtgcctggt gacgagattc ggtttggtgc cagcgcggcg tttgcgttcc ggctagaggc    2940
actgccggag gcgccgtctg ggctggaggc ggcggtgcaa cagctacagc ttcacgccga    3000
cagcagcagc agcaatggca acggcagtgg cagtagcagt agcagcgggc tgccgcaggt    3060
cagcgaggag gaggtggcgg cggcggcggc tgacatggcg tccctgtcta acatgtcccg    3120
ccgtgacccg ccccgtgctg aggcgctgct gcgacggctg ctggcggcgc gcccgggcga    3180
cgccgcgctc tggctcatct gggcgcagat ggcagcgcgc gtgaaggcc ccgggccggg     3240 gcaggccaag gcgcggatgc tgttccgcgc agcagccgat gccgcccggc gcatgcctgt    3300
gctgccgccg ccgccgctgg cgctgcagat ggcggcgcgg cgcgccaccg cgccggccg    3360 gcgccgtcgg cgcggcgcct ccaccaccgc atccatggac ggcgacgacg gcgcgctcag    3420
cgttgccgac ggcagcagca cgccgatgc cgcgattgac ccggcatccg gtgcttcgcc    3480
gtcagctgcc gccggcccgc cggcgccctc cgcccgaccg cggcacaact ggttgcttgt    3540
gcaggcgctg gggaactggg gcaagcacga gtggcggctg cgcatgtatg gctccgcgcg    3600
gcacctgttc cgcgccgccg cggacgaggc ggcgcggcac tcgggcggcc tggcggcggg    3660
cggcggcggc gcggtgatgc actactgggg cagcccgggag ctggaggcgg caatgtgcg    3720 caacgcgcgc atcgtggcgg cggaggcgct gcgcaagtgc ccggccgacg tggcgctgta    3780
cgtgctggca gcaagcgtgg agctggaggc cagcaacctt gagctggcca agggctactg    3840
ccagcgcgcc tacgctctgg accgcacaga caagcagctg ttttttgatct ggccgcgtgt    3900 ggaggcggga ctgggcgacc gcgacaaggc gcgattgctg ttcgagcgcg cactggacgc    3960
gcacccgctt aacaccaaga tcatcaacat gtacgctcgc tttgaggcag aggagggatc    4020
ctaccgcgaa gcggcagagc tgtacgacag gcgctgcaa atcgacccac tgtcgcccgg    4080
ccccggcgtg cacaaccgcg cggactgggc ttccatggag accgacctgg ggaacacagg    4140
cctggcgcgg cagctgctgg aggagggct ggaggcgcac cccaacagcg ccgcactgct     4200
ggtcgtgtac agcaagctgc agaggctgga gggcaggtac caggaggctc tggcggctgt    4260
gcggcgggcg caggcggtgg cgggcgcgtt caatgctgcg gtcatgaatg agcgggcaca    4320
ggtgctgcgt gcgctgggcg agcgcgaact ggccgccaac ctgtcgcgcc acgtgtcagc    4380
cgtgaaacag ctcaaccgaa tgaagcagca gggctactgg ggctcagagg cctggagggc    4440
gttcgtggag gccacacgca ccccagagca gcgtaccctg gtggcggcgg cgggcgca     4500 ccgcctgcag ctgggctggg cgccggcggt gcgcggcgca aagccggggc gccgccggg    4560 cgtggtggcg ggcgacgggc ggcgcccggc ggcgccggag acgcagcagt ggatggcgct    4620
```

```
ggaggagttg cgtcggcagc gcgcggaagc gcgacggctg acggcgcaac gcacggcgcg     4680
actgcgggcg gaggaggcgg cagccgccgc cggtggtggt gaggcgggtg ccgccgccgc     4740
ggcggcggcg ctggcgatgg gctccactgg atccatggga agcatggacg gcgatgaggg     4800
ctacgatgac gagatccagg atcctgtgat gtacggcgcg gatcttggat ccgggccatt     4860
gccacggagg cggttggagg accaggacgc ggattattat gaggagcctg aatccatggc     4920
gctgccgcct ctggatgcag tgcgccgccc catgcccgat gccgacgaca tggatctcat     4980
gcgcggctcc caccaccacc accaccacct cggcgagcag aagctgatct ccgaggagga     5040
cctgggtaac cgatacccct acgacgtgcc cgactacgcc taccccacg acgtgcccga      5100
ctacgccgat cgatccggac cgtaccccta cgacgtgccc gactacgccg ctagcagtac     5160
tcgccggccc cccgacaggc ctccccgtaa cctggtcatc ggaggaggtg ccaggcttcc     5220
gacggccggc gttagcgcat ttgtatgcat gagcgcggtt gtttacatgc tggtgggcgt     5280
ggtgcgcggg gggccggcgg cgtcgggtgc tggtgtggtg tgctagtttt agccagcata     5340
ccgtacactc ctggcggcca actcgagttg tagcttgaat gcatatgcag acaggaaggc     5400
agttgtgtga ggtgggggc ggacagcgta atggagtacc gtcagtaaga ggatggagtc      5460
acggagcatg tgctagaatg ttcctgagtg ctgcatgaac tggctactgc cttggggagt     5520
cgaccgcgcc tgcggtggtt gggtcagtct cagcaatttc aggtgggtga tgagacgatg     5580
agctctaatg catattatcg tatgcgctgc tgcctgcgca ctctcgctgt gtgagaggag     5640
ggctacagta ggctaggccg tgtagggcgt gcaggcaaca caagagagcc agtcaagcag     5700
agagagagag ggaggggca ggtgttgcag tgagaactgg aatcgtgtcg cagacagatt      5760
gcaaggcgta gtcccacggc ggctatctgc acacagagct gccgtgtgac atgtgcaaaa     5820
gggcgtgagg agatggcagt ggctgtaaca agaacaaaga gcggccgcga attcgatatc     5880
aagcttatcg ata                                                        5893

<210> SEQ ID NO 11
<211> LENGTH: 2607
<212> TYPE: DNA
<213> ORGANISM: Chlamydomonas sp.

<400> SEQUENCE: 11
ctcgagcaga ggttgggaat cgctttgaaa atccagcaat cgggtctcag ctgtctcagg      60
ccgcacgcgc cttggacaag gcacttcagt aacgtactcc aagccctcta tctgcatgcc     120
cacaaagcgc aggaatgccg accatcgtgc cagactgtgc cgcgcccgaa ccgaaatccg     180
tcactcccct tggttcccat ggtggcatgg tccccctgt tcgcccaaag cctggttcag      240
cgcccagtgg caaacggctt tggctcagct ccttggtatt gctggtttct agcaatctcg     300
tccgttcctc tgttgccaat gtagcaggtg caaacagtcg aatacggttt tactcagggg     360
caatctcaac taacagaggc cctgggcctg ttgcctggaa cctatgaaga cgataatgcc     420
acggcgactt tcgagcctga gggaagtttg caccggtacc gcattgtgca aggttacggt     480
acatgatagg gggagtgcga cgcggtaagg cttggcgcag cttggcgcgt ctgccttgca     540
tgcatgtccg aaacacgcca cgtcgcgcca cgaaaagcgg taaaaggacc tgccatggtc     600
ctccagggtg ttaccacttc catttcgctc agctgggatg gtgctcgtag gtgcaccagc     660
gttgattatt tcaggcagga agcggctgcg aagcccgcct tcactgaagg actgggatga     720
gcgcacctgt acctgccagt atggtaccgg cgcgctaccg atgcgtgtag tagagcttgc     780
```

```
tgccatacag taactctggt accccagcc accgggcgta gcgagcagac tcaataagta      840
tgatgggttc ttattgcagc cgctgttaca gtttacagcg caaggaaca cgcccctcat      900
tcacagaact aactcaacct actccatcca tatgcttcag ttggcgaacc gtagcgtgag      960
ggctaaggcc gctcgtgcca gccaaagcgc tcggagtgtc tcgtgtgcgg ctgccaagcg     1020
cggtgcggat gttgctcccc tgacgtcggc cctggcggtc accgcatcca tcctgctcac     1080
gactggcgcg gcgagcgcta gcgcagctga cctcgctctc ggcgcccagg tcttcaacgg     1140
caactgtggt gagtagctca tgcaaattta gcatgatcga aggctgcgcg tgtcatgggt     1200
ctccgctcgc tgttcgacat gccgtttcgc tcaactgcac catcgactat cggtcccct     1260
ccttccactt ctggcccacg cagccgcgtg ccacatgggc ggtcgcaaca gcgtgatgcc     1320
cgagaagacg ctggacaagg ccgcccttga gcagtacctg gatggcggct tcaaggtgga     1380
gagcatcatc tatcaggtcg gacatcccc gaccagggc ggcggggatg ttgctgggcc      1440
gatggaaagt agcaacccag ccagcggctt ccagcgcact ccagctgctc acggttgcga     1500
cattgcgcgt gcacgcttgc gcgtccctca ctcggccagc ttgtcgccgc agacatcct     1560
agcattgtgc ggactgcggt cgtcagttag cgtagtggcg gggctcaaag cgtgatgcag     1620
ctggtggctg attgcatgtg ctacatatgc tgttatgttt tgcatgaact tcgatgcatt     1680
ggatgctggg tgcacgcgtt tgcatgtgtt tgtgccggca tgctgccgtc gtcggccgta     1740
cgtttacgtt tctgtgtgcc ggggtcttta tttccgcctg caggtggaga atggcaaggg     1800
ggcgatgccg gcgtgggcgg atcggctgtc ggaggaggaa atccaggctg tggcggagta     1860
cgtgttcaag caggccacgg atgccgcctg gaagtactag gttgatgttg ttatttcaac     1920
tgggtcaccg tagctagctc gtgccccagt tgtggatgcg agttatacgt cattgcgtaa     1980
catgttcatg atagactgca ttaggtaggc gtcgtgtgtg agcacataca gaagtcatca     2040
cgcaaatgga cacgttccgg cgaacccgag gggaaaggct tgggccagta cattatttca     2100
acactaaaat atgtaacata atggaacttg agcacggtcc gggagcgcag gctgggcttg     2160
ggggtcgcgg ctcgagggag aggggcgacg ttggggcagg tcggggcttc aaccgggttt     2220
tgcacggccg aaccatgaac gcgctttggc cagccaagat actgaaaata caacagaagg     2280
atatccagta tgtagcaaag ccttcaaaca gcgtgtacaa gcaagcctgt gacaaagcgg     2340
acccggccgt gaagtccacg gtatttcctc aagcagcatt cagatgagag aaggaatggg     2400
ctctccatct gtttacattc agtcgcattc cacttgtcct ggcgcatcgt ctgtcgctag     2460
acgtcgccgc tcaaagcgtt ttcgcggtgg cagcaccggc taagaaccga aggcgatcgc     2520
agtccatttt cctgacgttg gacgctttga gggcacgagg cgatggctgc gggctgcggg     2580
ctgcatggtt gtttccggag cagagtc                                         2607
```

<210> SEQ ID NO 12
<211> LENGTH: 1716
<212> TYPE: DNA
<213> ORGANISM: Chlamydomonas sp.

<400> SEQUENCE: 12

```
gagtcatatg aaattaaatg gatatttggt acatttaatt ccacaaaaat gtccaatact       60
taaaatacaa aattaaaagt attagttgta aacttgacta acattttaaa ttttaaattt      120
tttcctaatt atatatttta cttgcaaaat ttataaaaat tttatgcatt tttatatcat      180
aataataaaa ccctttattca tggttttataa tataataatt gtgatgacta tgcacaaagc      240
agttctagtc ccatatatat aactatatat aacccgttta agatttatt taaaaatatg       300
```

-continued

```
tgtgtaaaaa atgcttattt ttaatttat tttatataag ttataatatt aaatacacaa      360
tgattaaaat taaataataa taaatttaac gtaacgatga gttgtttttt tattttggag      420
atacacgcaa tgacaattgc gatcggtaca tatcaagaga aacgcacatg gttcgatgac      480
gctgatgact ggcttcgtca agaccgtttc gtattcgtag gttggtcagg tttattacta      540
ttcccttgtg cttactttgc attaggtggt tggttaactg gtactactt cgttacttca      600 tggtatacgc atggtttagc tacttcttac ttagaaggtt gtaacttctt aacagcagct      660
gtttctacac ctgctaacag tatggctcac tctcttctat ttgtttgggg tccagaagct      720
caaggtgatt tcactcgttg gtgtcaactt ggtggttat gggcattcgt tgctttacac      780
ggtgcatttg gtttaattgg tttcatgctt cgtcagtttg aaattgctcg ttcagtaaac      840
ttacgtccat acaacgcaat tgctttctca gcaccaattg ctgtattcgt ttcagtattc      900
ctaatttacc cattaggtca atcaggttgg ttctttgcac ctagtttcgg tgtagctgct      960
atcttccgtt tcattttatt cttccaaggt ttccacaact ggacacttaa cccattccac     1020
atgatgggtg ttgctggtgt tttaggtgct gctttattat gtgctattca cggtgctact     1080
gttgaaaaca cattattcga agacggtgac ggtgctaaca cattccgtgc attcaaccct     1140
acacaggctg aagaaacata ctctatggtt actgctaacc gtttctggtc acaaatcttc     1200
ggtgttgctt tctctaacaa acgttggctt cacttcttca tgttattagt tccagtaact     1260
ggtctttgga tgagtgctat tggtgttgta ggtttagctc taaacttacg tgcttacgac     1320
ttcgtatcac aagagattcg tgctgctgaa gaccctgaat tcgaaacatt ctacactaaa     1380
aacattcttc ttaacgaagg tattcgtgct tggatggctg ctcaagacca accacacgaa     1440
cgtttagtat tccctgaaga agtattacca cgtggtaacg ctctataata tattttata     1500 taaattacca atactaatta gtattggtaa tttatattac tttattattt aaaagaaaat     1560
gcccctttgg ggctaaaaat cacatgagtg cttgagccgt atgcgaaaaa actcgcatgt     1620
acggttcttt aggaggattt aaaatattaa aaaataaaaa aacaaatcct acctgactaa     1680
accaggacat ttttcacgta ctctgtcaaa aggtcc                               1716
```